United States Patent
Dooley et al.

(10) Patent No.: US 12,257,313 B2
(45) Date of Patent: *Mar. 25, 2025

(54) PREPARATION OF THERAPEUTIC EXOSOMES USING MEMBRANE PROTEINS

(71) Applicant: LONZA SALES AG, Basel (CH)

(72) Inventors: Kevin P. Dooley, Boston, MA (US); Rane A. Harrison, Belmont, MA (US); Russell E. McConnell, Brighton, MA (US); Ke Xu, Sudbury, MA (US); Damian J. Houde, Plymouth, MA (US); Nikki Ross, Cambridge, MA (US); Sonya Haupt, Cambridge, MA (US); John D. Kulman, Belmont, MA (US); Douglas E. Williams, Boston, MA (US)

(73) Assignee: LONZA SALES AG, Basel (CH)

( * ) Notice: Subject to any disclaimer, the term of this patent is extended or adjusted under 35 U.S.C. 154(b) by 104 days.

This patent is subject to a terminal disclaimer.

(21) Appl. No.: 18/050,005

(22) Filed: Oct. 26, 2022

(65) Prior Publication Data

US 2024/0009322 A1 Jan. 11, 2024

Related U.S. Application Data

(60) Division of application No. 16/722,884, filed on Dec. 20, 2019, now Pat. No. 11,679,164, which is a continuation of application No. 16/231,012, filed on Dec. 21, 2018, now Pat. No. 10,561,740, which is a continuation of application No. 16/112,547, filed on Aug. 24, 2018, now Pat. No. 10,195,290.

(60) Provisional application No. 62/656,956, filed on Apr. 12, 2018, provisional application No. 62/550,543, filed on Aug. 25, 2017.

(51) Int. Cl.
| | |
|---|---|
| *A61K 47/69* | (2017.01) |
| *C07K 14/705* | (2006.01) |
| *C07K 14/71* | (2006.01) |
| *C07K 14/755* | (2006.01) |
| *C07K 16/28* | (2006.01) |
| *A61K 38/00* | (2006.01) |

(52) U.S. Cl.
CPC ........ *A61K 47/6917* (2017.08); *C07K 14/705* (2013.01); *C07K 14/70503* (2013.01); *C07K 14/70596* (2013.01); *C07K 14/71* (2013.01); *C07K 14/755* (2013.01); *C07K 16/2803* (2013.01); *C07K 16/2851* (2013.01); *A61K 38/00* (2013.01); *C07K 2317/55* (2013.01); *C07K 2317/622* (2013.01); *C07K 2319/00* (2013.01); *C07K 2319/30* (2013.01); *C07K 2319/43* (2013.01); *C07K 2319/60* (2013.01)

(58) Field of Classification Search
None
See application file for complete search history.

(56) References Cited

U.S. PATENT DOCUMENTS

| | | | |
|---|---|---|---|
| 5,747,660 | A | 5/1998 | Orlicky et al. |
| 9,518,125 | B2 | 12/2016 | Yong et al. |
| 10,195,290 | B1 | 2/2019 | Dooley et al. |
| 10,561,740 | B2 | 2/2020 | Dooley et al. |
| 11,679,164 | B2 | 6/2023 | Dooley et al. |
| 2004/0049010 | A1 | 3/2004 | Warren et al. |
| 2005/0119215 | A1 | 6/2005 | Al-Mahmood et al. |
| 2013/0156801 | A1 | 6/2013 | Bond et al. |
| 2014/0179006 | A1 | 6/2014 | Zhang |
| 2015/0290343 | A1 | 10/2015 | Lotvall et al. |
| 2015/0301058 | A1 | 10/2015 | Schettini et al. |
| 2019/0060483 | A1 | 2/2019 | Dooley et al. |
| 2019/0117792 | A1 | 4/2019 | Dooley et al. |
| 2020/0222556 | A1 | 7/2020 | Dooley et al. |

FOREIGN PATENT DOCUMENTS

| | | |
|---|---|---|
| WO | 2001/093836 A2 | 12/2001 |
| WO | 2007/053648 A2 | 5/2007 |
| WO | 2007/126386 A1 | 11/2007 |
| WO | 2012/048372 A1 | 4/2012 |
| WO | 2014/138793 A1 | 9/2014 |
| WO | 2016/057755 A1 | 4/2016 |
| WO | 2016/077639 A2 | 5/2016 |
| WO | 2017/075708 A1 | 5/2017 |
| WO | 2017/117585 A1 | 7/2017 |
| WO | 2017/161010 A1 | 9/2017 |
| WO | 2018/226758 A2 | 12/2018 |
| WO | 2019/040920 A1 | 2/2019 |

OTHER PUBLICATIONS

Abache et al., "The transferrin receptor and the tetraspanin web molecules CD9, CD81, and CD9P-1 are differentially sorted into exosomes after TPA treatment of K562 cells," Journal of Cellular Biochemistry 102(3):650-664 (2007).

(Continued)

*Primary Examiner* — Daniel C Gamett

(74) *Attorney, Agent, or Firm* — MEDLER FERRO WOODHOUSE & MILLS PLLC

(57) ABSTRACT

The present invention relates to methods of preparing a therapeutic exosome using a protein newly-identified to be enriched on the surface of exosomes. Specifically, the present invention provides methods of using the proteins for affinity purification of exosomes. It also provides methods of localizing a therapeutic peptide on exosomes, and targeting exosomes to a specific organ, tissue or cell by using the proteins. The methods involve generation of surface-engineered exosomes that include one or more of the exosome proteins at higher density, or a variant or a fragment of the exosome protein.

19 Claims, 45 Drawing Sheets

Figure 1:
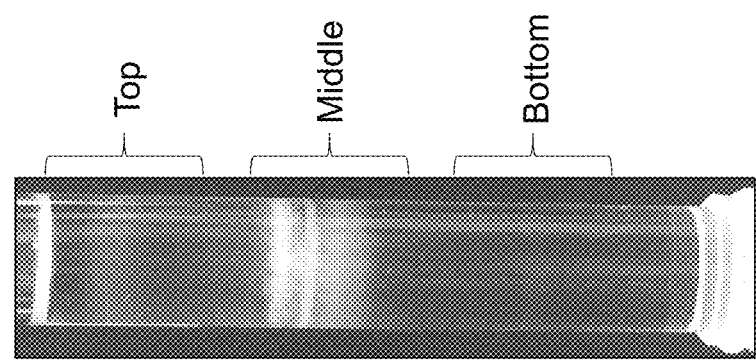

Specification includes a Sequence Listing.

(56) References Cited

OTHER PUBLICATIONS

Bellavia et al., "Interleukin 3-receptor targeted exosomes inhibit in vitro and in vivo Chronic Myelogenous Leukemia cell growth," Theranostics 7(5):1333-1345 (2017).

Koojimans et al., "Modulation of tissue tropism and biological activity of exosomes and other extracellular vesicles: New nanotools for cancer treatment," Pharmacology Research 111:487-500 (2016).

Lai et al., "Mesenchymal Stem Cell Exosome: a Novel Stem Cell Based Therapy for Cardiovascular Disease," Regenerative Medicine 6(4);481-492 (2011).

Luga et al., "Exosomes mediate stromal mobilization of autocrine Wnt-PCP signaling in breast cancer cell migration," Cell 151(7):1542-1556 (2012).

Moss et al., "Shedding of Membrane Proteins by ADAM Family Proteases." Essays in Biochemistry 38:141-154 (2002).

Tauro et al., "Comparison of ultracentrifugation, density gradient separation, and immunoaffinity capture methods for isolating human colon cancer cell line LIM1863-derived exosomes," Methods 56(2):293-204 (2012).

Yang et al., "Exosome Mediated Delivery of miR-124 Promotes Neurogenesis after ischemia," Molecular Therapeutic Nucleic Acids 7:278-287 (2017).

PCT International Search Report and Written Opinion in PCT/US2018/048026 dated Oct. 30, 2018.

Notice of Allowance issued in U.S. Appl. No. 16/112,547, dated Nov. 21, 2018.

Notice of Allowance issued in U.S. Appl. No. 16/112,547, dated Dec. 12, 2018.

Non-Final Office Action issued in U.S. Appl. No. 16/231,012, dated Mar. 28, 2019.

Notice of Allowance issued in U.S. Appl. No. 16/231,012, dated Sep. 24, 2019.

Notice of Allowance issued in U.S. Appl. No. 16/231,012, dated Jan. 22, 2020.

Non-Final Office Action issued in U.S. Appl. No. 16/722,884, dated Dec. 20, 2019.

Notice of Allowance issued in U.S. Appl. No. 16/722,884, dated Feb. 6, 2023.

Figure 3

PTGFRN (Q9P2B2)

[Sequence alignment figure showing the PTGFRN protein sequence (UniProt Q9P2B2) with modification annotations along positions 1–879. The sequence is displayed in rows of 100 residues with modification markers (C, D, O) annotated above specific residues.]

Modifications
C: Carbamidomethyl (C)
D: Deamidated (Q, N)
O: Oxidation (M)

Figure 4

IGSF8 (Q969P0)

```
                    1       101      201      301      401      501    613

Modifications       1
Q969P0                  MCALRPTLLP PSLPLLHLH LCHSCWAPEV LVPEGIVTW ACIAVSIEGN NPFWFLVPPT APITALGIVS TRNTNRSYNV
                                                              C
Modifications      91
Q969P0                  EKSNYACKV QVQRLQGDAV VLKIARLQRQ BAGIYTECHD TETKYLGT MSVIELHLP HYLQVSAAPP GPHGRJAPTS YYZSTYNKGQ
                                                              C
Modifications     181
Q969P0                  ELRLGGLAART STQRHTHLAV SNGRSVPHAP VGRSTIQEVT CRRBLATER GRVTAELHA GELRLGREGT EVYPHVGGA QAGLAGTYRC
                                                 D        D
Modifications     271
Q969P0                  TAAEWIQDPD GSEAQIAKKR AVLRHFPQT LSSQIATVTK PGRRIGSEE PLELLCNVSG ALPACDMAA YSRQWERAPA GAPGRELVA
                        D
Modifications     361
Q969P0                  QLDTEGVGSL GPGYEGRHIA MKKVASETTR LRLRARPCA RGTTRLAR2 VYPGSCIHLS RAASASPPL FHRTEEGRTV LEANMLAGG
Modifications     451
Q969P0                  TVYRKSTASL LCNISVREGP PCLRLAAEMS VRFSPGHLS SVPAGIRGSP COPCHAKLY FPGGSVSVI LNCPESHELD LHSLGTEDRG
Modifications     541
Q969P0                  VYNCAPSAMP QHADYSEVQA GSARSGPVTV VPPMAIPTL PVPLAVGISV AIVTGATVLG TICCPHREL PRP
```

Modifications
C: Carbamidomethyl (C)
D: Deamidated (Q)

Figure 5

BSG (P35613)

```
                          1           11          21          31          41
Modifications
P35613                    MAAALFVLLG FALLCTHGAS GAAGFVQAPL SQQEWVGSSV ELHCEAVGSP VPEIQWWFEG 51          61          71          81          91
Modifications                                       C
P35613        51          QGPEMTCSQL MEGARLDRVH IRATTHQHLA STISIDTLVE 101         111         121         131         141
Modifications
P35613        101         EDTGTYECRA SSDPDRNHLT RAPRVKWVRA QAVVLHPEGG TVLLRCEAEG DPVPTIRWRK 151         161         171         181         191
Modifications                                                  D           D  C
P35613        151         EGGELPKQRA EGDSVRLRCQ LGQDVHPRAE VRWYKNGRPL VPGDTARSVD RHSVLHDSGN 201         211         221         231         241
Modifications              C                                    C
P35613        201         YSCVLRNPSG QREETRLEVT VKGSESMPPY TEESSRYKIT SHSALHGS ESREYSSSGQ GSLRLHSEGL 251         261         271         281         291
Modifications                                                                           O
P35613        251         KRRADPPFGQ YH 301         311         321         331         341
Modifications
P35613        301         GNGTSEGSSR QRITLRVLAS HLAALWPFLG IVAELVLVT IIFIYEKRRK PEDVLDDDDA GSAPLKSSGQ HQNDKGKNVR QRNSS
```

Modifications
C: Carbamidomethyl (C)
D: Deamidated (N, Q)
O: Oxidation (M)

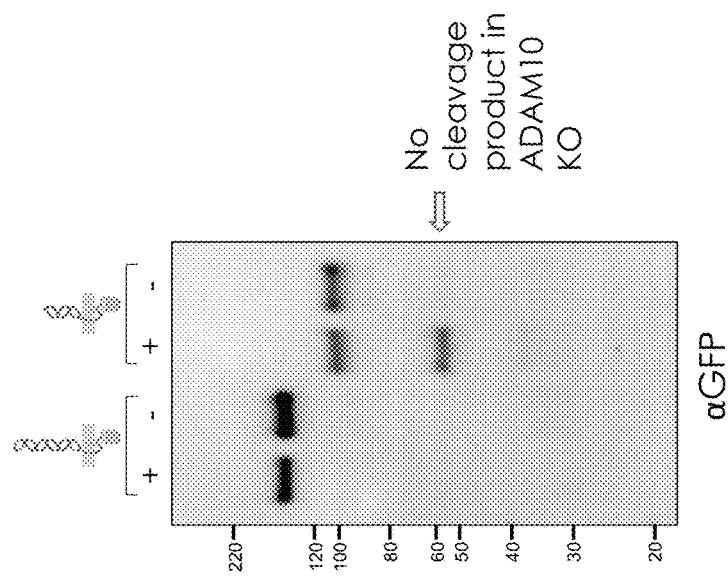
Figure 12C
Figure 12B
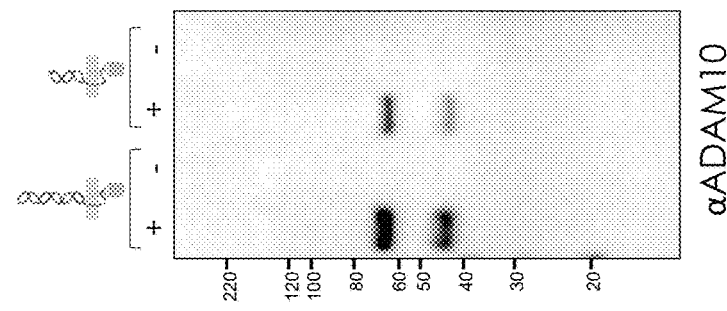
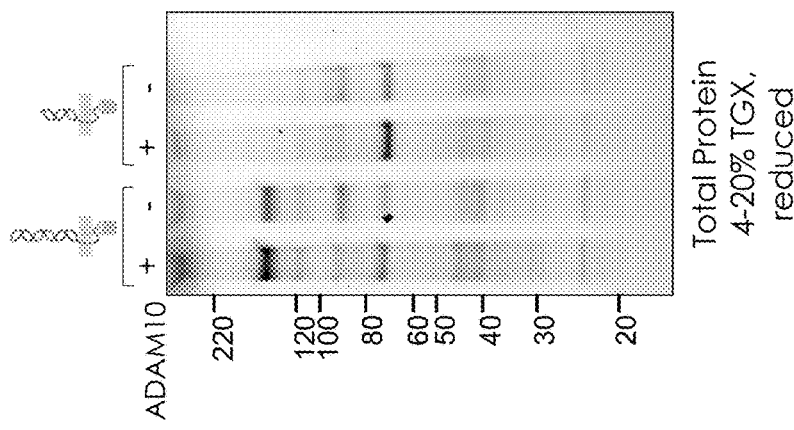
Figure 12A

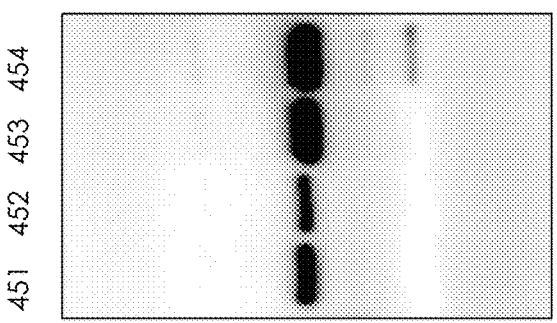
Figure 14C
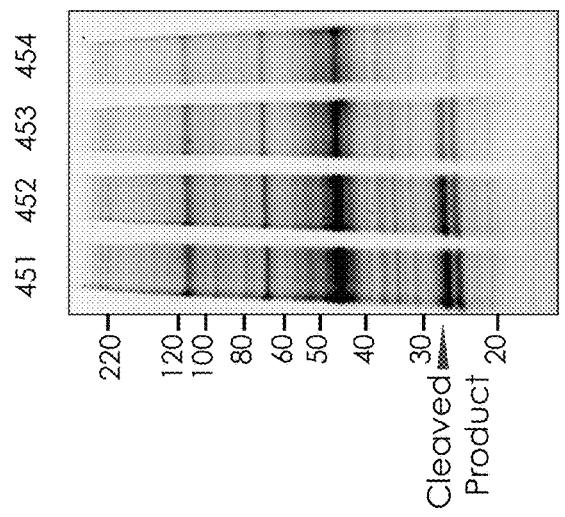
Figure 14B
Figure 14A

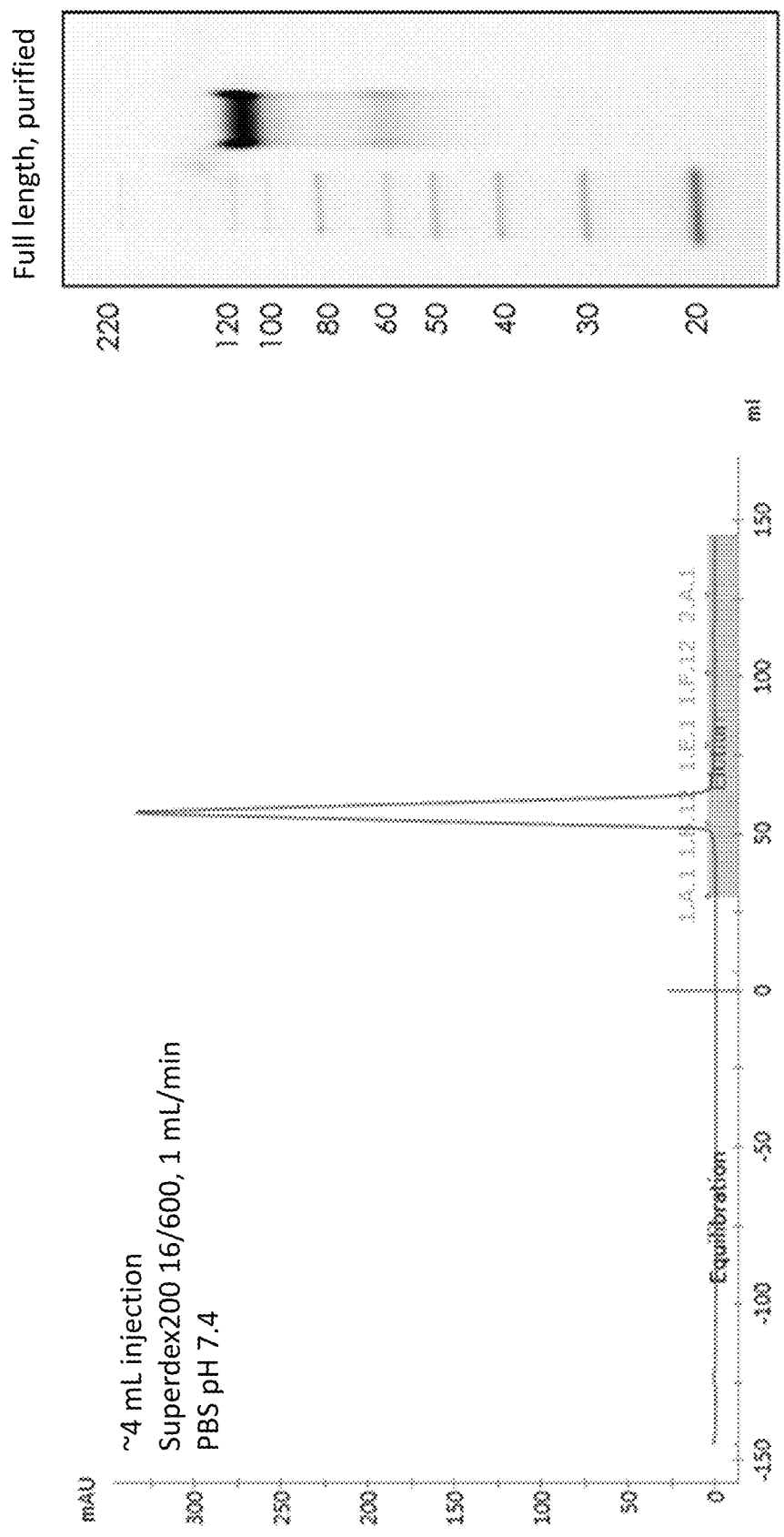

Figure 21

PTGFRN Ectodomain Binding Partners (pH 7.4)

| Rank | Name | A Score |
|---|---|---|
| 1 | LGALS1 | 144.801 |
| 2 | FCN1 | 20.788 |
| 3 | MGAT4B | 9.738 |

PTGFRN Ectodomain Binding Partners (pH 5.6)

| Rank | Name | A Score |
|---|---|---|
| 1 | EPN1 | 112.017 |
| 2 | LGALS1 | 82.059 |
| 3 | ZCCHC8 | 29.974 |
| 4 | MGAT4B | 13.778 |
| 5 | FCN1 | 10.605 |

Figure 31

No. of Peptide Spectrum Matches (PSMs)

| Gene Name | HEK | HT1080 | K562 | MB231 | Raji | MSC* |
|---|---|---|---|---|---|---|
| PTGFRN | 197 | 151 | 37 | 0 | 0 | 111 |
| IGSF8 | 61 | 19 | 31 | 5 | 10 | 52 |
| IGSF3 | 5 | 3 | 14 | 0 | 0 | 0 |
| BSG | 91 | 60 | 62 | 24 | 48 | 82 |
| SLC3A2 | 163 | 117 | 59 | 117 | 95 | 35 |
| ITGB1 | 74 | 400 | 82 | 252 | 95 | 319 |
| CD81 | 34 | 21 | 2 | 9 | 9 | 48 |
| CD9 | 21 | 6 | 0 | 31 | 0 | 41 |

*Performed in a separate experiment scFab-αCLEC9A-PTGFRN-mEGFP-FLAG

```
SEQUENCE LISTING

Sequence total quantity: 46
SEQ ID NO: 1            moltype = AA  length = 879
FEATURE                 Location/Qualifiers
source                  1..879
                        mol_type = protein
                        organism = Homo sapiens
SEQUENCE: 1
MGRLASRPLL LALLSLALCR GRVVRVPTAT LVRVVGTELV IPCNVSDYDG PSEQNFDWSF   60
SSLGSSFVEL ASTWEVGFPA QLYQERLQRG EILLRRTAND AVELHIKNVQ PSDQGHYKCS  120
TPSTDATVQG NYEDTVQVKV LADSLHVGPS ARPPPSLSLR EGEPFELRCT AASASPLHTH  180
LALLWEVHRG PARRSVLALT HEGRFHPGLG YEQRYHSGDV RLDTVGSDAY RLSVSRALSA  240
DQGSYRCIVS EWIAEQGNWQ EIQEKAVEVA TVVIQPSVLR AAVPKNVSVA EGKELDLTCN  300
ITTDRADDVR PEVTWSFSRM PDSTLPGSRV LARLDRDSLV HSSPHVALSH VDARSYHLLV  360
RDVSKENSGY YYCHVSLWAP GHNRSWHKVA EAVSSPAGVG VTWLEPDYQV YLNASKVPGF  420
ADDPTELACR VVDTKSGEAN VRFTVSWYYR MNRRSDNVVT SELLAVMDGD WTLKYGERSK  480
QRAQDGDFIF SKEHTDTFNF RIQRTTEEDR GNYYCVVSAW TKQRNNSWVK SKDVFSKPVN  540
IFWALEDSVL VVKARQPKPF FAAGNTFEMT CKVSSKNIKS PRYSVLIMAE KPVGDLSSPN  600
ETKYIISLDQ DSVVKLENWT DASRVDGVVL EKVQEDEFRY RMYQTQVSDA GLYRCMVTAW  660
SPVRGSLWRE AATSLSNPIE IDFQTSGPIF NASVHSDTPS VIRGDLIKLF CIITVEGAAL  720
DPDDMAFDVS WFAVHSFGLD KAPVLLSSLD RKGIVTTSRR DWKSDLSLER VSVLEFLLQV  780
HGSEDQDFGN YYCSVTPWVK SPTGSWQKEA EIHSKPVFIT VKMDVLNAFK YPLLIGVGLS  840
TVIGLLSCLI GYCSSHWCCK KEVQETRRER RRLMSMEMD                        879

SEQ ID NO: 2            moltype = AA  length = 731
FEATURE                 Location/Qualifiers
source                  1..731
                        mol_type = protein
                        organism = Homo sapiens
SEQUENCE: 2
PSARPPPSLS LREGEPFELR CTAASASPLH THLALLWEVH RGPARRSVLA LTHEGRFHPG   60
LGYEQRYHSG DVRLDTVGSD AYRLSVSRAL SADQGSYRCI VSEWIAEQGN WQEIQEKAVE  120
VATVVIQPSV LRAAVPKNVS VAEGKELDLT CNITTDRADD VRPEVTWSFS RMPDSTLPGS  180
RVLARLDRDS LVHSSPHVAL SHVDARSYHL LVRDVSKENS GYYYCHVSLW APGHNRSWHK  240
VAEAVSSPAG VGVTWLEPDY QVYLNASKVP GFADDPTELA CRVVDTKSGE ANVRFTVSWY  300
YRMNRRSDNV VTSELLAVMD GDWTLKYGER SKQRAQDGDF IFSKEHTDTF NFRIQRTTEE  360
DRGNYYCVVS AWTKQRNNSW VKSKDVFSKP VNIFWALEDS VLVVKARQPK PFFAAGNTFE  420
MTCKVSSKNI KSPRYSVLIM AEKPVGDLSS PNETKYIISL DQDSVVKLEN WTDASRVDGV  480
VLEKVQEDEF RYRMYQTQVS DAGLYRCMVT AWSPVRGSLW REAATSLSNP IEIDFQTSGP  540
IFNASVHSDT PSVIRGDLIK LFCIITVEGA ALDPDDMAFD VSWFAVHSFG LDKAPVLLSS  600
LDRKGIVTTS RRDWKSDLSL ERVSVLEFLL QVHGSEDQDF GNYYCSVTPW VKSPTGSWQK  660
EAEIHSKPVF ITVKMDVLNA FKYPLLIGVG LSTVIGLLSC LIGYCSSHWC CKKEVQETRR  720
ERRRLMSMEM D                                                      731

SEQ ID NO: 3            moltype = AA  length = 611
FEATURE                 Location/Qualifiers
source                  1..611
                        mol_type = protein
                        organism = Homo sapiens
SEQUENCE: 3
VATVVIQPSV LRAAVPKNVS VAEGKELDLT CNITTDRADD VRPEVTWSFS RMPDSTLPGS   60
RVLARLDRDS LVHSSPHVAL SHVDARSYHL LVRDVSKENS GYYYCHVSLW APGHNRSWHK  120
VAEAVSSPAG VGVTWLEPDY QVYLNASKVP GFADDPTELA CRVVDTKSGE ANVRFTVSWY  180
YRMNRRSDNV VTSELLAVMD GDWTLKYGER SKQRAQDGDF IFSKEHTDTF NFRIQRTTEE  240
```

```
DRGNYYCVVS AWTKQRNNSW VKSKDVFSKP VNIFWALEDS VLVVKARQPK PFFAAGNTFE  300
MTCKVSSKNI KSPRYSVLIM AEKPVGDLSS PNETKYIISL DQDSVVKLEN WTDASRVDGV  360
VLEKVQEDEF RYRMYQTQVS DAGLYRCMVT AWSPVRGSLW REAATSLSNP IEIDFQTSGP  420
IFNASVHSDT PSVIRGDLIK LFCIITVEGA ALDPDDMAFD VSWFAVHSFG LDKAPVLLSS  480
LDRKGIVTTS RRDWKSDLSL ERVSVLEFLL QVHGSEDQDF GNYYCSVTPW VKSPTGSWQK  540
EAEIHSKPVF ITVKMDVLNA FKYPLLIGVG LSTVIGLLSC LIGYCSSHWC CKKEVQETRR  600
ERRRLMSMEM D                                                      611

SEQ ID NO: 4           moltype = AA   length = 485
FEATURE                Location/Qualifiers
source                 1..485
                       mol_type = protein
                       organism = Homo sapiens
SEQUENCE: 4
SPAGVGVTWL EPDYQVYLNA SKVPGFADDP TELACRVVDT KSGEANVRFT VSWYYRMNRR  60
SDNVVTSELL AVMDGDWTLK YGERSKQRAQ DGDFIFSKEH TDTFNFRIQR TTEEDRGNYY  120
CVVSAWTKQR NNSWVKSKDV FSKPVNIFWA LEDSVLVVKA RQPKPFFAAG NTFEMTCKVS  180
SKNIKSPRYS VLIMAEKPVG DLSSPNETKY IISLDQDSVV KLENWTDASR VDGVVLEKVQ  240
EDEFRYRMYQ TQVSDAGLYR CMVTAWSPVR GSLWREAATS LSNPIEIDFQ TSGPIFNASV  300
HSDTPSVIRG DLIKLFCIIT VEGAALDPDD MAFDVSWFAV HSFGLDKAPV LLSSLDRKGI  360
VTTSRRDWKS DLSLERVSVL EFLLQVHGSE DQDFGNYYCS VTPWVKSPTG SWQKEAEIHS  420
KPVFITVKMD VLNAFKYPLL IGVGLSTVIG LLSCLIGYCS SHWCCKKEVQ ETRRERRRLM  480
SMEMD                                                             485

SEQ ID NO: 5           moltype = AA   length = 343
FEATURE                Location/Qualifiers
source                 1..343
                       mol_type = protein
                       organism = Homo sapiens
SEQUENCE: 5
KPVNIFWALE DSVLVVKARQ PKPFFAAGNT FEMTCKVSSK NIKSPRYSVL IMAEKPVGDL  60
SSPNETKYII SLDQDSVVKL ENWTDASRVD GVVLEKVQED EFRYRMYQTQ VSDAGLYRCM  120
VTAWSPVRGS LWREAATSLS NPIEIDFQTS GPIFNASVHS DTPSVIRGDL IKLFCIITVE  180
GAALDPDDMA FDVSWFAVHS FGLDKAPVLL SSLDRKGIVT TSRRDWKSDL SLERVSVLEF  240
LLQVHGSEDQ DFGNYYCSVT PWVKSPTGSW QKEAEIHSKP VFITVKMDVL NAFKYPLLIG  300
VGLSTVIGLL SCLIGYCSSH WCCKKEVQET RRERRRLMSM EMD                   343

SEQ ID NO: 6           moltype = AA   length = 217
FEATURE                Location/Qualifiers
source                 1..217
                       mol_type = protein
                       organism = Homo sapiens
SEQUENCE: 6
VRGSLWREAA TSLSNPIEID FQTSGPIFNA SVHSDTPSVI RGDLIKLFCI ITVEGAALDP  60
DDMAFDVSWF AVHSFGLDKA PVLLSSLDRK GIVTTSRRDW KSDLSLERVS VLEFLLQVHG  120
SEDQDFGNYY CSVTPWVKSP TGSWQKEAEI HSKPVFITVK MDVLNAFKYP LLIGVGLSTV  180
IGLLSCLIGY CSSHWCCKKE VQETRRERRR LMSMEMD                          217

SEQ ID NO: 7           moltype = AA   length = 66
FEATURE                Location/Qualifiers
source                 1..66
                       mol_type = protein
                       organism = Homo sapiens
SEQUENCE: 7
SKPVFITVKM DVLNAFKYPL LIGVGLSTVI GLLSCLIGYC SSHWCCKKEV QETRRERRRL  60
MSMEMD                                                            66

SEQ ID NO: 8           moltype = AA   length = 21
FEATURE                Location/Qualifiers
source                 1..21
                       mol_type = protein
                       organism = Homo sapiens
SEQUENCE: 8
MGRLASRPLL LALLSLALCR G                                           21

SEQ ID NO: 9           moltype = AA   length = 385
FEATURE                Location/Qualifiers
source                 1..385
                       mol_type = protein
                       organism = Homo sapiens
SEQUENCE: 9
MAAALFVLLG FALLGTHGAS GAAGFVQAPL SQQRWVGGSV ELHCEAVGSP VPEIQWWFEG  60
QGPNDTCSQL WDGARLDRVH IHATYHQHAA STISIDTLVE EDTGTYECRA SNDPDRNHLT  120
RAPRVKWVRA QAVVLVLEPG TVFTTVEDLG SKILLTCSLN DSATEVTGHR WLKGGVVLKE  180
DALPGQKTEF KVDSDDQWGE YSCVFLPEPM GTANIQLHGP PRVKAVKSSE HINEGETAML  240
VCKSESVPPV TDWAWYKITD SEDKALMNGS ESRFFVSSSQ GRSELHIENL NMEADPGQYR  300
CNGTSSKGSD QAIITLRVRS HLAALWPFLG IVAEVLVLVT TIFIYEKRRK PEDVLDDDDA  360
GSAPLKSSGQ HQNDKGKNVR QRNSS                                       385
```

```
SEQ ID NO: 10              moltype = AA  length = 247
FEATURE                    Location/Qualifiers
source                     1..247
                           mol_type = protein
                           organism = Homo sapiens
SEQUENCE: 10
PGTVFTTVED LGSKILLTCS LNDSATEVTG HRWLKGGVVL KEDALPGQKT EFKVDSDDQW      60
GEYSCVFLPE PMGTANIQLH GPPRVKAVKS SEHINEGETA MLVCKSESVP PVTDWAWYKI     120
TDSEDKALMN GSESRFFVSS SQGRSELHIE NLNMEADPGQ YRCNGTSSKG SDQAIITLRV     180
RSHLAALWPF LGIVAEVLVL VTIIFIYEKR RKPEDVLDDD DAGSAPLKSS GQHQNDKGKN     240
VRQRNSS                                                               247

SEQ ID NO: 11              moltype = AA  length = 168
FEATURE                    Location/Qualifiers
source                     1..168
                           mol_type = protein
                           organism = Homo sapiens
SEQUENCE: 11
HGPPRVKAVK SSEHINEGET AMLVCKSESV PPVTDWAWYK ITDSEDKALM NGSESRFFVS      60
SSQGRSELHI ENLNMEADPG QYRCNGTSSK GSDQAIITLR VRSHLAALWP FLGIVAEVLV     120
LVTIIFIYEK RRKPEDVLDD DDAGSAPLKS SGQHQNDKGK NVRQRNSS                  168

SEQ ID NO: 12              moltype = AA  length = 66
FEATURE                    Location/Qualifiers
source                     1..66
                           mol_type = protein
                           organism = Homo sapiens
SEQUENCE: 12
SHLAALWPFL GIVAEVLVLV TIIFIYEKRR KPEDVLDDDD AGSAPLKSSG QHQNDKGKNV      60
RQRNSS                                                                66

SEQ ID NO: 13              moltype = AA  length = 18
FEATURE                    Location/Qualifiers
source                     1..18
                           mol_type = protein
                           organism = Homo sapiens
SEQUENCE: 13
MAAALFVLLG FALLGTHG                                                   18

SEQ ID NO: 14              moltype = AA  length = 613
FEATURE                    Location/Qualifiers
source                     1..613
                           mol_type = protein
                           organism = Homo sapiens
SEQUENCE: 14
MGALRPTLLP PSLPLLLLLM LGMGCWAREV LVPEGPLYRV AGTAVSISCN VTGYEGPAQQ      60
NFEWFLYRPE APDTALGIVS TKDTQFSYAV FKSRVVAGEV QVQRLQGDAV VLKIARLQAQ     120
DAGIYECHTP STDTRYLGSY SGKVELRVLP DVLQVSAAPP GPRGRQAPTS PPRMTVHEGQ     180
ELALGCLART STQKHTHLAV SFGRSVPEAP VGRSTLQEVV GIRSDLAVEA GAPYAERLAA     240
GELRLGKEGT DRYRMVVGGA QAGDAGTYHC TAAEWIQDPD GSWAQIAEKR AVLAHDVQT      300
LSSQLAVTVG PGERRIGPGE PLELLCNVSG ALPPAGRHAA YSVGWEMAPA GAPGPGRLVA     360
QLDTEGVGSL GPGYEGRHIA MEKVASRTYR LRLEAARPGD AGTYRCLAKA YVRGSGTRLR     420
EAASARSRPL PVHVREEGVV LEAVAWLAGG TVYRGETASL LCNISVRGGP PGLRLAASWW     480
VERPEDGELS SVPAQLVGGV GQDGVAELGV RPGGGPVSVE LVGPRSHRLR LHSLGPEDEG     540
VYHCAPSAWV QHADYSWYQA GSARSGPVTV YPYMHALDTL FVPLLVGTGV ALVTGATVLG     600
TITCCFMKRL RKR                                                        613

SEQ ID NO: 15              moltype = AA  length = 456
FEATURE                    Location/Qualifiers
source                     1..456
                           mol_type = protein
                           organism = Homo sapiens
SEQUENCE: 15
APPGPRGRQA PTSPPRMTVH EGQELALGCL ARTSTQKHTH LAVSFGRSVP EAPVGRSTLQ      60
EVVGIRSDLA VEAGAPYAER LAAGELRLGK EGTDRYRMVV GGAQAGDAGT YHCTAAEWIQ     120
DPDGSWAQIA EKRAVLAHVD VQTLSSQLAV TVGPGERRIG PGEPLELLCN VSGALPPAGR     180
HAAYSVGWEM APAGAPGPGR LVAQLDTEGV GSLGPGYEGR HIAMEKVASR TYRLRLEAAR     240
PGDAGTYRCL AKAYVRGSGT RLREAASARS RPLPVHVREE GVVLEAVAWL AGGTVYRGET     300
ASLLCNISVR GGPPGLRLAA SWWVERPEDG ELSSVPAQLV GGVGQDGVAE LGVRPGGGPV     360
SVELVGPRSH RLRHSLGPE DEGVYHCAPS AWVQHADYSW YQAGSARSGP VTVYPYMHAL      420
DTLFVPLLVG TGVALVTGAT VLGTITCCFM KRLRKR                               456

SEQ ID NO: 16              moltype = AA  length = 320
FEATURE                    Location/Qualifiers
source                     1..320
                           mol_type = protein
                           organism = Homo sapiens
SEQUENCE: 16
AHVDVQTLSS QLAVTVGPGE RRIGPGEPLE LLCNVSGALP PAGRHAAYSV GWEMAPAGAP      60
```

```
GPGRLVAQLD TEGVGSLGPG YEGRHIAMEK VASRTYRLRL EAARPGDAGT YRCLAKAYVR   120
GSGTRLREAA SARSRPLPVH VREEGVVLEA VAWLAGGTVY RGETASLLCN ISVRGGPPGL   180
RLAASWWVER PEDGELSSVP AQLVGGVGQD GVAELGVRPG GGPVSELVG  PRSHRLRLHS   240
LGPEDEGVYH CAPSAWVQHA DYSWYQAGSA RSGPVTVYPY MHALDTLFVP LLVGTGVALV   300
TGATVLGTIT CCFMKRLRKR                                              320

SEQ ID NO: 17           moltype = AA   length = 179
FEATURE                 Location/Qualifiers
source                  1..179
                        mol_type = protein
                        organism = Homo sapiens
SEQUENCE: 17
REEGVVLEAV AWLAGGTVYR GETASLLCNI SVRGGPPGLR LAASWWVERP EDGELSSVPA   60
QLVGGVGQDG VAELGVRPGG GPVSELVGP  RSHRLRLHSL GPEDEGVYHC APSAWVQHAD   120
YSWYQAGSAR SGPVTVYPYM HALDTLFVPL LVGTGVALVT GATVLGTITC CFMKRLRKR    179

SEQ ID NO: 18           moltype = AA   length = 24
FEATURE                 Location/Qualifiers
source                  1..24
                        mol_type = protein
                        organism = Homo sapiens
SEQUENCE: 18
VALVTGATVL GTITCCFMKR LRKR                                         24

SEQ ID NO: 19           moltype = AA   length = 27
FEATURE                 Location/Qualifiers
source                  1..27
                        mol_type = protein
                        organism = Homo sapiens
SEQUENCE: 19
MGALRPTLLP PSLPLLLLLM LGMGCWA                                      27

SEQ ID NO: 20           moltype = AA   length = 1195
FEATURE                 Location/Qualifiers
source                  1..1195
                        mol_type = protein
                        organism = Homo sapiens
SEQUENCE: 20
MKCFFPVLSC LAVLGVVSAQ RQVTVQEGPL YRTEGSHITI WCNVSGYQGP SEQNFQWSIY   60
LPSSPEREVQ IVSTMDSSFP YAIYTQRVRG GKIFIERVQG NSTLLHITDL QARDAGEYEC   120
HTPSTDKQYF GSYSAKMNLV VIPDSLQTTA MPQTLHRVEQ DPLELTCEVA SETIQHSHLS   180
VAWLRQKVGE KPVEVISLSR DFMLHSSSEY AQRSLGEVR  LDKLGRTTFR LTIFHLQPSD   240
QGEFYCEAAE WIQDPDGSWY AMTRKRSEGA VVNVQPTDKE FTVRLETEKR LHTVGEPVEF   300
RCILEAQNVP DRYFAVSWAF NSSLIATMGP NAVPVLNSEF AHREARGQLK VAKESDSVFV   360
LKIYHLRQED SGKYNCRVTE REKTVTGEFI DKESKRPKNI PIIVLPLKSS ISVEVASNAS   420
VILEGEDLRF SCSVRTAGRP QGRFSVIWQL VDRQNRRSSN MWLDRDGTVQ PGSSYWERSS   480
FGGVQMEQVQ PNSFSLGIFN SRKEDEGQYE CHVTEWVRAV DGEWQIVGER RASTPISITA   540
LEMGFAVTAI SRTPGVTYSD SFDLQCIIKP HYPAWVPVSV TWRFQPVGTV EFHDLVTFTR   600
DGGVQWGDRS SSFRTRTAIE KAESSNNVRL SISRASDTEA GKYQCVAELW RKNYNNTWTR   660
LAERTSNLLE IRVLQPVTKL QVSKSKRTLT LVENKPIQLN CSVKSQTSQN SHFAVLWYVH   720
KPSDADGKLI LKTTHNSAFE YGTYAEEEGL RARLQFERHV SGGLFSLTVQ RAEVSDSGSY   780
YCHVEEWLLS PNYAWYKLAE EVSGRTEVTV KQPDSRLRLS QAQGNLSVLE TRQVQLECVV   840
LNRTSITSQL MVEWFVWKPN HPERETVARL SRDATFHYGE QAAKNNLKGR LHLESPSPGV   900
YRLFIQNVAV QDSGTYSCHV EEWLPSPSGM WYKRAEDTAG QTALTVMRPD ASLQVDTVVP   960
NATVSEKAAF QLDCSIVSRS SQDSRFAVAW YSLRTKAGGK RSSPGLEEQE EEREEEEEEE   1020
EDDDDDDPTE RTALLSVGPD AVFGPEGSPW EGRLRFQRLS PVLYRLTVLQ ASPQDTGNYS   1080
CHVEEWLPSP QKEWYRLTEE ESAPIGIRVL DTSPTLQSII CSNDALFYFV FFYPFPIFGI   1140
LIITILLVRF KSRNSSKNSD GKNGVPLLWI KEPHLNYSPT CLEPPVLSIH PGAID        1195

SEQ ID NO: 21           moltype = AA   length = 798
FEATURE                 Location/Qualifiers
source                  1..798
                        mol_type = protein
                        organism = Homo sapiens
SEQUENCE: 21
MNLQPIFWIG LISSVCCVFA QTDENRCLKA NAKSCGECIQ AGPNCGWCTN STFLQEGMPT   60
SARCDDLEAL KKKGCPPDDI ENPRGSKDIK KNKNVTNRSK GTAEKLKPED ITQIQPQQLV   120
LRLRSGEPQT FTLKFKRAED YPIDLYYLMD LSYSMKDDLE NVKSLGTDLM NEMRRITSDF   180
RIGFGSFVEK TVMPYISTTP AKLRNPCTSE QNCTSPFSYK NVLSLTNKGE VFNELVGKQR   240
ISGNLDSPEG GFDAIMQVAV CGSLIGWRNV TRLLVFSTDA GFHFAGDGKL GGIVLPNDGQ   300
CHLENNMYTM SHYYDYPSIA HLVQKLSENN IQTIFAVTEE FQPVYKELKN LIPKSAVGTL   360
SANSSNVIQL IIDAYNSLSS EVILENGKLS EGVTISYKSY CKNGVNGTGE NGRKCSNISI   420
GDEVQFEISI TSNKCPKKDS DSFKIRPLGF TEEVEVILQY ICECECQSEG IPESPKCHEG   480
NGTFECGACR CNEGRVGRHC ECSTDEVNSE DMDAYCRKEN SSEICSNNGE CVCGQCVCRK   540
RDNTNEIYSG KFCECDNFNC DRSNGLICGG NGVCKCRVCE CNPNYTGSAC DCSLDTSTCE   600
ASNGQICNGR GICECGVCKC TDPKFQGQTC EMCQTCLGVC AEHKECVQCR AFNKGEKKDT   660
CTQECSYFNI TKVESRDKLP QPVQPDPVSH CKEKDVDDCW FYFTYSVNGN NEVMVHVVEN   720
PECPTGPDII PIVAGVVAGI VLIGLALLLI WKLLMIIHDR REFAKFEKEK MNAKWDTGEN   780
PIYKSAVTTV VNPKYEGK                                                798
```

```
SEQ ID NO: 22            moltype = AA  length = 1032
FEATURE                  Location/Qualifiers
source                   1..1032
                         mol_type = protein
                         organism = Homo sapiens
SEQUENCE: 22
MAWEARREPG PRRAAVRETV MLLLCLGVPT GRPYNVDTES ALLYQGPHNT LFGYSVVLHS   60
HGANRWLLVG APTANWLANA SVINPGAIYR CRIGKNPGQT CEQLQLGSPN GEPCGKTCLE  120
ERDNQWLGVT LSRQPGENGS IVTCGHRWKN IFYIKNENKL PTGGCYGVPP DLRTELSKRI  180
APCYQDYVKK FGENFASCQA GISSSFYTKDL IVMGAPGSSY WTGSLFVYNI TTNKYKAFLD  240
KQNQVKFGSY LGYSVGAGHF RSQHTTEVVG GAPQHEQIGK AYIFSIDEKE LNILHEMKGK  300
KLGSYFGASV CAVDLNADGF SDLLVGAPMQ STIREEGRVF VYINSGSGAV MNAMETNLVG  360
SDKYAARFGE SIVNLGDIDN DGFEDVAIGA PQEDDLQGAI YIYNGRADGI SSTFSQRIEG  420
LQISKSLSMF GQSISGQIDA DNNGYVDVAV GAFRSDSAVL LRTRPVVIVD ASLSHPESVN  480
RTKFDCVENG WPSVCIDLTL CFSYKGKEVP GYIVLFYNMS LDVNRKAESP PRFYFSSNGT  540
SDVITGSIQV SSREANCRTH QAFMRKDVRD ILTPIQIEAA YHLGPHVISK RSTEEFPPLQ  600
PILQQKKEKD IMKKTINFAR FCAHENCSAD LQVSAKIGFL KPHENKTYLA VGSMKTLMLN  660
VSLFNAGDDA YETTLHVKLP VGLYFIKILE LEEKQINCEV TDNSGVVQLD CSIGYIYVDH  720
LSRIDISFLL DVSSLSRAEE DLSITVHATC ENEEEMDNLK HSRVTVAIPL KYEVKLTVHG  780
FVNPTSFVYG SNDENEPETC MVEKMNLTFH VINTGNSMAP NVSVEIMVPN SFSPQTDKLF  840
NILDVQTTTG ECHFENYQRV CALEQQKSAM QTLKGIVRFL SKTDKRLLYC IKADPHCLNF  900
LCNFGKMESG KEASVHIQLE GRPSILEMDE TSALKFEIRA TGFPPEPNPRV IELNKDENVA  960
HVLLEGLHHQ RPKRYFTIVI ISSSLLLGLI VLLLISYVMW KAGFFKRQYK SILQEENRRD  1020
SWSYINSKSN DD                                                     1032

SEQ ID NO: 23            moltype = AA  length = 661
FEATURE                  Location/Qualifiers
source                   1..661
                         mol_type = protein
                         organism = Homo sapiens
SEQUENCE: 23
MELQPPEASI AVVSIPRQLP GSHSEAGVQG LSAGDDSELG SHCVAQTGLE LLASGDPLPS   60
ASQNAEMIET GSDCVTQAGL QLLASSDPPA LASKNAEVTE TGFHHVSQAD IEFLTSIDPT  120
ASASGSAGIT GTMSQDTEVD MKEVELNELE PEKQPMNAAS GAAMSLAGAE KNGLVKIKVA  180
EDEAEAAAAA KFTGLSKEEL LKVAGSPGWV RTRWALLLLF WLGWLGMLAG AVVIIVRAPR  240
CRELPAQKWW HTGALYRIGD LQAFQGHGAG NLAGLKGRLD YLSSLKVKGL VLGPIHKNQK  300
DDVAQTDLLQ IDPNFGSKED FDSLLQSAKK KSIRVILDLT PNYRGENSWF STQVDTVATK  360
VKDALEFWLQ AGVDGFQVRD IENLKDASSF LAEWQNITKG FSEDRLLIAG TNSSDLQQIL  420
SLLESNKDLL LTSSYLSDSG STGEHTKSLV TQYLNATGNR WCSWSLSQAR LLTSFLPAQL  480
LRLYQLMLFT LPGTPVFSYG DEIGLDAAAL PGQPMEAPVM LWDESSFPDI PGAVSANMTV  540
KGQSEDPGSL LSLFRRLSDQ RSKERSLLHG DFHAFSAGPG LFSYIRHWDQ NERFLVVLNF  600
GDVGLSAGLQ ASDLPASASL PAKADLLLST QPGREEGSPL ELERLKLEPH EGLLLRFPYA  660
A                                                                  661

SEQ ID NO: 24            moltype = AA  length = 1023
FEATURE                  Location/Qualifiers
source                   1..1023
                         mol_type = protein
                         organism = Homo sapiens
SEQUENCE: 24
MGKGVGRDKY EPAAVSEQGD KKGKKGKKDR DMDELKKEVS MDDHKLSLDE LHRKYGTDLS   60
RGLTSARAAE ILARDGPNAL TPPPTTPEWI KFCRQLFGGF SMLLWIGAIL CFLAYSIQAA  120
TEEEPQNDNL YLGVVLSAVV IITGCFSYYQ EAKSSKIMES FKNMVPQQAL VIRNGEKMSI  180
NAEEVVVGDL VEVKGGDRIP ADLRIISANG CKVDNSSLTG ESEPQTRSPD FTNENPLETR  240
NIAFFSTNCV EGTARGIVVY TGDRTVMGRI ATLASGLEGG QTPIAAEIEH FIHIITGVAV  300
FLGVSFFILS LILEYTWLEA VIFLIGIIVA NVPEGLLATV TVCLTLTAKR MARKNCLVKN  360
LEAVETLGST STICSDKTGT LTQNRMTVAH MWFDNQIHEA DTTENQSGVS FDKTSATWLA  420
LSRIAGLCNR AVFQANQENL PILKRAVAGD ASESALLKCI ELCCGSVKEM RERYAKIVEI  480
PFNSTNKYQL SIHKNPNTSE PQHLLVMKGA PERILDRCSS ILLHGKEQPL DEELKDAFQN  540
AYLELGGLGE RVLGFCHLFL PDEQFPEGFQ FDTDDVNFPI DNLCFVGLIS MIDPPRAAVP  600
DAVGKCRSAG IKVIMVTGDH PITAKAIAKG VGIISEGNET VEDIAARLNI PVSQVNPRDA  660
KACVVHGSDL KDMTSEQLDD ILKYHTEIVF ARTSPQQKLI IVEGCQRQGA IVAVTGDGVN  720
DSPALKKADI GVAMGIAGSD VSKQAADMIL LDDNFASIVT GVEEGRLIFD NLKKSIAYTL  780
TSNIPEITPF LIFIIANIPL PLGTVTILCI DLGTDMVPAI SLAYEQAESD IMKRQPRNPK  840
TDKLVNERLI SMAYGQIGMI QALGGFFTYF VILAENGFLP IHLLGLRVDW DDRWINDVED  900
SYGQQWTYEQ RKIVEFTCHT AFFVSIVVVQ WADLVICKTR RNSVFQQGMK NKILIFGLFE  960
ETALAAFLSY CPGMGVALRM YPLKPTWWFC AFPYSLLIFV YDEVRKLIIR RPGGWVEKE  1020
TYY                                                               1023

SEQ ID NO: 25            moltype = AA  length = 1020
FEATURE                  Location/Qualifiers
source                   1..1020
                         mol_type = protein
                         organism = Homo sapiens
SEQUENCE: 25
MGRGAGREYS PAATTAENGG GKKKQKEKEL DERLKKEVAMD DHKLSLDELG RKYQVDLSKG   60
LTNQRAQDVL ARDGPNALTP PPTTPEWVKF CRQLFGGFSI LLWIGAILCF LAYGIQAAME  120
DEPSNDNLYL GVVLAAVVIV TGCFSYYQEA KSSKIMDSFK NMVPQQALVI REGEKMQINA  180
```

```
EEVVVGDLVE VKGGDRVPAD LRIISSHGCK VDNSSLTGES EPQTRSPEFT HENPLETRNI    240
CFFSTNCVEG TARGIVIATG DRTVMGRIAT LASGLEVGRT PIAMEIEHFI QLITGVAVFL    300
GVSFFVLSLI LGYSWLEAVI FLIGIIVANV PEGLLATVTV CLTLTAKRMA RKNCLVKNLE    360
AVETLGSTST ICSDKTGTLT QNRMTVAHMW FDNQIHEADT TEDQSGATFD KRSPTWTALS    420
RIAGLCNRAV FKAGQENISV SKRDTAGDAS ESALLKCIES SCGSVRKMRD RNPKVAEIPF    480
NSTNKYQLSI HEREDSPQSH VLVMKGAPER ILDRCSTILV QGKEIPLDKE MQDAFQNAYM    540
ELGGLGERVL GFCQLNLPSG KFPRGFKFDT DELNFPTEKL CFVGLMSMID PPRAAVPDAV    600
GKCRSAGIKV IMVTGDHPIT AKAIAKGVGI ISEGNETVED IAARLNIPMS QVNPREAKAC    660
VVHGSDLKDM TSEQLDEILK NHTEIVFART SPQQKLIIVK GCQRQGAIVA VTGDGVNDSP    720
ALKKADIGIA MGISGSDVSK QAADMILLDD NFASIVTGVE EGRLIFDNLK KSIAYTLTSN    780
IPEITPFLLF IIANIPLPLG TVTILCIDLG TDMVPAISLA YEAAESDIMK RQPRNSQTDK    840
LVNERLISMA YGQIGMIQAL GGFFTYFVIL AENGFLPSRL LGIRLDWDDR TMNDLEDSYG    900
QEWTYEQRKV VEFTCHTAFF ASIVVVQWAD LIICKTRRNS VFQQGMKNKI LIFGLLEETA    960
LAAFLSYCPG MGVALRMYPL KVTWWFCAFP YSLLIFIYDE VRKLILRRYP GGWVEKETYY   1020

SEQ ID NO: 26           moltype = AA   length = 1026
FEATURE                 Location/Qualifiers
source                  1..1026
                        mol_type = protein
                        organism = Homo sapiens
SEQUENCE: 26
MGSGGSDSYR IATSQDKKDD KDSPKKNKGK ERRDLDDLKK EVAMTEHKMS VEEVCRKYNT     60
DCVQGLTHSK AQEILARDGP NALTPPPTTP EWVKFCRQLF GGFSILLWIG AILCFLAYGI    120
QAGTEDDPSG DNLYLGIVLA AVVIITGCFS YYQEAKSSKI MESFKNMVPQ QALVIREGEK    180
MQVNAEEVVV GDLVEIKGGD RVPADLRIIS AHGCKVDNSS LTGESEPQTR SPDCTHDNPL    240
ETRNITFFST NCVEGTARGV VVATGDRTVM GRIATLASGL EVGKTPIAIE IEHFIQLITG    300
VAVFLGVSFF ILSLILGYTW LEAVIFLIGI IVANVPEGLL ATVTVCLTLT AKRMARKNCL    360
VKNLEAVETL GSTSTICSDK TGTLTQNRMT VAHMWFDNQI HEADTTEDQS GTSFDKSSHT    420
WVALSHIAGL CNRAVFKGGQ DNIPVLKRDV AGDASESALL KCIELSSGSV KLMRERNKKV    480
AEIPFNSTNK YQLSIHETED PNDNRYLLVM KGAPERILDR CSTILLQGKE QPLDEEMKEA    540
FQNAYLELGG LGERVLGFCH YYLPEEQFPK GFAFDCDDVN FTTDNLCFVG LMSMIDPPRA    600
AVPDAVGKCR SAGIKVIMVT GDHPITAKAI AKGVGIISEG NETVEDIAAR LNIPVSQVNP    660
RDAKACVIHG TDLKDFTSEQ IDEILQNHTE IVFARTSPQQ KLIIVEGCQR QGAIVAVTGD    720
GVNDSPALKK ADIGVAMGIA GSDVSKQAAD MILLDDNFAS IVTGVEEGRL IFDNLKKSIA    780
YTLTSNIPEI TPFLLFIMAN IPLPLGTITI LCIDLGTDMV PAISLAYEAA ESDIMKRQPR    840
NPRTDKLVNE RLISMAYGQI GMIQALGGFF SYFVILAENG FLPGNLVGIR LNWDDRTVND    900
LEDSYGQQWT YEQRKVVEFT CHTAFFVSIV VVQWADLIIC KTRRNSVFQQ GMKNKILIFG    960
LFEETALAAF LSYCPGMDVA LRMYPLKPSW WFCAFPYSFL IFVYDEIRKL ILRRNPGGWV   1020
EKETYY                                                              1026

SEQ ID NO: 27           moltype = AA   length = 1029
FEATURE                 Location/Qualifiers
source                  1..1029
                        mol_type = protein
                        organism = Homo sapiens
SEQUENCE: 27
MGLWGKKGTV APHDQSPRRR PKKGLIKKKM VKREKQKRNM EELKKEVVMD DHKLTLEELS     60
TKYSVDLTKG HSHQRAKEIL TRGGPNTVTP PPTPEWVKF CKQLFGGFSL LLWTGAILCF    120
VAYSIQIYFN EEPTKDNLYL SIVLSVVVIV TGCFSYYQEA KSSKIMESFK NMVPQQALVI    180
RGGEKMQINV QEVVLGDLVE IKGGDRVPAD LRLISAQGCK VDNSSLTGES EPQSRSPDFT    240
HENPLETRNI CFFSTNCVEG TARGIVIATG DSTVMGRIAS LTSGLAVGQT PIAAEIEHFI    300
HLITVVAVFL GVTFFALSLL LGYGWLEAII FLIGIIVANV PEGLLATVTV CLTLTAKRMA    360
RKNCLVKNLE AVETLGSTST ICSDKTGTLT QNRMTVAHMW FDNQIMTVYEADT TEEQTGKTFT    420
KSSDTWFMLA RIAGLCNRAD FKANQEILPI AKRATTGDAS ESALLKFIEQ SYSSSVAEMRE    480
KNPKVAEIPF NSTNKYQMSI HLREDSSQTH VLMMKGAPER ILEFCSTFLL NGQEYSMNDE    540
MKEAFQNAYL ELGGLGERVL GFCFLNPSS FSKGFPFNTD EINFPMDNLC FVGLISMIDP    600
PRAAVPDAVS KCRSAGIKVI MVTGDHPITA KAIAKGVGII SEGTETAEEV AARLKIPISK    660
VDASAAKAIV VHGAELKDIQ SKQLDQILQN HPEIVFARTS PQQKLIIVEG CQRLGAVVAV    720
TGDGVNDSPA LKKADIGIAM GISGSDVSKQ AADMILLDDN FASIVTGVEE GRLIFDNLKK    780
SIMYTLTSNI PEITPFLMFI ILGIPLPLGT ITILCIDLGT DMVPAISLAY ESAESDIMKR    840
LPRNPKTDNL VNHRLIGMAY GQIGMIQALA GFFTYFVILA ENGFRPVDLL GIRLHWEDKY    900
LNDLEDSYGQ QWTYEQRKVV EFTCQTAFFV TIVVVQWADL IISKTRRNSL FQQGMRNKVL    960
IFGILEETLL AAFLSYTPGM DVALRMYPLK ITWWLCAIPY SILIFVYDEI RKLLIRQHPD   1020
GWVERETYY                                                          1029

SEQ ID NO: 28           moltype = AA   length = 279
FEATURE                 Location/Qualifiers
source                  1..279
                        mol_type = protein
                        organism = Homo sapiens
SEQUENCE: 28
MTKNEKKSLN QSLAEWKLFI YNPTTGEFLG RTAKSWGLIL LFYLVFYGFL AALFSFTMWV     60
MLQTLNDEVP KYRDQIPSPG LMVFPKPVTA LEYTFSRSDP TSYAGYIEDL KKFLKPYTLE    120
EQKNLTVCPD GALFEQKGPV YVACQFPISL LQACSGMNDP DFGYSQGNPC ILVKMNRIIG    180
LKPEGVPRID CVSKNEDIPN VAVYPHNGMI DLKYFPYYGK KLHVGYLQPL VAVQVSFAPN    240
NTGKEVTVEC KIDGSANLKS QDDRKFLGR VMFKITARA                           279

SEQ ID NO: 29           moltype = AA   length = 1258
FEATURE                 Location/Qualifiers
```

| source | 1..1258 |
| --- | --- |
| | mol_type = protein |
| | organism = Homo sapiens |

SEQUENCE: 29

```
MGDMANNSVA YSGVKNSLKE ANHDGDFGIT LAELRALMEL RSTDALRKIQ ESYGDVYGIC  60
TKLKTSPNEG LSGNPADLER REAVFGKNFI PPKKPKTFLQ LVWEALQDVT LIILEIAAIV  120
SLGLSFYQPP EGDNALCGEV SVGEEEGEGE TGWIEGAAIL LSVVCVVLVT AFNDWSKEKQ  180
FRGLQSRIEQ EQKFTVIRGG QVIQIPVADI TVGDIAQVKY GDLLPADGIL IQGNDLKIDE  240
SSLTGESDHV KKSLDKDPLL LSGTHVMEGS GRMVVTAVGV NSQTGIIFTL LGAGGEEEEK  300
KDEKKKEKKN KKQDGAIENR NKAKAQDGAA MEMQPLKSEE GGDGDEKDKK KANLPKKEKS  360
VLQGKLTKLA VQIGKAGLLM SAITVIILVL YFVIDTFWVQ KRPWLAECTP IYIQYFVKFF  420
IIGVTVLVVA VPEGLPLAVT ISLAYSVKKM MKDNNLVRHL DACETMGNAT AICSDKTGTL  480
TMNRMTVVQA YINEKHYKKV PEPEAIPPNI LSYLVTGISV NCAYTSKILP PEKEGGLPRH  540
VGNKTECALL GLLLDLKRDY QDVRNEIPEE ALYKVYTFNS VRKSMSTVLK NSDGSYRIFS  600
KGASEIILKK CFKILSANGE AKVFRPRDRD DIVKTVIEPM ASEGLRTICL AFRDFPAGEP  660
EPEWDNENDI VTGLTCIAVV GIEDPVRPEV PDAIKKCQRA GITVRMVTGD NINTARAIAT  720
KCGILHPGED FLCLEGKDFN RRIRNEKGEI EQERIDKIWP KLRVLARSSP TDKHTLVKGI  780
IDSTVSDQRQ VVAVTGDGTN DGPALKKADV GFAMGIAGTD VAKEASDIIL TDDNFTSIVK  840
AVMWGRNVYD SISKFLQFQL TVNVVAVIVA FTGACITQDS PLKAVQMLWV NLIMDTLASL  900
ALATEPPTES LLLRKPYGRN KPLISRTMMK NILGHAFYQL VVVFTLLFAG EKFFDIDSGR  960
NAPLHAPPSE HYTIVFNTFV LMQLFNEINA RKIHGERNVF EGIFNNAIFC TIVLGTFVVQ  1020
IIIVQFGGKP FSCSELSIEQ WLWSIFLGMG TLLWGQLIST IPTSRLKFLK EAGHGTQKEE  1080
IPEEELAEDV EEIDHAEREL RRGQILWFRG LNRIQTQMDV VNAFQSGSSI QGALRRQPSI  1140
ASQHHDVTNI STPTHIRVVN AFRSSLYEGL EKPESRSSIH NFMTHPEFRI EDSEPHIPLI  1200
DDTDAEDDAP TKRNSSPPPS PNKNNNAVDS GIHLTIEMNK SATSSSPGSP LHSLETSL   1258
```

| SEQ ID NO: 30 | moltype = AA length = 1272 |
| --- | --- |
| FEATURE | Location/Qualifiers |
| source | 1..1272 |
| | mol_type = protein |
| | organism = Homo sapiens |

SEQUENCE: 30

```
MGDMTNSDFY SKNQRNESSH GGEFGCTMEE LRSLMELRGT EAVVKIKETY GDTEAICRRL  60
KTSPVEGLPG TAPDLEKRKQ IFGQNFIPPK KPKTFLQLVW EALQDVTLII LEIAAIISLG  120
LSFYHPPGEG NEGCATAQGG AEDEGEAEAG WIEGAAILLS VICVVLVTAF NDWSKEKQFR  180
GLQSRIEQEQ KFTVVRAGQV VQIPVAEIVV GDIAQVKYGD LLPADGLFIQ GNDLKIDESS  240
LTGESDQVRK SVDKDPMLLS GTHVMEGSGR MLVTAVGVNS QTGIIFTLLG AGGEEEEKKD  300
KKGVKKGDGL QLPAADGAAA SNAADSANAS LVNGKMQDGN VDASQSKAKQ QDGAAAMEMQ  360
PLKSAEGGDA DDRRKASMHK KEKSVLQGKL TKLAVQIGKA GLVMSAITVI ILVLYFTVDT  420
FVVNKKPWLP ECTPVYQYF VKFFIIGVTV LVVAVPEGLP LAVTISLAYS VKKMMKDNNL  480
VRHLDACETM GNATAICSDK TGTLTTNRMT VVQAYVGDVH YKEIPDPSSI NTKTMELLIN  540
AIAINSAYTT KILPPEKEGA LPRQVGNKTE CGLLGFVLDL KQDYEPVRSQ MPEEKLYKVY  600
TFNSVRKSMS TVIKLPDESF RMYSKGASEI VLKKCCKILN GAGEPRVFRP RDRDEMVKKV  660
IEPMACDGLR TICVAYRDFP SSPEPDWDNE NDILNELTCI CVVGIEDPVR PEVPEAIRKC  720
QRAGITVRMV TGDNINTARA IAIKCGIIHP GEDFLCLEGK EFNRRIRNEK GEIEQERIDK  780
IWPKLRVLAR SSPTDKHTLV KGIIDSTHTE QRQVVAVTGD GTNDGPALKK ADVGFAMGIA  840
GTDVAKEASD IILTDDNFSS IVKAVMWGRN VYDSISKFLQ FQLTVNVVAV IVAFTGACIT  900
QDSPLKAVQM LWVNLIMDTF ASLALATEPP TETLLLRKPY GRNKPLISRT MMKNILGHAV  960
YQLALIFTLL FVGEKMFQID SGRNAPLHSP PSEHYTIIFN TFVMMQLFNE INARKIHGER  1020
NVFDGIFRNP IFCTIVLGTF AIQIVIVQFG GKPFSCSPLQ LDQWMWCIFI GLGELVWGQV  1080
IATIPTSRLK FLKEAGRLTQ KEEIPEEELN EDVEEIDHAE RELRRGQILW FRGLNRIQTQ  1140
IEVVNTFKSG ASFQGALRRQ SSVTSQSQDI RVVKAFRSSL YEGLEKPESR TSIHNFMAHP  1200
EFRIEDSQPH IPLIDDTDLE EDAALKQNSS PPSSLNKNNS AIDSGINLTT DTSKSATSSS  1260
PGSPIHSLET SL                                                     1272
```

| SEQ ID NO: 31 | moltype = AA length = 874 |
| --- | --- |
| FEATURE | Location/Qualifiers |
| source | 1..874 |
| | mol_type = protein |
| | organism = Homo sapiens |

SEQUENCE: 31

```
MGDMANSSIE FHPKPQQQRD VPQAGGFGCT LAELRTLMEL RGAEALQKIE EAYGDVSGLC  60
RRLKTSPTEG LADNTNDLEK RRQIYGQNFI PPKQPKTFLQ LVWEALQDVT LIILEVAAIV  120
SLGLSFYAPP GEESEACGNV SGGAEDEGEA EAGWIEGAAI LLSVICVVLV TAFNDWSKEK  180
QFRGLQSRIE QEQKFTVIRN GQLLQVPVAA LVVGDIAQVK YGDLLPADGV LIQANDLKID  240
ESSLTGESDH VRKSADKDPM LLSGTHVMEG SGRMVVTAVG VNSQTGIIFT LLGAGGEEEE  300
KKDKKGKQQD GAMESSQTKA KKQDGAVAME MQPLKSAEGG EMEERRKKKA NAPKKEKSVL  360
QGKLTKLAVQ IGKAGLVMSA ITVIILVLYF VIETFVVEGR TWLAECTPVY VQYFVKFFII  420
GVTVLVVAVP EGLPLAVTIS LAYSVKKMMK DNNLVRHLDA CETMGNATAI CSDKTGTLTT  480
NRMTVVQSYL GDTHYKEIPA PSALTPKILD LLVHAISINS AYTTKILPPE KEGALPRQVG  540
NKTECALLGF VLDLKRDFQP VREQIPEDKL YKVYTFNSVR KSMSTVIRMP DGGFRLFSKG  600
ASEILLKKCT NILNSNGELR GFRPRDRDDM VRKIIEPMAC DGLRTICIAY RDFSAGQEPD  660
WDNENEVVGD LTCIAVVGIE DPVRPEVPEA IRKCQRAGIT VRMVTGDNIN TARAIAAKCG  720
IIQPGEDFLC LEGKEFNRRI RNEKGEIEQE RLDKVWPKLR VLARSSPTDK HTLVKGIIDS  780
TTGEQRQVVA VTGDGTNDGP ALKKADVGFA MGIAGTDVAK EASDIILTDD NFTSIVKAVM  840
WGRNVYDSIS KFLQFQLTVN VVAVIVAFTG ACIT                              874
```

| SEQ ID NO: 32 | moltype = AA length = 1241 |
| --- | --- |
| FEATURE | Location/Qualifiers |

| | | |
|---|---|---|
| source | 1..1241<br>mol_type = protein<br>organism = Homo sapiens | |
| SEQUENCE: 32 | | |
| MTNPSDRVLP ANSMAESREG DFGCTVMELR KLMELRSRDA LTQINVHYGG VQNLCSRLKT | | 60 |
| SPVEGLSGNP ADLEKRRQVF GHNVIPPKKP KTFLELVWEA LQDVTLIILE IAAIISLVLS | | 120 |
| FYRPAGEENE LCGQVATTPE DENEAQAGWI EGAAILFSVI IVVLVTAFND WSKEKQFRGL | | 180 |
| QCRIEQEQKF SIIRNGQLIQ LPVAEIVVGD IAQVKYGDLL PADGILIQGN DLKIDESSLT | | 240 |
| GESDHVKKSL DKDPMLLSGT HVMEGSGRMV VTAVGVNSQT GIILTLLGVN EDDEGEKKKK | | 300 |
| GKKQGVPENR NKAKTQDGVA LEIQPLNSQE GIDNEEKDKK AVKVPKKEKS VLQGKLTRLA | | 360 |
| VQIGKAGLLM SALTVFILIL YFVIDNFVIN RRPWLPECTP IYIQYFVKFF IIGITVLVVA | | 420 |
| VPEGLPLAVT ISLAYSVKKM MKDNNLVRHL DACETMGNAT AICSDKTGTL TMNRMTVVQA | | 480 |
| YIGGIHYRQI PSPDVFLPKV LDLIVNGISI NSAYTSKILP PEKEGGLPRQ VGNKTECALL | | 540 |
| GFVTDLKQDY QAVRNEVPEE KLYKVYTFNS VRKSMSTVIR NPNGGFRMYS KGASEIILRK | | 600 |
| CNRILDRKGE AVPFKNKDRD DMVRTVIEPM ACDGLRTICI AYRDFDDTEP SWDNENEILT | | 660 |
| ELTCIAVVGI EDPVRPEVPD AIAKCKQAGI TVRMVTGDNI NTARAIATKC GILTPGDDFL | | 720 |
| CLEGKEFNRL IRNEKGEVEQ EKLDKIWPKL RVLARSSPTD KHTLVKGIID STVGEHRQVV | | 780 |
| AVTGDGTNDG PALKKADVGF AMGIAGTDVA KEASDIILTD DNFTSIVKAV MWGRNVYDSI | | 840 |
| SKFLQFQLTV NVVAVIVAFT GACITQDSPL KAVQMLWVNL IMDTFASLAL ATEPPTESLL | | 900 |
| KRRPYGRNKP LISRTMMKNI LGHAFYQLIV IFILVFAGEK FFDIDSGRKA PLHSPPSQHY | | 960 |
| TIVFNTFVLM QLFNEINSRK IHGEKNVFSG IYRNIIFCSV VLGTFICQIF IVEFGGKPFS | | 1020 |
| CTSLSLSQWL WCLFIGIGEL LWGQFISAIP TRSLKFLKEA GHGTTKEEIT KDAEGLDEID | | 1080 |
| HAEMELRRGQ ILWFRGLNRI QTQIDVINTF QTGASFKGVL RRQNMGQHLD VKLVPSSSYI | | 1140 |
| KVVKAFHSSL HESIQKPYNQ KSIHSFMTHP EFAIEEELPR TPLLDEEEEE NPDKASKFGT | | 1200 |
| RVLLLDGEVT PYANTNNNAV DCNQVQLPQS DSSLQSLETS V | | 1241 |
| | | |
| SEQ ID NO: 33<br>FEATURE<br>source | moltype = AA   length = 193<br>Location/Qualifiers<br>1..193<br>mol_type = protein<br>organism = Homo sapiens | |
| SEQUENCE: 33 | | |
| GPIFNASVHS DTPSVIRGDL IKLFCIITVE GAALDPDDMA FDVSWFAVHS FGLDKAPVLL | | 60 |
| SSLDRKGIVT TSRRDWKSDL SLERVSVLEF LLQVHGSEDQ DFGNYYCSVT PWVKSPTGSW | | 120 |
| QKEAEIHSKP VFITVKMDVL NAFKYPLLIG VGLSTVIGLL SCLIGYCSSH WCCKKEVQET | | 180 |
| RRERRRLMSM EMD | | 193 |
| | | |
| SEQ ID NO: 34<br>FEATURE<br>source | moltype = AA   length = 1021<br>Location/Qualifiers<br>1..1021<br>mol_type = protein<br>organism = Homo sapiens | |
| SEQUENCE: 34 | | |
| MAGISYVASF FLLLTKLSIG QREVTVQKGP LFRAEGYPVS IGCNVTGHQG PSEQHFQWSV | | 60 |
| YLPTNPTQEV QIISTKDAAF SYAVYTQRVR SGDVYVERVQ GNSVLHISEK LQMKDAGEYE | | 120 |
| CHTPNTDEKY YGSYSAKTNL IVIPDTLSAT MSSQTLGKEE GEPLALTCEA SKATAQHTHL | | 180 |
| SVTWYLTQDG GGSQATEIIS LSKDFILVPG PLYTERFAAS DVQLNKLGPT TFRLSIERLQ | | 240 |
| SSDQGQLFCE ATEWIQDPDE TWMFITKKQT DQTTLRIQPA VKDFQVNITA DSLFAEGKPL | | 300 |
| ELVCLVVSSG RDPQLQGIWF FNGTEIAHID AGGVLGLKND YKERASQGEL QVSKLGKPAF | | 360 |
| SLKIFSLGPE DEGAYRCVVA EVMKTRTGSW QVLRKQSPD SHVHLRKPAA RSVVMSTKNK | | 420 |
| QQVVWEGETL AFLCKAGGAE SPLSVSWWHI PRDQTQPEFV AGMGQDGIVQ LGASYGPSY | | 480 |
| HGNTRLEKMD WATFQLEITF TAITDSGTYE CRVSEKSRNQ ARDLSWTQKI SVTVKSLESS | | 540 |
| LQVSLMSRQP QVMLTNTFDL SCVVRAGYSD LKVPLTVTWQ FQPASSHIFH QLIRITHNGT | | 600 |
| IEWGNFLSRF QKKTKVSQSL FRSQLLVHDA TEEETGVYQC EVEVYDRNSL YNNRPPRASA | | 660 |
| ISHPLRIAVT LPESKLKVNS RSQVQELSIN SNTDIECSIL SRSNGNLQLA IIWYFSPVST | | 720 |
| NASWLKILEM DQTNVIKTGD EFHTPQRKQK FHTEKVSQDL FQLHILNVED SDRGKYHCAV | | 780 |
| EEWLLSTNGT WHKLGEKKSG LTELKLKPTG SKVRVSKVYW TENVTEHREV AIRCSLESVG | | 840 |
| SSATLYSVMW YWNRENSGSK LLVHLQHDGL LEYGEEGLRR HLHCYRSSST DFVLKLHQVE | | 900 |
| MEDAGMYWCR VAEWQLHGHP SKWINQASDE SQRMVLTVLP SEPTLPSRIC SSAPLLYFLF | | 960 |
| ICPFVLLLLL LISLLCLYWK ARKLSTLRSN TRKEKALWVD LKEAGGVTTN RREDEEEDEG | | 1020 |
| N | | 1021 |
| | | |
| SEQ ID NO: 35<br>FEATURE<br>source | moltype = AA   length = 20<br>Location/Qualifiers<br>1..20<br>mol_type = protein<br>organism = Homo sapiens | |
| SEQUENCE: 35 | | |
| MAGISYVASF FLLLTKLSIG | | 20 |
| | | |
| SEQ ID NO: 36<br>FEATURE<br>misc_feature | moltype = DNA   length = 20<br>Location/Qualifiers<br>1..20<br>note = Description of Artificial Sequence:<br>Syntheticoligonucleotide | |
| source | 1..20<br>mol_type = other DNA<br>organism = synthetic construct | |
| SEQUENCE: 36 | | |

```
cgttggcagt ccgccttaac                                                    20

SEQ ID NO: 37          moltype = DNA   length = 20
FEATURE                Location/Qualifiers
misc_feature           1..20
                       note = Description of Artificial Sequence:
                       Syntheticoligonucleotide
source                 1..20
                       mol_type = other DNA
                       organism = synthetic construct
SEQUENCE: 37
catagtcact gacgttgcag                                                    20

SEQ ID NO: 38          moltype = DNA   length = 20
FEATURE                Location/Qualifiers
misc_feature           1..20
                       note = Description of Artificial Sequence:
                       Syntheticoligonucleotide
source                 1..20
                       mol_type = other DNA
                       organism = synthetic construct
SEQUENCE: 38
ttgtggagct tgcaagcacc                                                    20

SEQ ID NO: 39          moltype = DNA   length = 20
FEATURE                Location/Qualifiers
misc_feature           1..20
                       note = Description of Artificial Sequence:
                       Syntheticoligonucleotide
source                 1..20
                       mol_type = other DNA
                       organism = synthetic construct
SEQUENCE: 39
gttctttatg tggagctcca                                                    20

SEQ ID NO: 40          moltype = DNA   length = 20
FEATURE                Location/Qualifiers
misc_feature           1..20
                       note = Description of Artificial Sequence:
                       Syntheticoligonucleotide
source                 1..20
                       mol_type = other DNA
                       organism = synthetic construct
SEQUENCE: 40
tatcccttgc tgatcggcgt                                                    20

SEQ ID NO: 41          moltype = DNA   length = 20
FEATURE                Location/Qualifiers
misc_feature           1..20
                       note = Description of Artificial Sequence:
                       Syntheticoligonucleotide
source                 1..20
                       mol_type = other DNA
                       organism = synthetic construct
SEQUENCE: 41
gctgcagtac ccgatgagac                                                    20

SEQ ID NO: 42          moltype = AA    length = 38
FEATURE                Location/Qualifiers
REGION                 1..38
                       note = Description of Artificial Sequence:
                       Syntheticpolypeptide
source                 1..38
                       mol_type = protein
                       organism = synthetic construct
SEQUENCE: 42
EHSAGGGGSD YKDDDDKGGG GSLSNPIEID FQTSGPIF                                 38

SEQ ID NO: 43          moltype = AA    length = 34
FEATURE                Location/Qualifiers
REGION                 1..34
                       note = Description of Artificial Sequence:
                       Syntheticpolypeptide
source                 1..34
                       mol_type = protein
                       organism = synthetic construct
SEQUENCE: 43
EHSAGGGGSD YKDDDDKGGG GSIEIDFQTS GPIF                                     34
```

```
SEQ ID NO: 44              moltype = AA  length = 30
FEATURE                    Location/Qualifiers
REGION                     1..30
                           note = Description of Artificial Sequence:
                           Syntheticpolypeptide
source                     1..30
                           mol_type = protein
                           organism = synthetic construct
SEQUENCE: 44
EHSAGGGGSD YKDDDDKGGG GSFQTSGPIF                                      30

SEQ ID NO: 45              moltype = AA  length = 26
FEATURE                    Location/Qualifiers
REGION                     1..26
                           note = Description of Artificial Sequence: Syntheticpeptide
source                     1..26
                           mol_type = protein
                           organism = synthetic construct
SEQUENCE: 45
EHSAGGGGSD YKDDDDKGGG GSGPIF                                          26

SEQ ID NO: 46              moltype = AA  length = 42
FEATURE                    Location/Qualifiers
REGION                     1..42
                           note = Description of Artificial Sequence:
                           Syntheticpolypeptide
source                     1..42
                           mol_type = protein
                           organism = synthetic construct
SEQUENCE: 46
FITVKMDTLD PRSFLLRNPN DKYEPFWEDE EKNESGSDKT HT                        42
```

PREPARATION OF THERAPEUTIC EXOSOMES USING MEMBRANE PROTEINS

1. CROSS REFERENCE TO RELATED APPLICATIONS

This application is a division of U.S. application Ser. No. 16/722,884, filed Dec. 20, 2019, which is a continuation of U.S. application Ser. No. 16/231,012, filed Dec. 21, 2018 (now U.S. Pat. No. 10,561,740, issued on Feb. 18, 2020), which is a continuation of U.S. application Ser. No. 16/112,547, filed Aug. 24, 2018 (now U.S. Pat. No. 10,195,290, issued on Feb. 5, 2019), which claims the benefit of U.S. Provisional Application Nos. 62/656,956, filed Apr. 12, 2018, and 62/550,543, filed Aug. 25, 2017, each of which is hereby incorporated by reference in its entirety.

2. REFERENCE TO SEQUENCE LISTING SUBMITTED ELECTRONICALLY VIA EFS-WEB

The content of the electronically submitted sequence listing in XML format (Name: 0132-0249US4_SeqListing_ST26.xml; Size: 65,536 bytes; and Date of Creation: Aug. 25, 2023) filed with the application is herein incorporated by reference in its entirety.

3. BACKGROUND

Exosomes are important mediators of intercellular communication. They are also important biomarkers in the diagnosis and prognosis of many diseases, such as cancer. As drug delivery vehicles, exosomes offer many advantages over traditional drug delivery methods as a new treatment modality in many therapeutic areas.

The use of exosomes for therapeutic purposes requires that exosomes be free or mostly free of impurities including but not limited to contaminant proteins, DNA, carbohydrates, and lipids. Current purification methods do not offer sufficient selectivity to remove significant amounts of these impurities so additional processes are desired to improve purity.

Furthermore, as exosomes become more frequently used in the treatment of human disease, they may struggle to meet clinical expectations because of heterogeneity in their physicochemical parameters that confer molecular targeting, immune evasion, and controlled drug release. This is mainly due to the heterogeneity and complexity of exosome properties (e.g., composition, size, shape, rigidity, surface charge, hydrophilicity, stability, and ligand type and density), payload properties (e.g., drug type, solubility, loading, potency, dosing, immune response, and release kinetics), and in vivo physiological barriers to exosome trafficking (e.g., immune surveillance, particle extravasation, tissue targeting, tissue penetration, and cellular uptake). Although a considerable amount of effort has been made, effective methods for obtaining discrete sub-populations of therapeutic exosomes with desired properties, e.g., exosomes containing therapeutic payloads and having appropriate targeting moieties, are not yet readily available.

Suitable methods for generating, isolating and purifying discrete sub-populations of exosomes are needed to better enable therapeutic use and other applications of exosome-based technologies.

4. SUMMARY

An aspect of the present invention relates to novel methods of preparing exosomes for therapeutic use. Specifically, the methods use surface markers that are newly identified to be enriched on the surface of exosomes. In particular, a group of proteins (e.g., prostaglandin F2 receptor negative regulator (PTGFRN); basigin (BSG); immunoglobulin superfamily member 2 (IGSF2); immunoglobulin superfamily member 3 (IGSF3); immunoglobulin superfamily member 8 (IGSF8); integrin beta-1 (ITGB1); integrin alpha-4 (ITGA4); 4F2 cell-surface antigen heavy chain (SLC3A2); and a class of ATP transporter proteins (ATP1A1, ATP1A2, ATP1A3, ATP1A4, ATP1B3, ATP2B1, ATP2B2, ATP2B3, ATP2B4)) were identified to be highly enriched on the surface of exosomes.

The newly-identified proteins can be used in various embodiments of the present invention. One aspect of the present invention relates to generating a fusion protein by conjugating the newly-identified exosome protein and a therapeutic protein, and producing an engineered exosome containing the fusion protein on the surface. A native full-length or a biologically active fragment of the therapeutic protein can be transported to the surface of exosomes by being conjugated to the exosome-enriched proteins. The method using the newly-identified exosome proteins as provided herein are better at producing surface engineered exosomes than methods using some other exosome scaffold protein known in the art (e.g., Lamp2B, PDGFR, lactadherin CD9, CD63 and/or CD81, or fragments thereof). Without wishing to be bound by a theory, it is believed that the newly-identified proteins are better because several of the exosome scaffold proteins known in the art—i.e., tetraspannin proteins such as CD9, CD63 and CD81, have both of their C- and N-termini in the exosome lumen.

Another aspect of the present invention relates to purification of an exosome by affinity purification from a heterogeneous solution such as cell culture media or plasma using the exosome proteins that are common to all exosomes, or common to all exosomes derived from a single cell type. Some embodiments relate to isolation of a sub-population of exosomes from the total exosomes by using surface markers specific to a sub-population of exosomes.

Another aspect of the present invention relates to methods of removing exosomes from a sample when exosomes are a contaminating product. For example, natural or engineered viruses may be purified from contaminating exosomes. The exosome proteins described herein thus can be used to selectively remove exosomes from biological processes where other particles of similar size, shape, and/or charge are the desirable product.

Another aspect of the present invention relates to generation or use of a surface-engineered exosome designed for more efficient affinity purification, or for presentation of a targeting moiety or a therapeutically relevant protein on the surface. For example, the exosome surfaces can be modified to contain the native full-length exosome protein and/or a fragment or a modified protein of the native exosome protein on the surface at a higher density.

The present invention further relates to a producer cell or a method of generating the producer cell for producing such a surface-engineered exosome. An exogenous polynucleotide can be introduced transiently or stably into a producer cell to make the producer cell to generate a surface-engineered exosome.

Specifically, an aspect of the present invention relates to a method of isolating an exosome, comprising the steps of: (1) providing a sample comprising the exosome; (2) contacting the sample with a binding agent having affinity to a target protein, wherein the target protein comprises PTGFRN, BSG, IGSF2, IGSF3, IGSF8, ITGB1, ITGA4, SLC3A2, ATP transporter or a fragment or a variant thereof; and (3) isolating the exosome based on a binding between the target protein and the binding agent.

In some embodiments, the sample is obtained from a cell grown in vitro, optionally wherein the cell is an HEK293 cell, a Chinese hamster ovary (CHO) cell, or a mesenchymal stem cell (MSC). In some embodiments, the sample is obtained from a body fluid of a subject.

In some embodiments, the cell is genetically modified to express the target protein. In some embodiments, the cell comprises an expression plasmid encoding the target protein. In some embodiments, the cell is genetically modified to comprise an exogenous sequence expressing a tag having affinity to the binding agent, wherein the exogenous sequence is inserted into a genome of the cell. In some embodiments, the exogenous sequence is inserted in a genomic site located at 3' or 5' end of an endogenous sequence encoding PTGFRN, BSG, IGSF2, IGSF3, IGSF8, ITGB1, ITGA4, SLC3A2 or ATP transporter. In some embodiments, the endogenous sequence does not encode IGSF8. In some embodiments, the exogenous sequence is inserted in a genomic site located within an endogenous sequence encoding PTGFRN, BSG, IGSF3, IGSF8, ITGB1, ITGA4, SLC3A2 or ATP transporter.

In some embodiments, the target protein is a fusion protein comprising the tag, and PTGFRN, BSG, IGSF2, IGSF3, IGSF8, ITGB1, ITGA4, SLC3A2, ATP transporter or a fragment or a variant thereof. In some embodiments, the exosome comprises the target protein. In some embodiments, the target protein is not IGSF8 or a fragment or modification thereof. In some embodiments, the cell is genetically modified to have a reduced expression of ADAM10.

In some embodiments, the exosome comprises the target protein. In some embodiments, the target protein is selected from PTGFRN, BSG, IGSF2, IGSF3, ITGB1, ITGA4, SLC3A2 and ATP transporter. In some embodiments, the target protein comprises a fragment or a variant of PTGFRN, BSG, IGSF2, IGSF3, IGSF8, ITGB1, ITGA4, SLC3A2 or ATP transporter. In some embodiments, the target protein comprises a polypeptide of SEQ ID NO: 33. In some embodiments, the target protein is a fusion protein comprising PTGFRN, BSG, IGSF2, IGSF3, ITGB1, ITGA4, SLC3A2, ATP transporter or a fragment or a variant thereof, and an affinity tag, wherein the affinity tag has affinity to the binding agent. In some embodiments, the target protein does not comprise IGSF8 or a fragment or modification thereof.

In some embodiments, the binding agent comprises an immunoglobulin, a protein, a peptide, or a small molecule. In some embodiments, the binding agent is attached to a solid support, optionally wherein the solid support comprises a porous agarose bead, a microtiter plate, a magnetic bead, or a membrane.

In some embodiments, the solid support forms a chromatography column. In some embodiments, the step of contacting the sample with the binding agent is performed by applying the sample to the chromatography column.

In some embodiments, the method further comprises the steps of: (1) contacting a subset of the sample with a different binding agent having affinity to a different target protein; and (2) isolating the exosome based on a binding between the different target protein and the different binding agent. In some embodiments, the different target protein comprises PTGFRN, BSG, IGSF2, IGSF3, IGSF8, ATP transporter or a fragment or a variant thereof. In some embodiments, the different target protein comprises a polypeptide of SEQ ID NO: 33.

Another aspect of the present invention relates to an exosome produced by the methods provided herein.

In yet another aspect, the present invention relates to a pharmaceutical composition comprising the exosome of the present invention and an excipient. In some embodiments, the pharmaceutical composition comprises a lower concentration of macromolecules than the sample comprising the exosome source, wherein the macromolecules are nucleic acids, contaminant proteins, lipids, carbohydrates, metabolites, or a combination thereof. In some embodiments, the pharmaceutical composition is substantially free of the macromolecules.

Another aspect of the present invention relates to an exosome comprising a target protein wherein at least a part of the target protein is expressed from an exogenous sequence, and the target protein comprises PTGFRN, BSG, IGSF2, IGSF3, IGSF8, ITGB1, ITGA4, SLC3A2, ATP transporter or a fragment or a variant thereof. In some embodiments, the target protein does not comprise IGSF8 or a fragment or a variant thereof. In some embodiments, the target protein comprises a polypeptide of SEQ ID NO: 33.

In some embodiments, the exosome is isolated based on a binding between the target protein and a binding agent.

In some embodiments, the exosome is produced from a cell genetically modified to comprise the exogenous sequence, optionally wherein the cell is an HEK293 cell, a Chinese hamster ovary (CHO) cell, or a mesenchymal stem cell (MSC). In some embodiments, the cell is genetically modified to have a reduced expression of ADAM10.

In some embodiments, the cell comprises a plasmid comprising the exogenous sequence.

In some embodiments, the cell comprises the exogenous sequence inserted into a genome of the cell. In some embodiments, the exogenous sequence is inserted into a genomic site located 3' or 5' end of a genomic sequence encoding PTGFRN, BSG, IGSF2, IGSF3, IGSF8, ITGB1, ITGA4, SLC3A2 or ATP transporter. In some embodiments, the exogenous sequence is inserted into a genomic sequence encoding PTGFRN, BSG, IGSF2, IGSF3, IGSF8, ITGB1, ITGA4, SLC3A2 or ATP transporter. In some embodiments, the exogenous sequence does not encode IGSF8.

In some embodiments, the target protein is a fusion protein comprising PTGFRN, BSG, IGSF2, IGSF3, IGSF8, ITGB1, ITGA4, SLC3A2, ATP transporter, or a fragment or a variant thereof, and an affinity tag, wherein the affinity tag has affinity to the binding agent. In some embodiments, the target protein does not comprise IGSF8 or a fragment thereof.

In some embodiments, the target protein is a fusion protein comprising PTGFRN, BSG, IGSF2, IGSF3, IGSF8, ITGB1, ITGA4, SLC3A2, ATP transporter, or a fragment or a variant thereof, and a therapeutic peptide. In some embodiments, the target protein does not comprise IGSF8 or a fragment thereof.

The therapeutic peptide can be selected from a group consisting of a natural peptide, a recombinant peptide, a synthetic peptide, or a linker to a therapeutic compound. The therapeutic compound can be selected from the group consisting of nucleotides, amino acids, lipids, carbohydrates, and small molecules.

The therapeutic peptide can be an antibody or a fragment or a variant thereof. The therapeutic peptide can be an enzyme, a ligand, a receptor, or a fragment or a variant thereof. The therapeutic peptide can be an antimicrobial peptide or a fragment or a variant thereof.

In some embodiments, the target protein is a fusion protein comprising PTGFRN, BSG, IGSF2, IGSF3, IGSF8, ITGB1, ITGA4, SLC3A2, ATP transporter, or a fragment or a variant thereof, and a targeting moiety. The targeting moiety can be specific to an organ, a tissue, or a cell. In some embodiments, the target protein does not comprise IGSF8 or a fragment thereof.

In some embodiments, the exosome further comprises a second, different target protein, wherein the different target protein comprises PTGFRN, BSG, IGSF2, IGSF3, IGSF8, ITGB1, ITGA4, SLC3A2, ATP transporter, or a fragment or a variant thereof. In some embodiments, the exosome is isolated based on a binding between the different target protein and a different binding agent. In some embodiments, the target protein does not comprise IGSF8 or a fragment thereof.

In one aspect, the present invention relates to a pharmaceutical composition comprising the exosome of the present invention and an excipient.

In some embodiments, the pharmaceutical compositions are substantially free of macromolecules, wherein the macromolecules are selected from nucleic acids, contaminant proteins, lipids, carbohydrates, metabolites, and a combination thereof.

In one aspect, the present invention is directed to a cell for producing the exosome presented herein.

Specifically, some embodiments relate to a cell for producing exosomes, comprising an exogenous sequence inserted into a genomic sequence encoding PTGFRN, BSG, IGSF2, IGSF3, IGSF8, ITGB1, ITGA4, SLC3A2, or ATP transporter, wherein the exogenous sequence and the genomic sequence encodes a fusion protein. In some embodiments, the genomic sequence does not encode IGSF8.

The exogenous sequence can encode an affinity tag.

The exogenous sequence can encode a therapeutic peptide. The therapeutic peptide can be selected from a group consisting of a natural peptide, a recombinant peptide, a synthetic peptide, or a linker to a therapeutic compound. The therapeutic compound can be selected from the group consisting of nucleotides, amino acids, lipids, carbohydrates, and small molecules. The therapeutic peptide can be an antibody or a fragment or a variant thereof. The therapeutic peptide can be an enzyme, a ligand, a receptor, or a fragment or a variant thereof. The therapeutic peptide can be an antimicrobial peptide or a fragment or a variant thereof.

The exogenous sequence can encode a targeting moiety. The targeting moiety can be specific to an organ, a tissue, or a cell.

In some embodiments, the cell line is genetically modified to have a reduced expression of ADAM10.

In one aspect, the present invention provides an exosome produced from the cell line of the present invention. In some embodiments, the exosome includes the fusion protein on the surface at a higher density than a different fusion protein on the surface of a different exosome, wherein the different exosome is produced from a different cell line comprising the exogenous sequence inserted into a different genomic sequence encoding a conventional exosome protein, wherein the exogenous sequence and the different genomic sequence encodes the different fusion protein. In some embodiments, the conventional exosome protein is selected from the group consisting of CD9, CD63, CD81, PDGFR, GPI anchor proteins, LAMP2, LAMP2B, and a fragment thereof.

In another aspect, the present invention relates to a method of isolating a non-exosomal material, comprising the steps of: providing a sample comprising an exosome and the non-exosome material; contacting the sample with a binding agent having affinity to a target protein, wherein the target protein comprises PTGFRN, BSG, IGSF2, IGSF3, IGSF8, ITGB1, ITGA4, SLC3A2, ATP transporter or a fragment or a variant thereof, thereby inducing the exosome to bind to the binding agent; and isolating the non-exosome material.

In some embodiments, the non-exosomal material is virus or a protein. In some embodiments, the non-exosomal material is lentivirus, retrovirus, adeno-associated virus, or other enveloped or non-enveloped virus. In some embodiments, the non-exosomal material is a recombinant protein. In some embodiments, the isolated non-exosomal material is substantially free of exosomes.

In some embodiments, the target protein further comprises an affinity tag, wherein the affinity tag has affinity to the binding agent. In some embodiments, the target protein comprises a polypeptide of SEQ ID NO: 33. In some embodiments, the binding agent comprises an immunoglobulin, a protein, a peptide, or a small molecule. In some embodiments, the binding agent is attached to a solid support, optionally wherein the solid support comprises a porous agarose bead, a microtiter plate, a magnetic bead, or a membrane. In some embodiments, the solid support forms a chromatography column. In some embodiments, the step of contacting the sample with the binding agent is performed by applying the sample to the chromatography column.

In some embodiments, the methods of purification described herein are used for purification of nanovesicles. In some embodiments, the compositions and methods described herein are directed to nanovesicles.

5. BRIEF DESCRIPTION OF THE DRAWINGS

The figures depict various embodiments of the present invention for purposes of illustration only. One skilled in the art will readily recognize from the following discussion that alternative embodiments of the structures and methods illustrated herein may be employed without departing from the principles of the invention described herein.

FIG. 1 provides an image of sample-containing Optiprep™ density gradient after ultracentrifugation. Marked with brackets are the top fraction containing exosomes ("Top"), the middle fraction containing cell debris ("Middle") and the bottom fraction containing high density aggregates and cellular debris ("Bottom").

Figure 2:
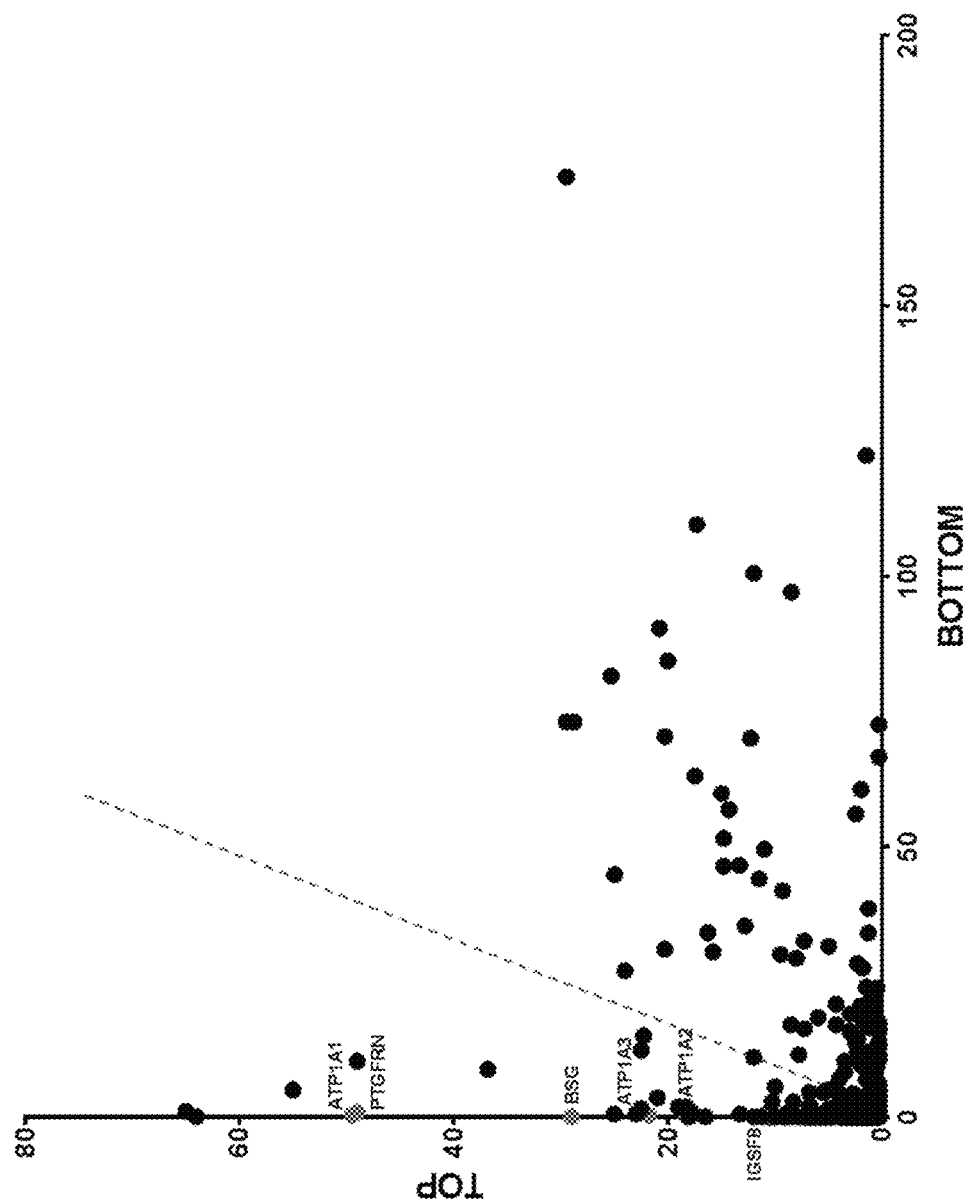

FIG. 2 is a dot-graph showing proteins identified from the top fraction (Y-axis) and proteins identified from the bottom fraction (X-axis) of Optiprep™ ultracentrifugation. Proteins plotted above the dotted line represent exosome-enriched proteins, while those below the dotted line represent proteins not specific to exosomes.

FIG. 3 provides a tryptic peptide coverage map of PTGFRN.

FIG. 4 provides a tryptic peptide coverage map of IGSF8.

FIG. 5 provides a tryptic peptide coverage map of Basigin (BSG).

Figures 6A, 6B:
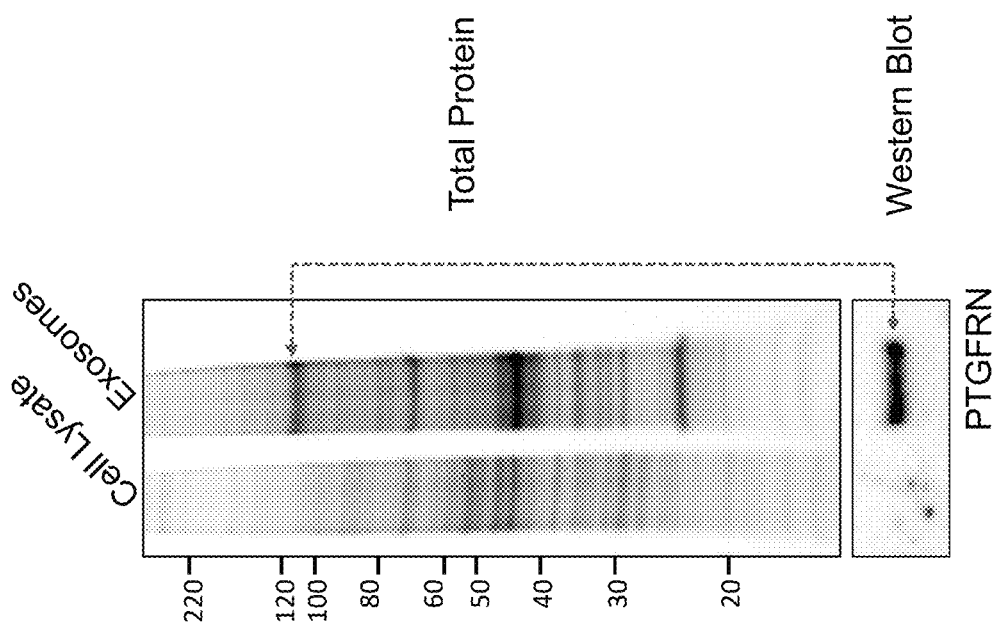

FIG. 6A shows a picture from protein blotting of total cell lysate (left) and purified exosome populations (right) collected from HEK293 cells. FIG. 6B shows a result of western blotting of the gel provided in FIG. 6A with an antibody against PTGFRN. The band detected on the right column corresponds to a band at ~110 kDa in FIG. 6A.

Figures 7A, 7B:
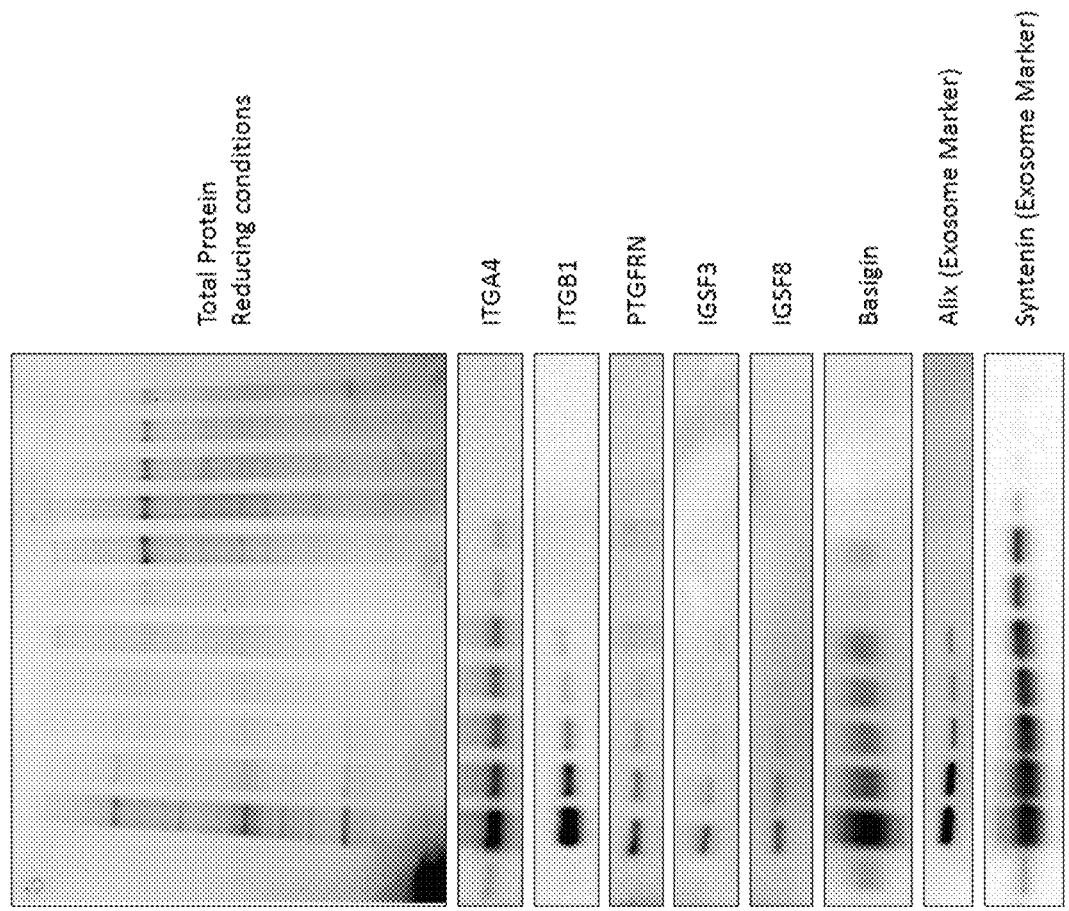

FIG. 7A shows protein blotting of twelve fractions collected from a purification using self-forming Optiprep™ gradients. FIG. 7B shows a result of western blotting of the gel presented in FIG. 7A with antibodies against ITGA4, ITGB1, PTGFRN, IGSF3, IGSF8, Basigin, Alix, or Syntenin. Each of the novel exosome surface proteins (ITGA4, ITGB1, PTGFRN, IGSF8, Basigin) is detected in the same fractions as the well-known exosome marker proteins (Alix, Syntenin).

Figure 8:
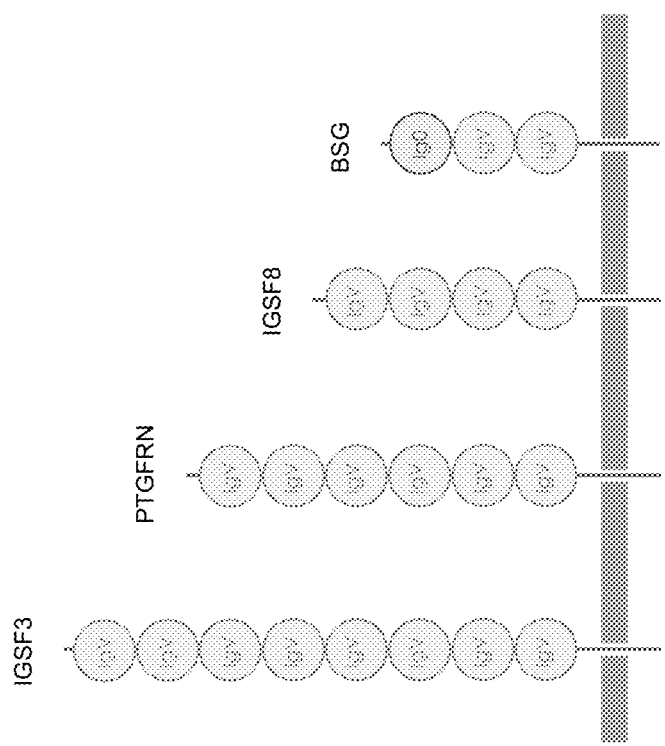

FIG. 8 illustrates exosome surface proteins (ITGA4, ITGB1, PTGFRN, IGSF8, BSG) that are used for various embodiments of the present invention, for example, for targeting a fusion protein on the surface of an exosome, or as a target for affinity purification of an exosome.

Figure 9B:
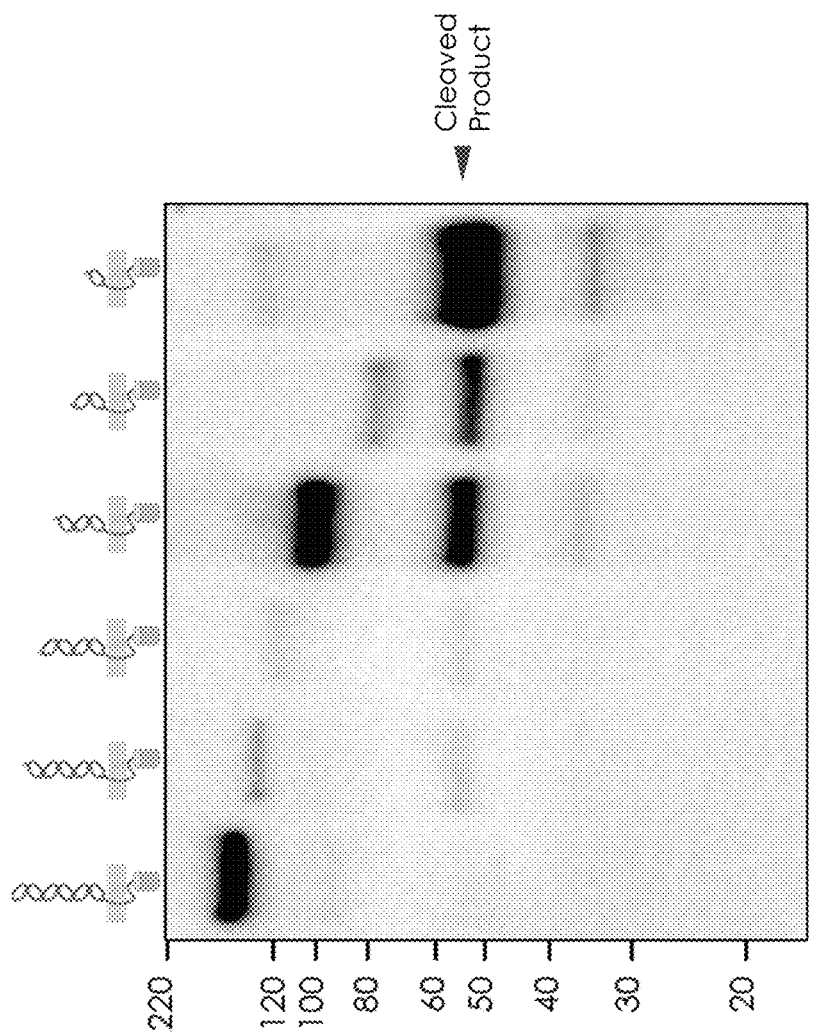
Figure 9A:
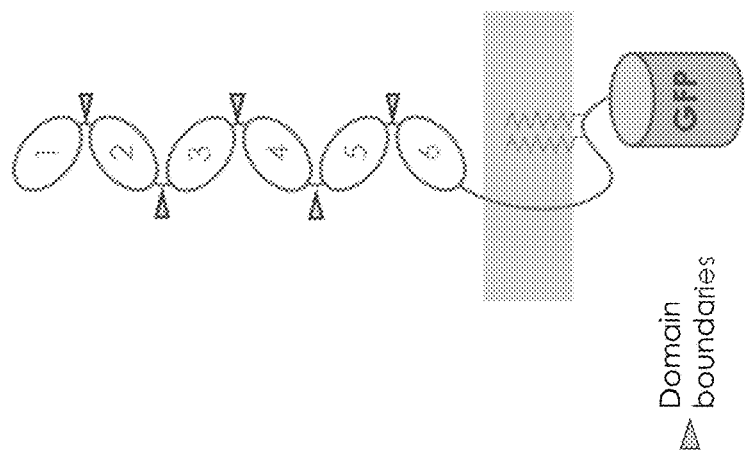

FIG. 9A illustrates the structure of PTGFRN with identification of boundaries of IgV domains (arrows) and GFP fused to the C terminus of PTGFRN. FIG. 9B provides a gel picture from western blotting exosomes isolated from a cell culture overexpressing various GFP-PTGFRN fusion proteins. GFP-PTGFRN fusion proteins were detected using an antibody against GFP.

Figure 10:
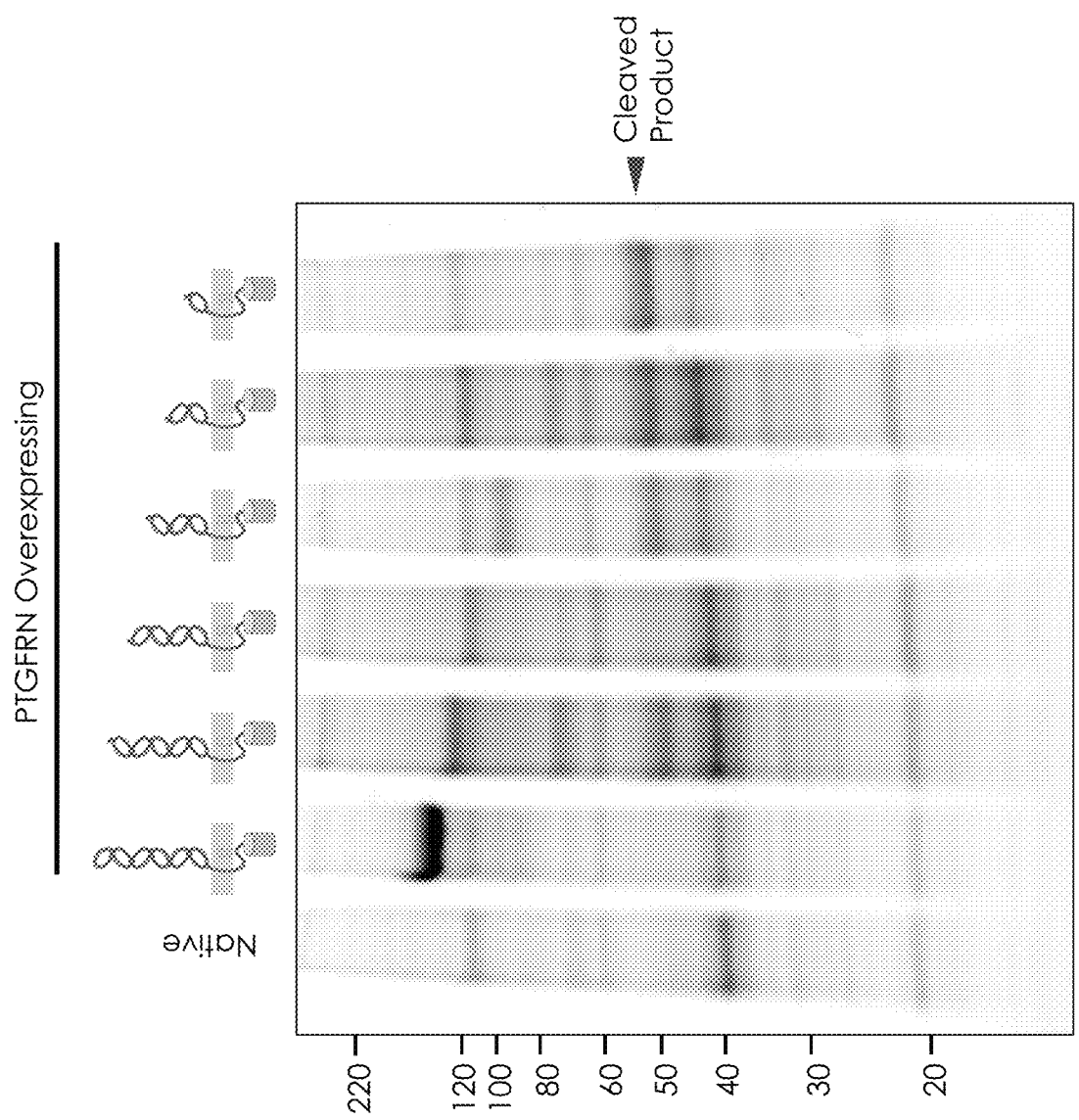

FIG. 10 provides a gel picture running total proteins of the purified exosomes isolated from cells overexpressing various GFP-PTGFRN fusion proteins.

Figure 11B:
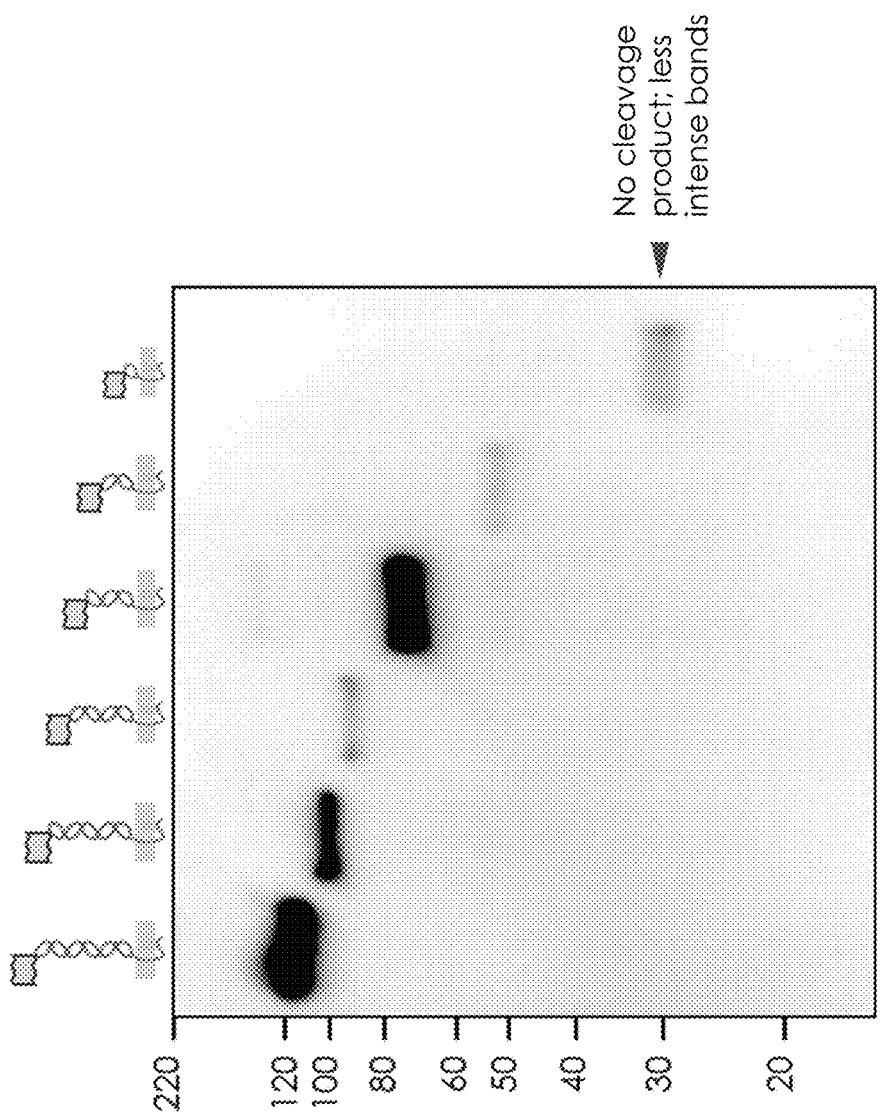
Figure 11A:
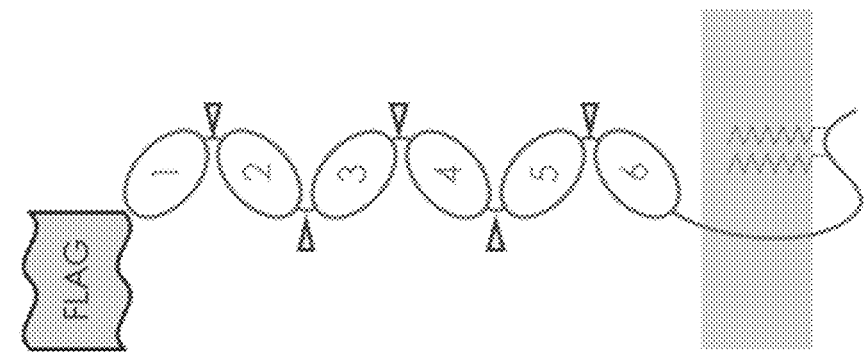

FIG. 11A illustrates the structure of PTGFRN with identification of boundaries of IgV domains (arrows) and FLAG fused to the N terminus of PTGFRN.

FIG. 11B provides a gel picture from western blotting exosomes isolated from a cell culture overexpressing various FLAG-PTGFRN fusion proteins. GFP-PTGFRN fusion proteins were detected using an antibody against FLAG tag.

FIG. 12A provides a gel picture running total proteins of the purified exosomes isolated from wild type cells (ADAM10+) or ADAM10 knockout cells (ADAM10−), each cells expressing a GFP fusion protein containing full-length PTGFRN (PTGFRN-GFP) or a truncated PTGFRN (PTGFRN_IgV3-GFP). FIG. 12B provides a gel picture from western blotting the samples of FIG. 12A using an antibody against ADAM10. FIG. 12C provides a gel picture from western blotting the samples of FIG. 12A using an antibody against GFP.

Figure 13:
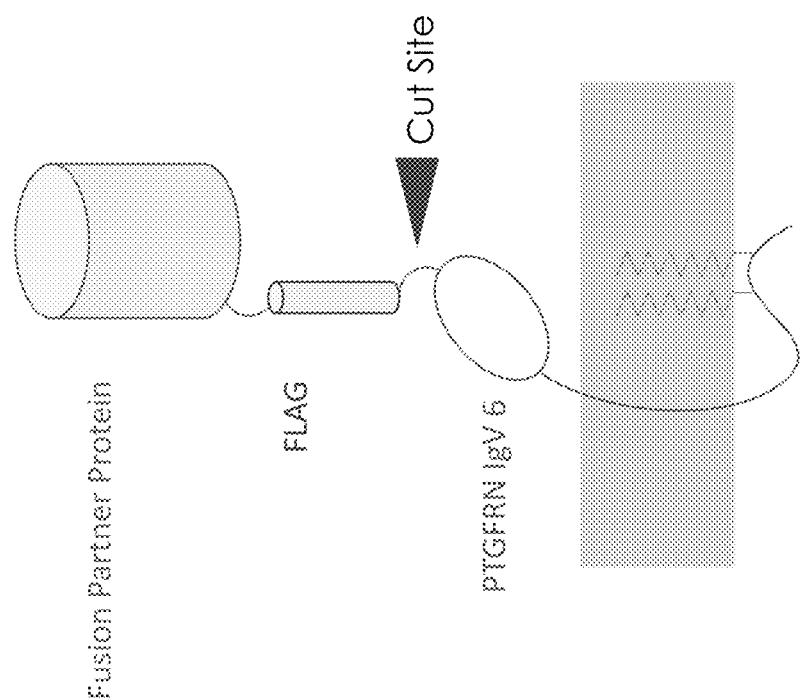

FIG. 13 illustrates the structure of a fusion protein containing PTGFRN lacking five of the six IgV domains (PTGFRN_IgV6), FLAG tag, and a fusion partner protein.

FIG. 14A provides sequences of PTGFRN_IgV6 (#451) and serial truncation mutants of PTGFRN_IgV6 lacking four (#452), eight (#453), or twelve (#454) additional amino acids. FIG. 14B provides a gel picture running total proteins of the purified exosomes isolated from cells overexpressing a fusion protein #451, 452, 453 or 454. FIG. 14C provides a gel picture from western blotting the sample of FIG. 14B using an antibody against FLAG.

Figure 15:
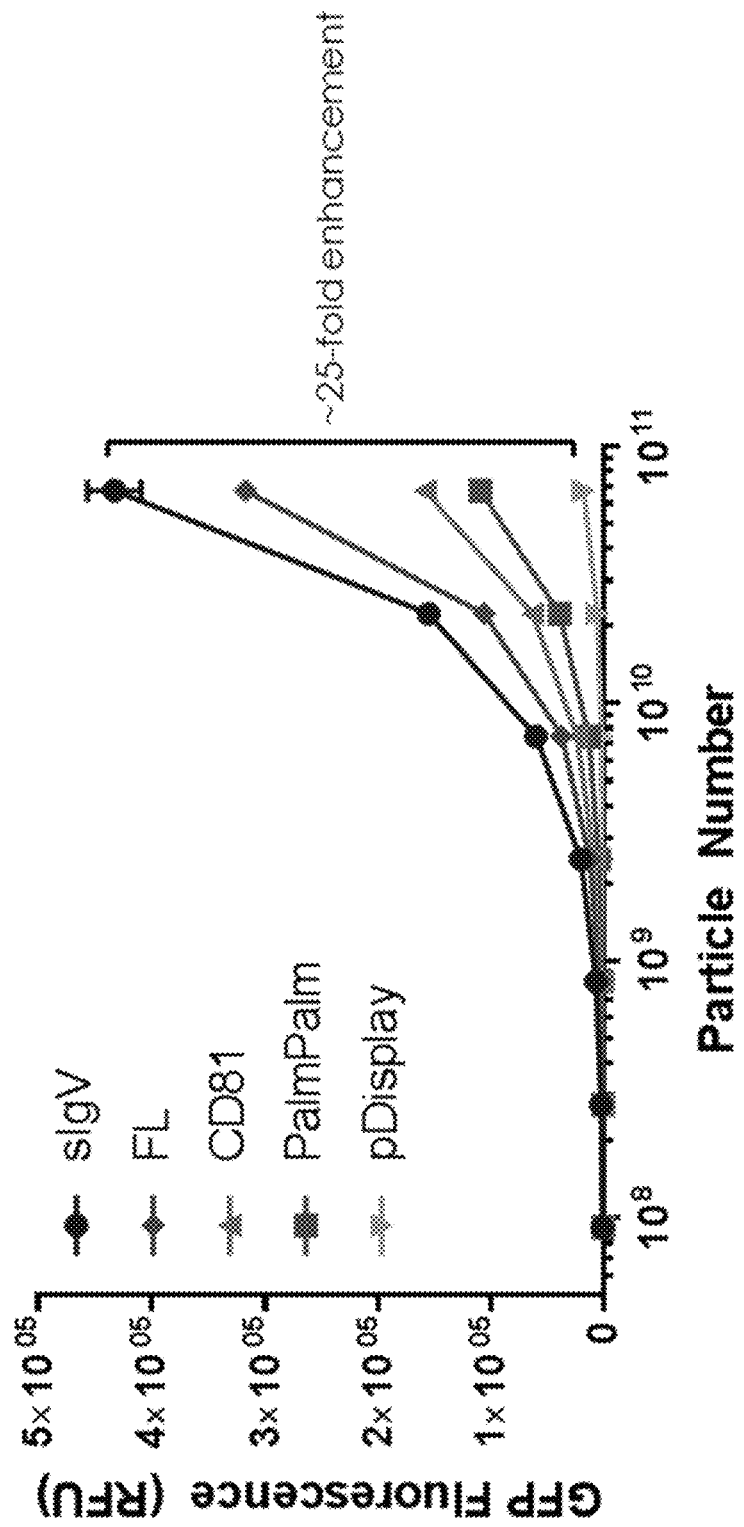

FIG. 15 provides GFP fluorescence signals detected from exosomes isolated from cells overexpressing various GFP fusion proteins—the GFP fusion proteins contain GFP fused to the luminal side of the frequently used pDisplay scaffold (PDGF receptor), PalmPalm (palmitoylation sequence), CD81, or either full length PTGFRN (FL) or PTGFRN_454 (sIgV).

Figure 16B:
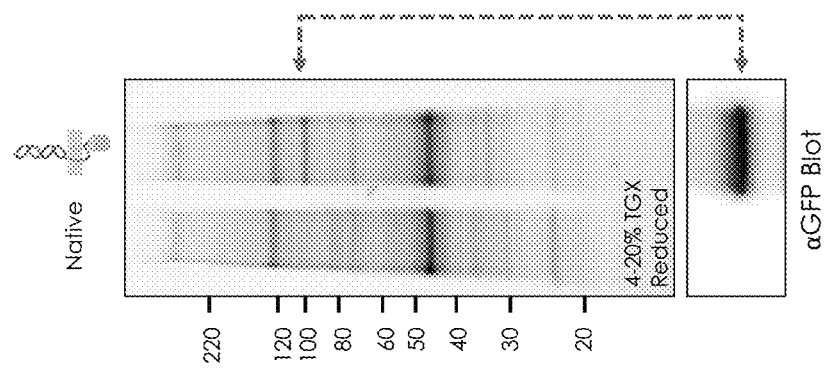
Figure 16A:
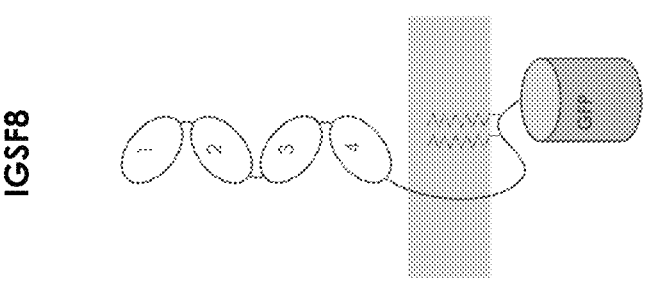

FIG. 16A illustrates the structure of a fusion protein containing IGSF8 and GFP fused to the C terminus of IGSF8.

FIG. 16B provides a gel picture running total proteins from exosomes isolated from untransfected HEK293 cells (native) or HEK cells stably transfected with a construct encoding an IGFS8-GFP fusion protein. FIG. 16B also provides on the bottom a gel picture from western blotting the sample with an antibody against GFP.

Figure 17:
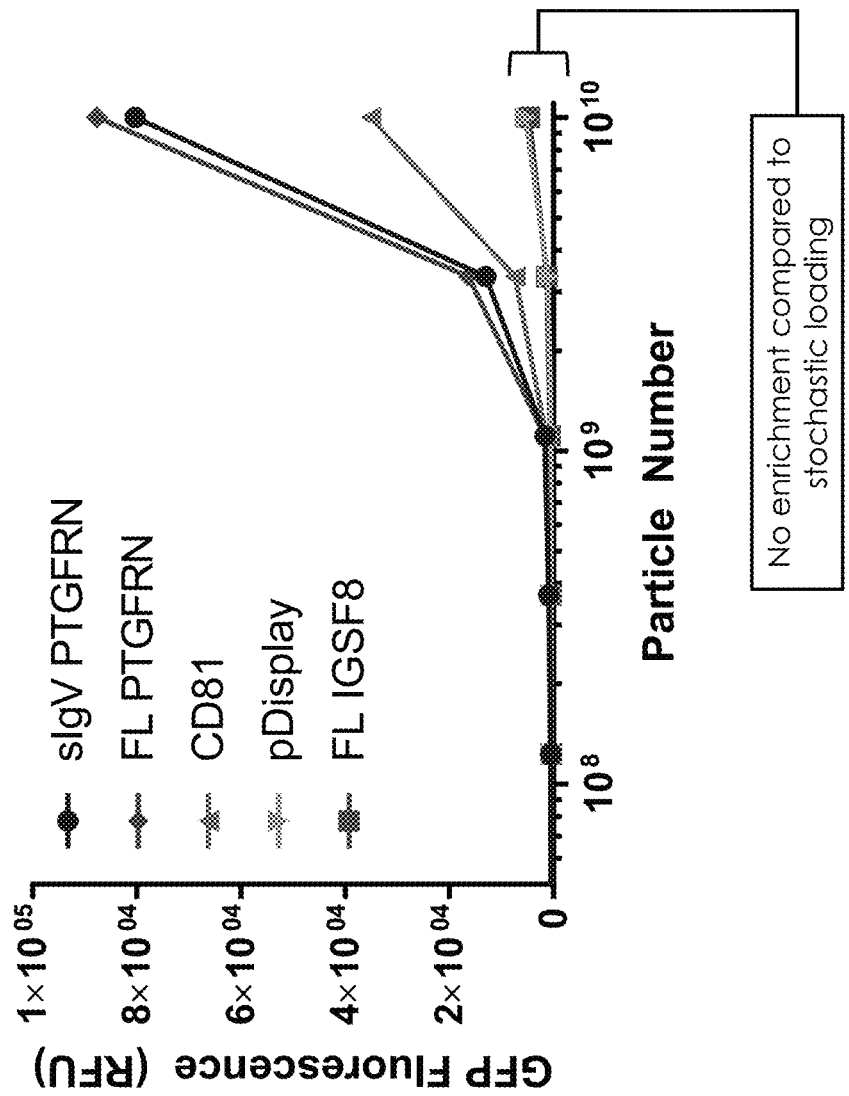

FIG. 17 provides GFP fluorescence signals detected from exosomes isolated from cells overexpressing various GFP fusion proteins—the GFP fusion proteins contain GFP fused to the luminal side of the frequently used pDisplay scaffold (PDGF receptor), CD81, full length IGSF8, or either full length PTGFRN (FL) or PTGFRN_454 (sIgV).

Figure 18:
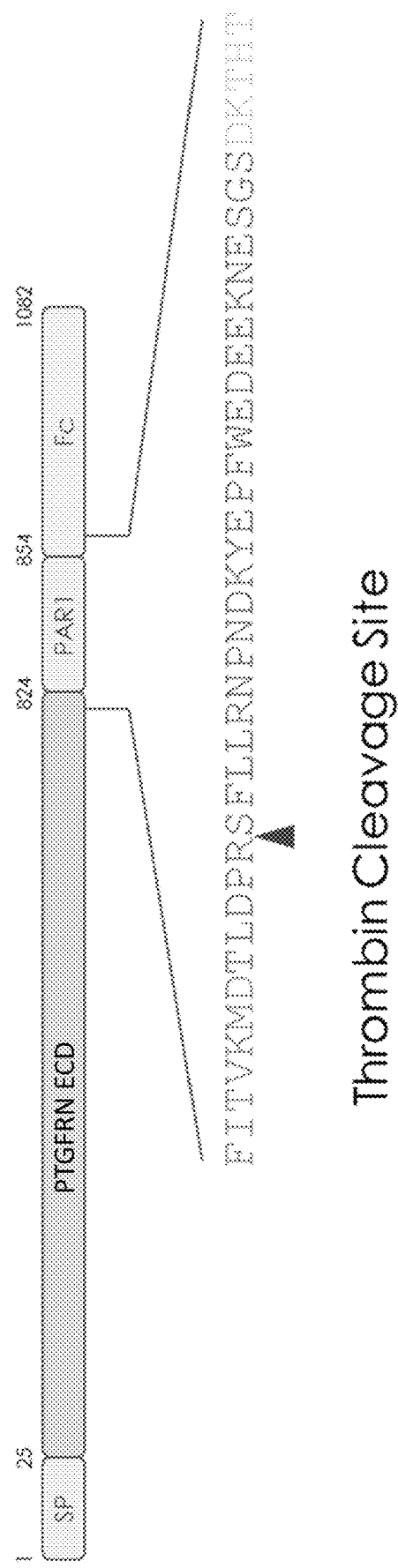

FIG. 18 provides a structure of a fusion protein containing the extracellular domain (ECD) of PTGFRN, the endogenous signal peptide at the N terminus (SP), a PAR1 cleavage site, and Fc domain at the C-terminus.

FIG. 19A provides a gel filtration chromatography result of purified ECD of PTGFRN in PBS pH 7.4 using a Superdex 200 column (Millpore Sigma) at 280 nm UV fluorescence. FIG. 19B provides an SDS-PAGE gel picture from gel filtration chromatography of eluate containing purified ECD of PTGFRN.

Figure 20B:
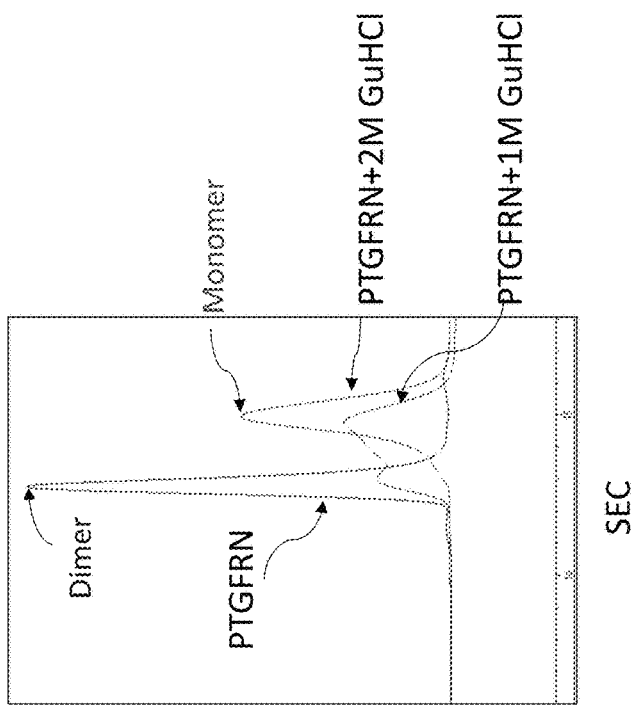
Figure 20A:
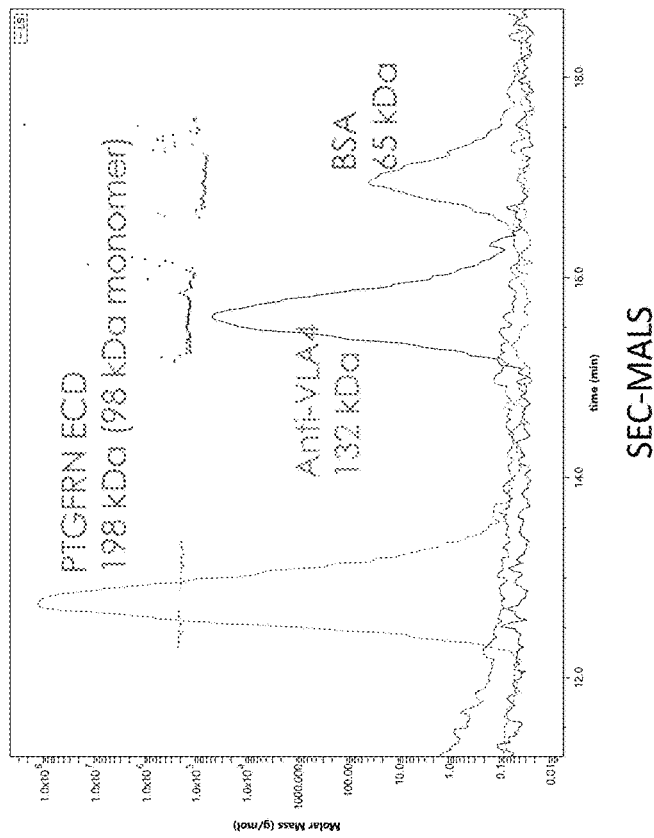

FIG. 20A provides size exclusion chromatography/multiangle light scattering (SEC-MALS) results of PTGFRN ECD, anti-VLA4 antibody, and BSA. FIG. 20B provides size exclusion chromatography (SEC) results of PTGFRN ECD in the absence of guanidium chloride (GuHCl), or in the presence of 1M, or 2M guanidinium chloride (GuHCl). Peaks representing a monomer or a dimer of PTGFRN are indicated.

FIG. 21 provides top three hits identified as PTGFRN ectodomain binding partners from a binding assay at pH 7.4 (top), and top five hits identified from the binding assay at pH 5.6 (bottom).

Figure 22:
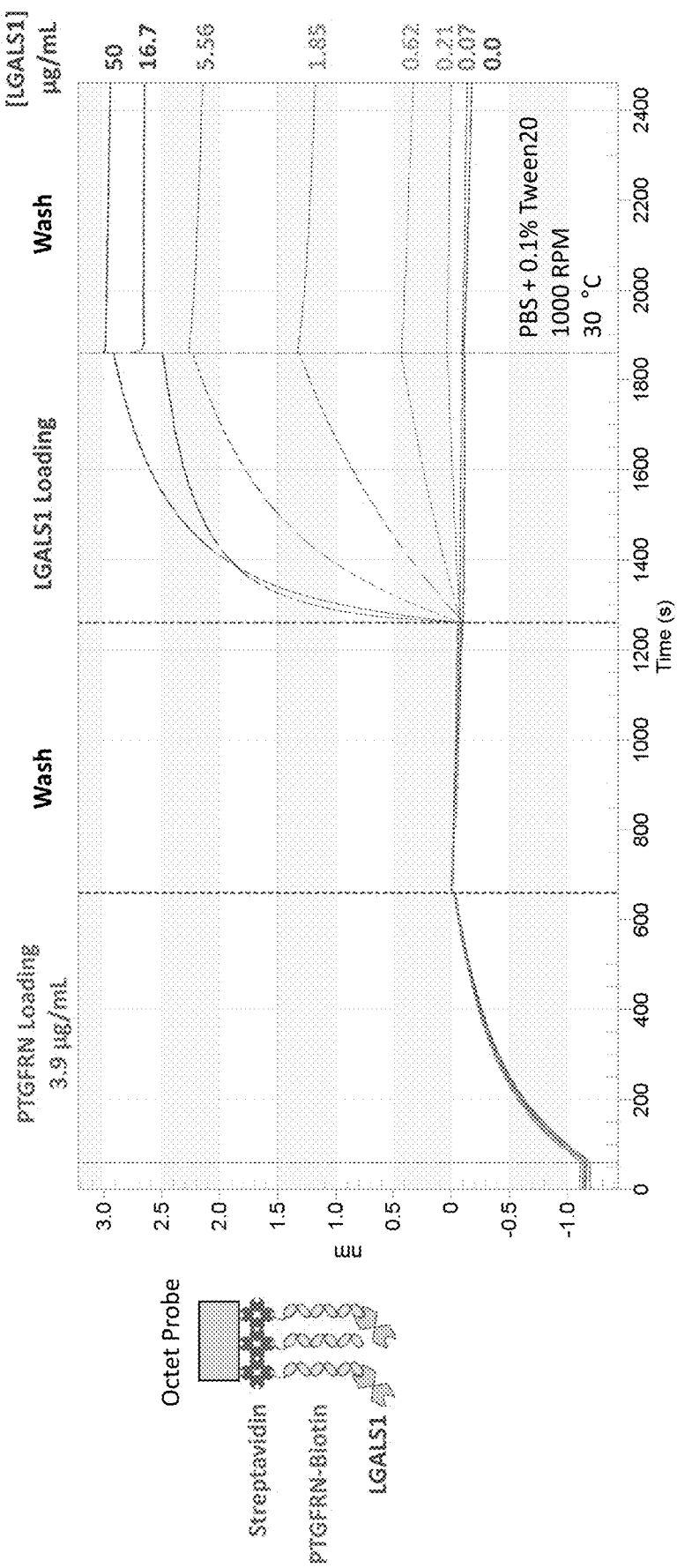

FIG. 22 provides bio-layer interferometry (BLI) results for studying the interaction between PTGFRN and LGALS1 in the presence of increasing concentrations of LGALS1.

Figure 23:
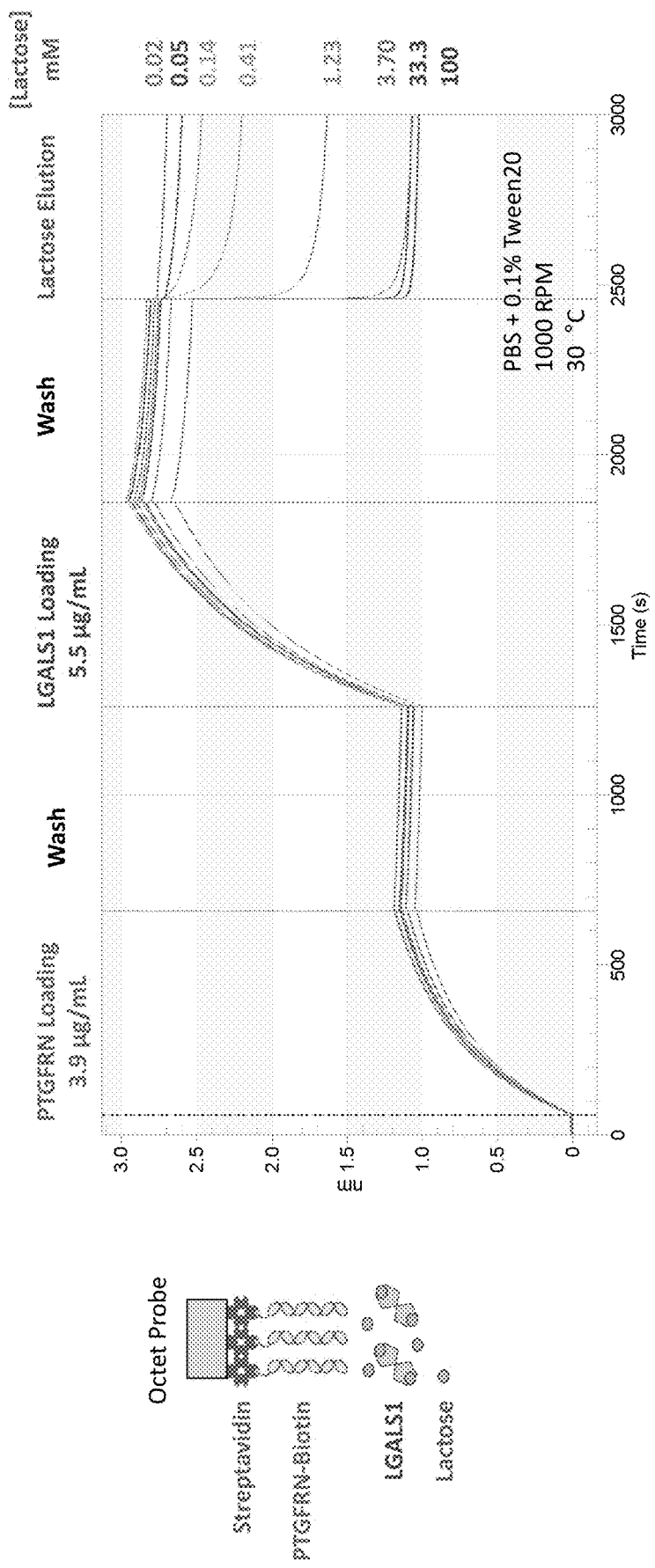

FIG. 23 provides bio-layer interferometry (BLI) results for studying the interaction between PTGFRN and LGALS1 in the presence of increasing concentrations of Lactose.

Figure 24:
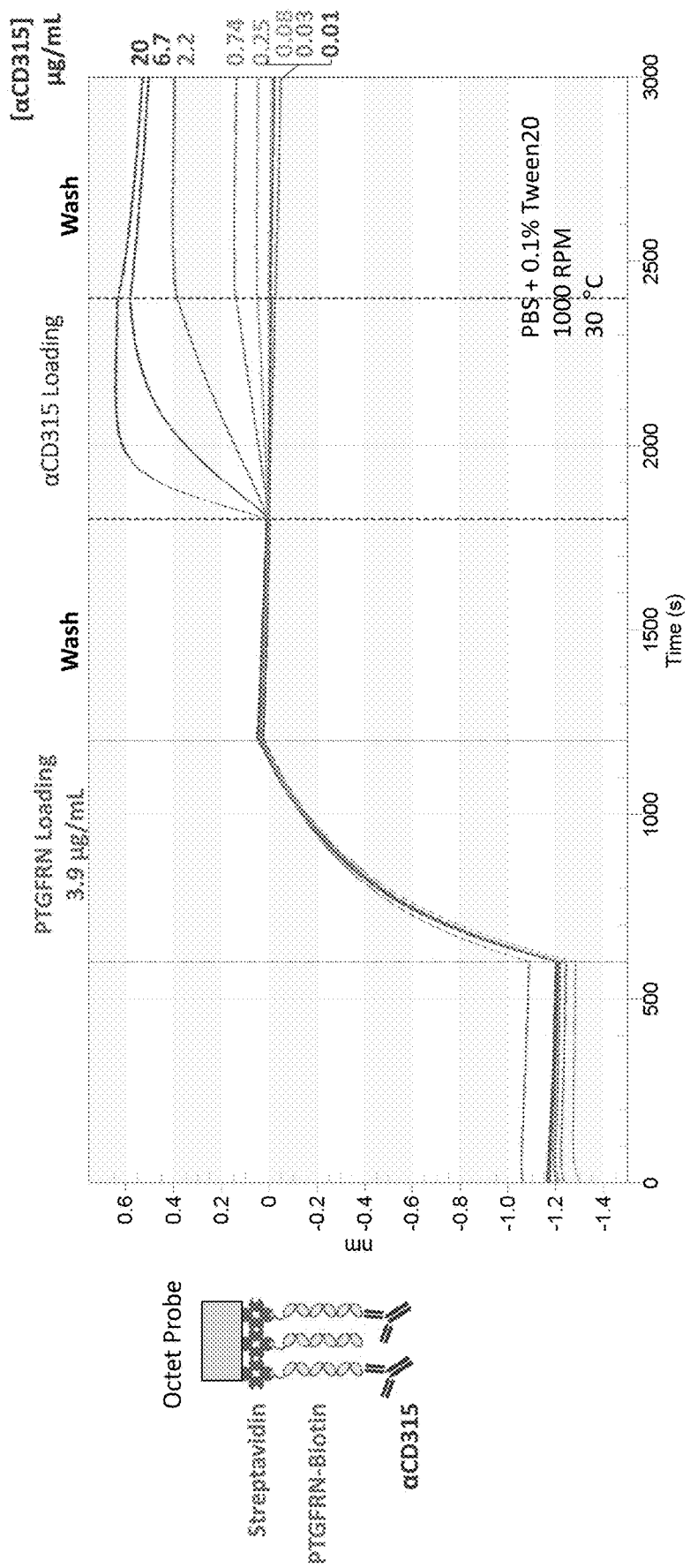

FIG. 24 provides bio-layer interferometry (BLI) results for studying the interaction between PTGFRN and anti-CD315 antibody in the presence of increasing concentrations of anti-CD315 antibody.

Figure 25:
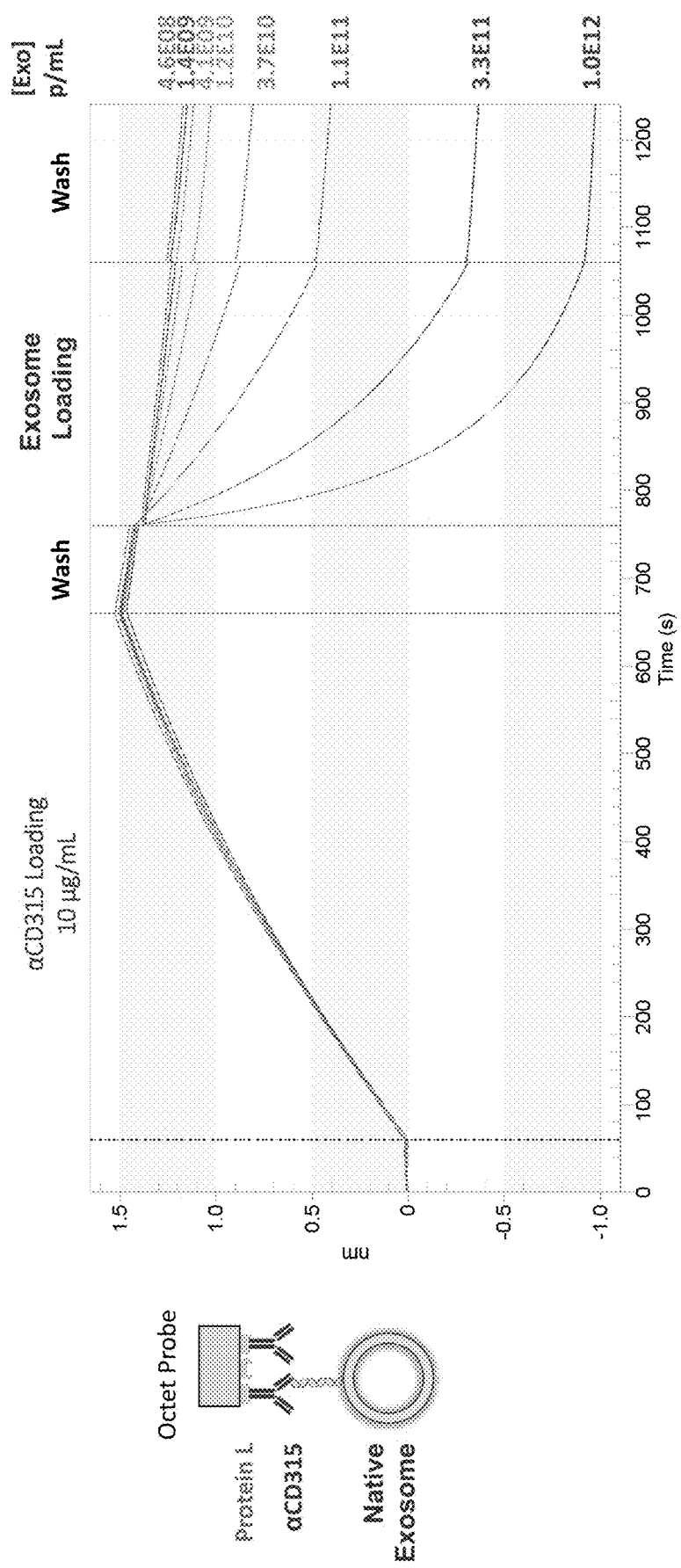

FIG. 25 provides bio-layer interferometry (BLI) results for studying the interaction between anti-CD315 antibody and native exosomes in the presence of increasing concentrations of native exosomes isolated from HEK293.

Figure 26:
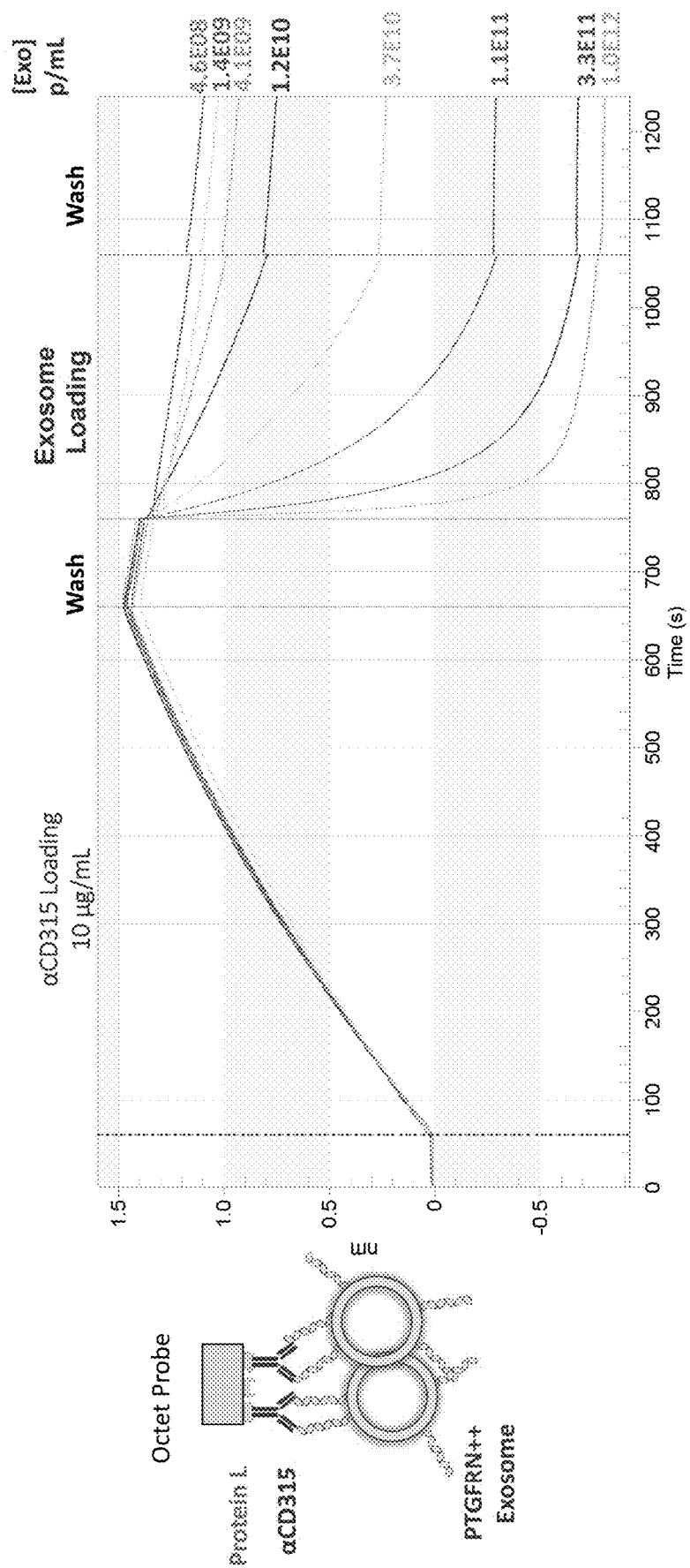

FIG. 26 provides bio-layer interferometry (BLI) results for studying the interaction between anti-CD315 antibody and exosomes modified to overexpress PTGFRN (PTGFRN++ exosomes) in the presence of increasing concentrations of the modified exosomes.

Figure 27:
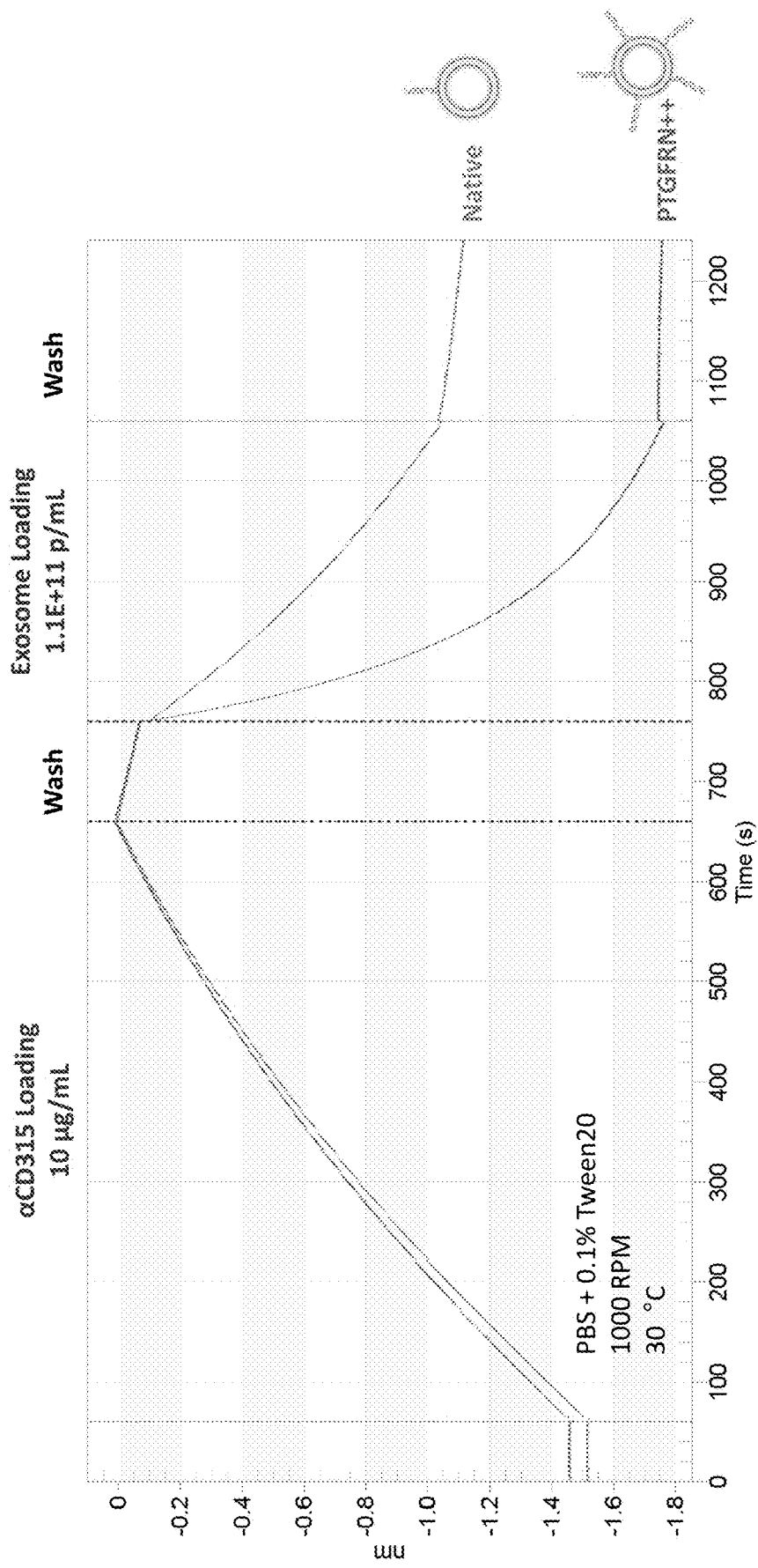

FIG. 27 provides bio-layer interferometry (BLI) results for comparing the interaction between anti-CD315 antibody and native exosomes, or between anti-CD315 antibody and modified exosomes overexpressing PTGFRN (PTGFRN++).

Figure 28:
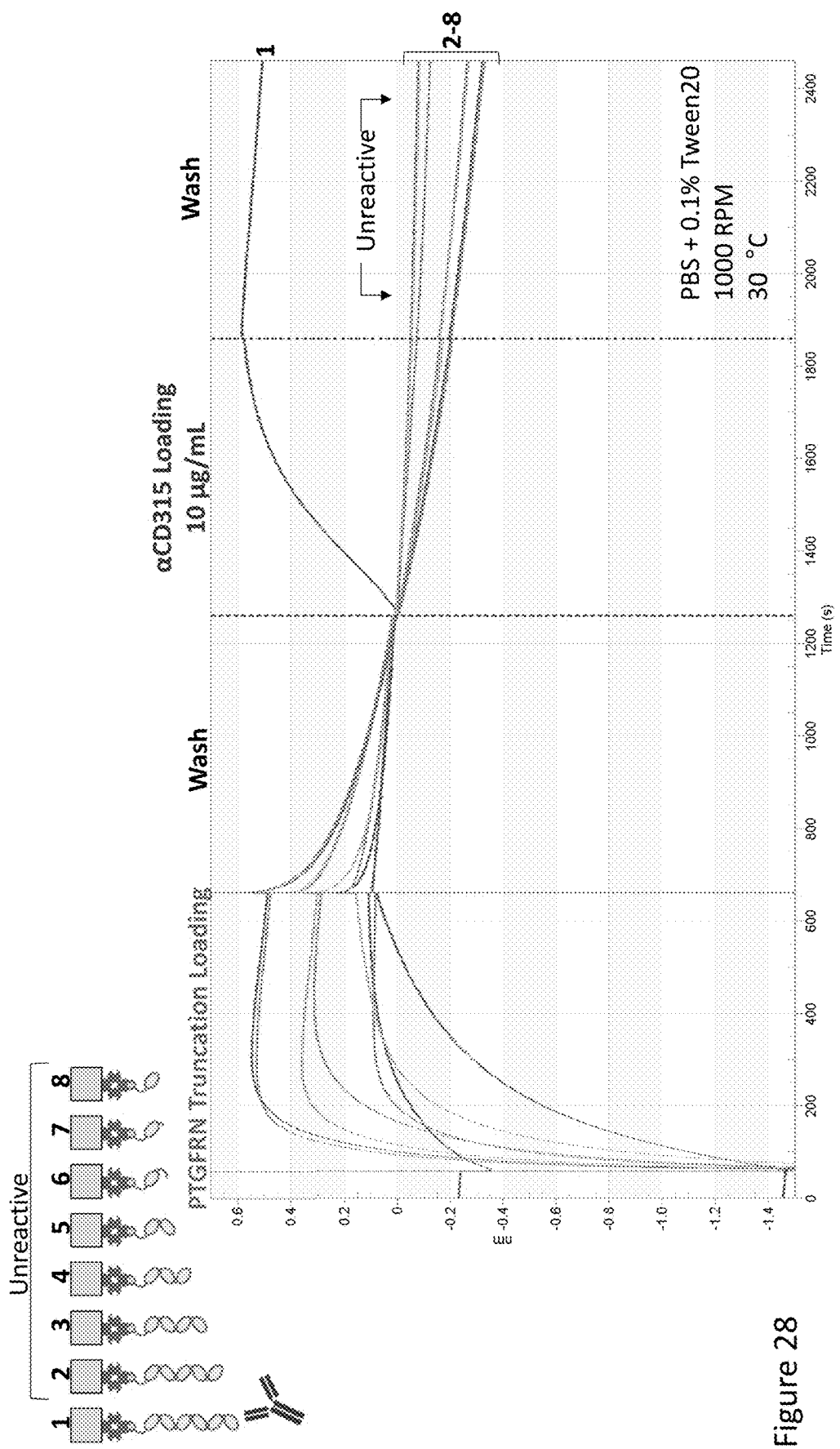

FIG. 28 provides bio-layer interferometry (BLI) results for studying the interaction between anti-CD315 antibody and full-length PTGFRN or between anti-CD315 antibody and a series of truncated mutants of PTGFRN.

Figure 29B:
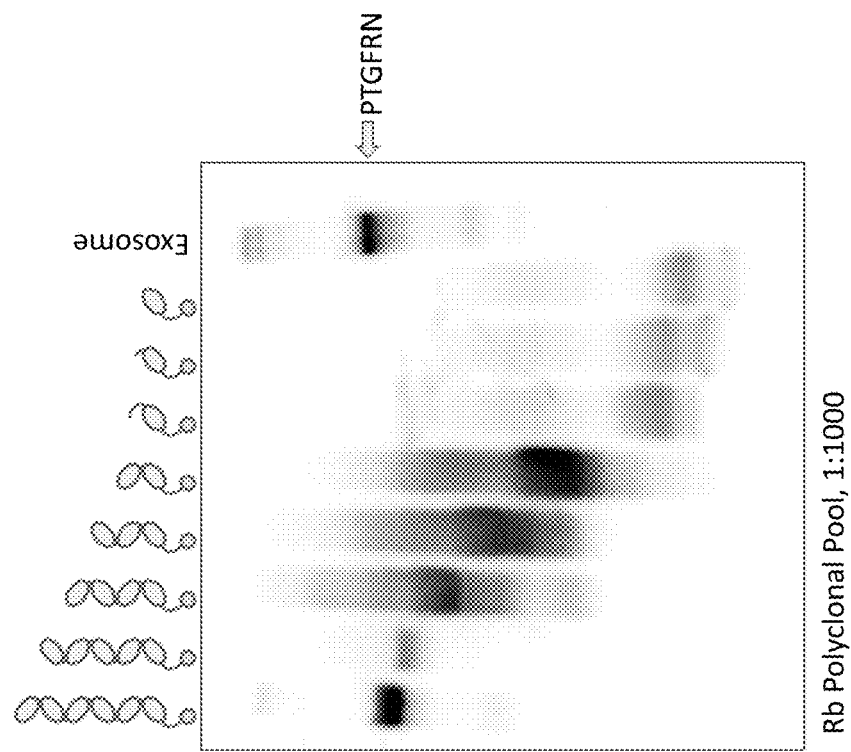
Figure 29A:
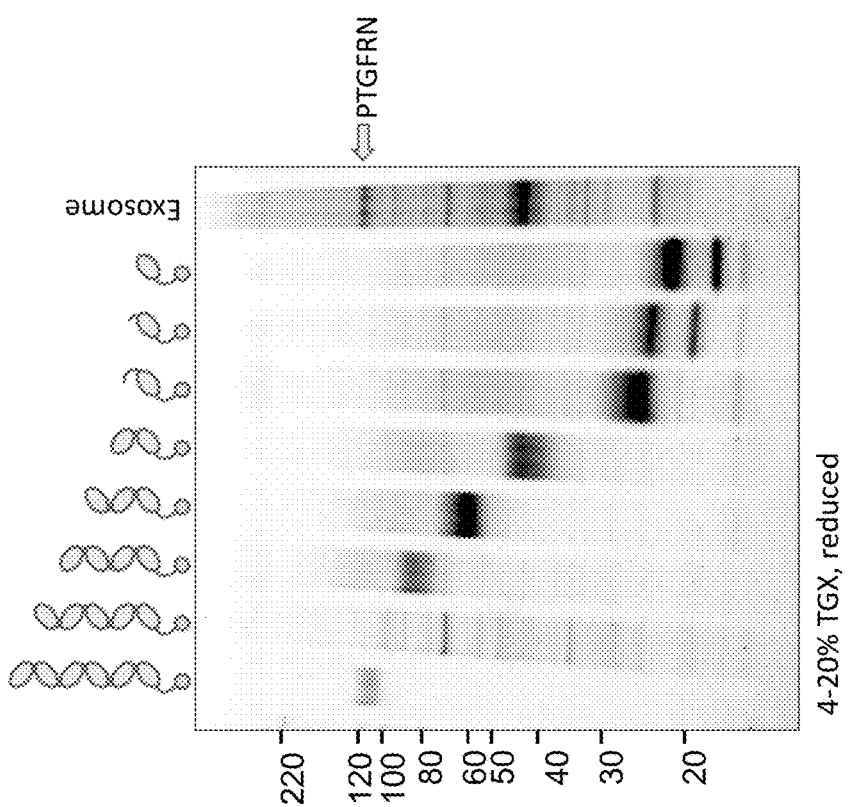

FIG. 29A provides a gel picture running in vivo biotinylated proteins including truncated mutants of recombinant PTGFRN isolated from transfected HEK cells, and purified exosomes from HEK293 cells. FIG. 29B provides a gel picture from western blotting the sample of FIG. 29A using pooled polyclonal PTGFRN antibodies.

Figure 30:
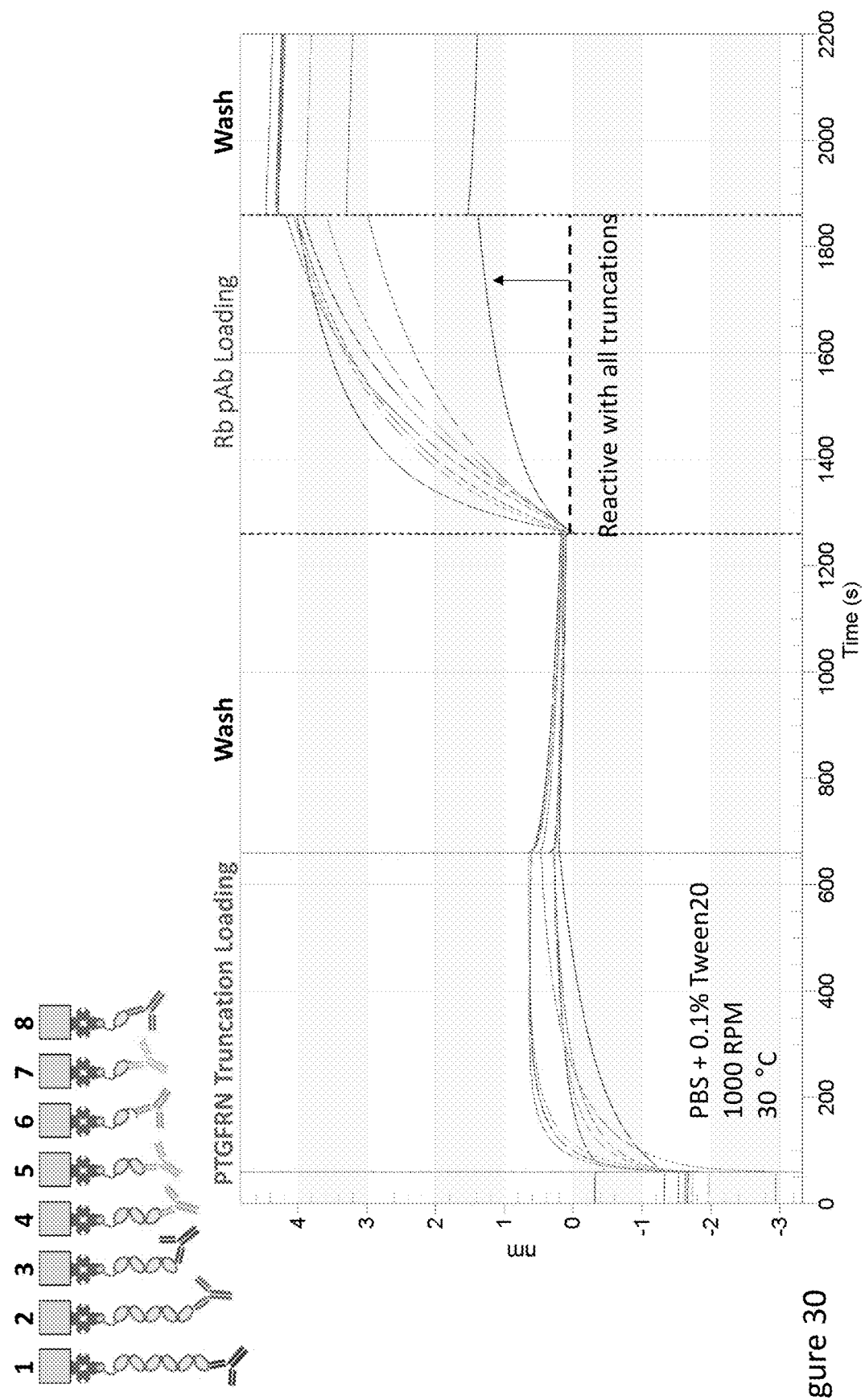

FIG. 30 provides bio-layer interferometry (BLI) results for studying the interaction between polyclonal PTGFRN antibodies and various truncation mutants of PTGFRN.

FIG. 31 provides the number of peptide spectrum matches (PSMs) of surface proteins (PTGFRN, IGSF8, IGSF3, BSG, SLC3A2, ITGB1, CD81, and CD9) for exosomes purified from various cell lines of different origins (HEK293SF, kidney; HT1080, connective tissue; K562, bone marrow;

MDA-MB-231, breast; Raji, lymphoblast; mesenchymal stem cell (MSC), bone marrow).

Figure 32B:
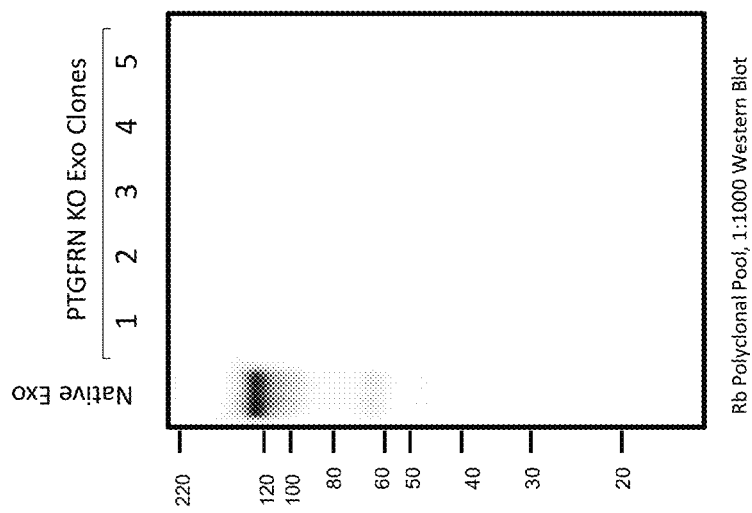
Figure 32A:
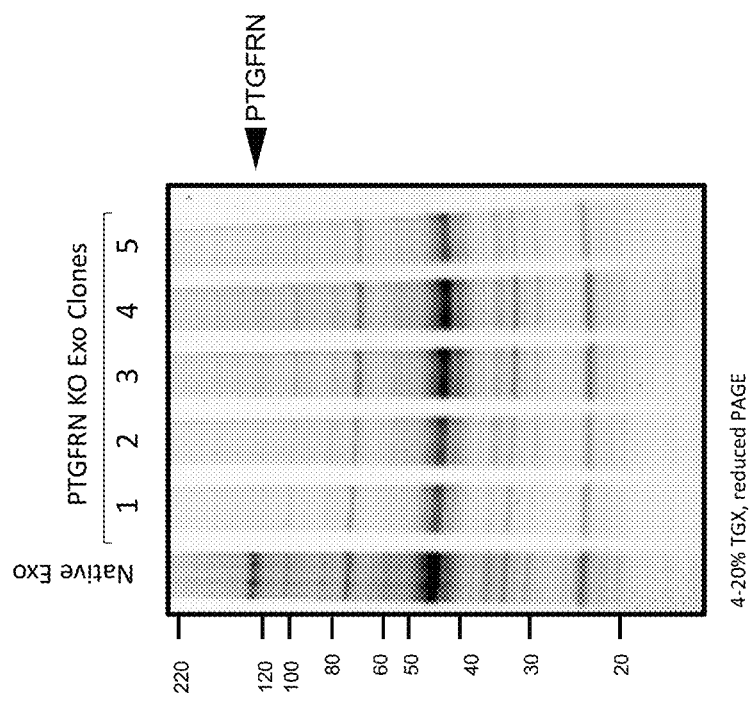

FIG. 32A provides a gel picture running native and PTGFRN knockout (KO) exosomes. FIG. 32B provides a gel picture from western blotting the samples of FIG. 32A using pooled polyclonal PTGFRN antibodies.

Figure 33:
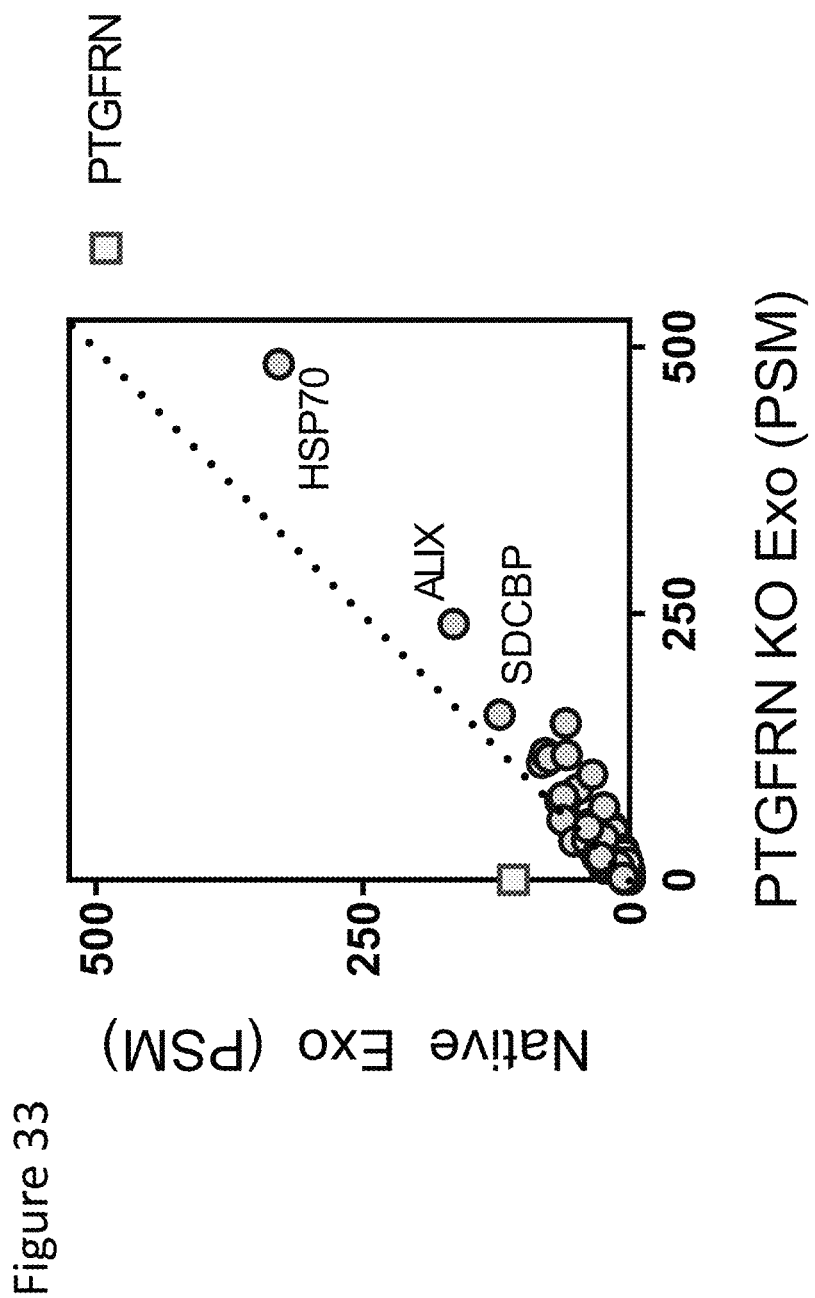

FIG. 33 provides a scatter plot of peptide spectrum matches (PSMs) from purified native (y-axis) and PTGRN KO (x-axis) exosomes.

Figure 34:
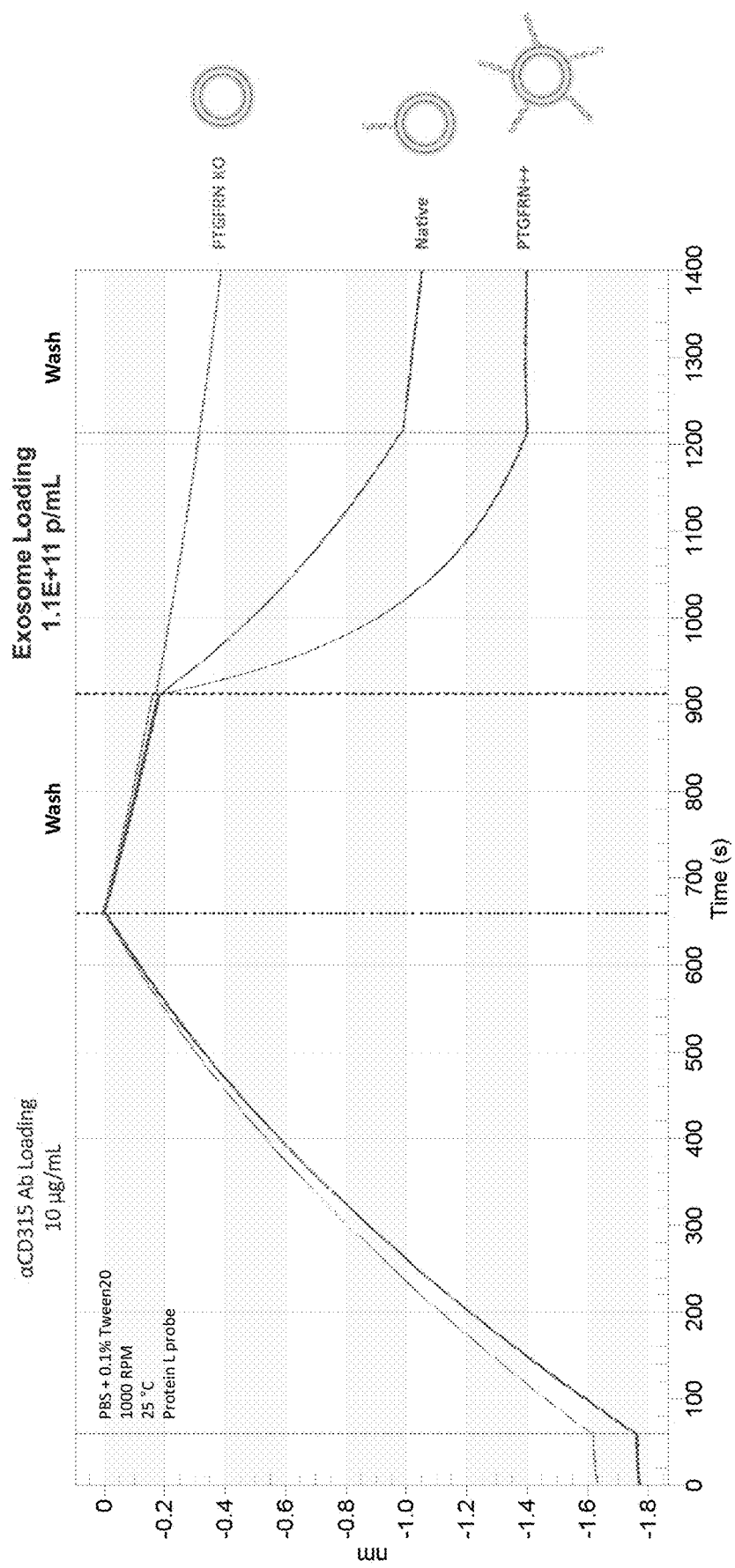

FIG. 34 provides BLI results for studying the interaction between a monoclonal anti-CD315 antibody and either native, PTGFRN++, and PTGFRN KO exosomes.

Figures 35A, 35B:
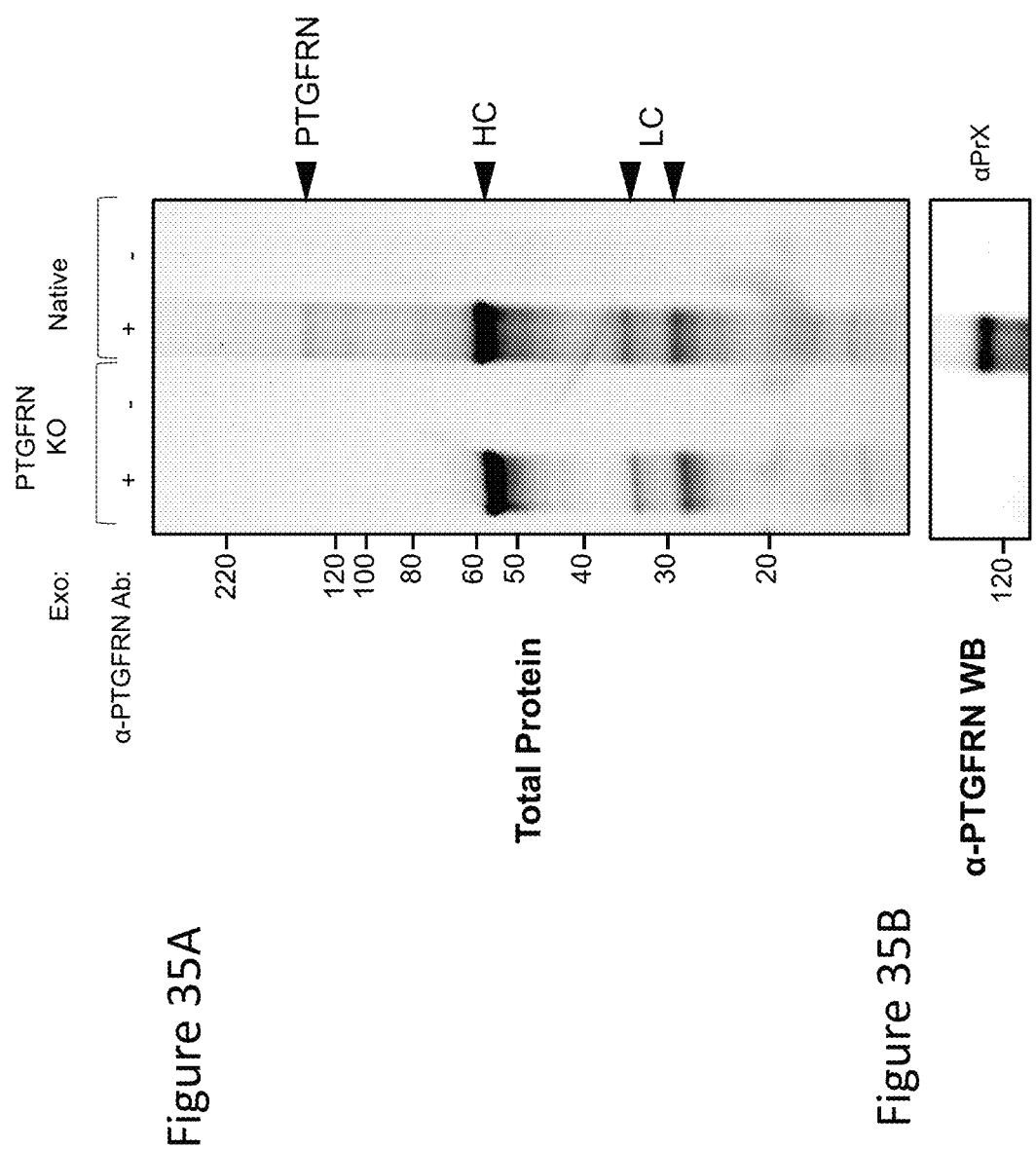

FIG. 35A provides a picture of a polyacrylamide gel from an in vitro exosome purification of native and PTGFRN knockout (KO) exosomes using an immobilized monoclonal anti-PTGFRN antibody. FIG. 35B provides a gel picture from western blotting the samples of FIG. 35A using an anti-PTGFRN antibody.

Figures 36A, 36B:
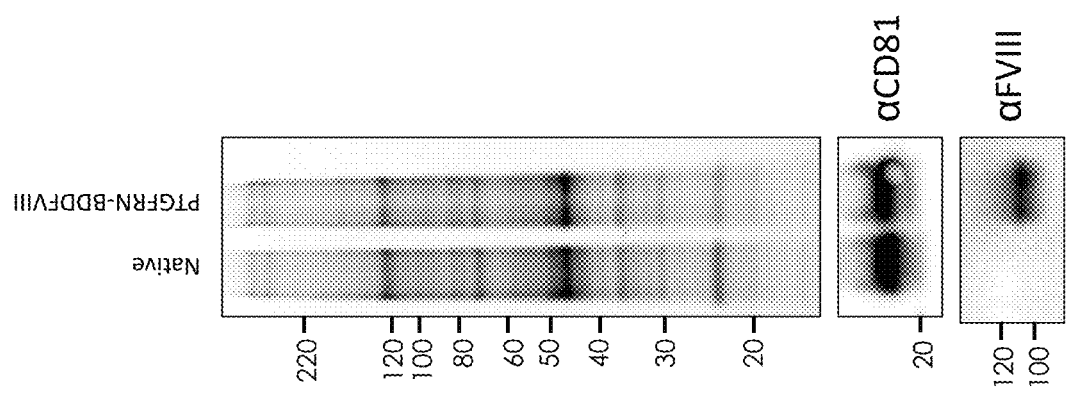

FIG. 36A provides a picture of a polyacrylamide gel running native exosomes or modified exosomes engineered to express PTGFRN-BDDFIII.

FIG. 36B provides a gel picture from western blotting the samples from FIG. 36A using CD81 antibodies (top) or FVIII antibodies (bottom).

Figures 37A, 37B:
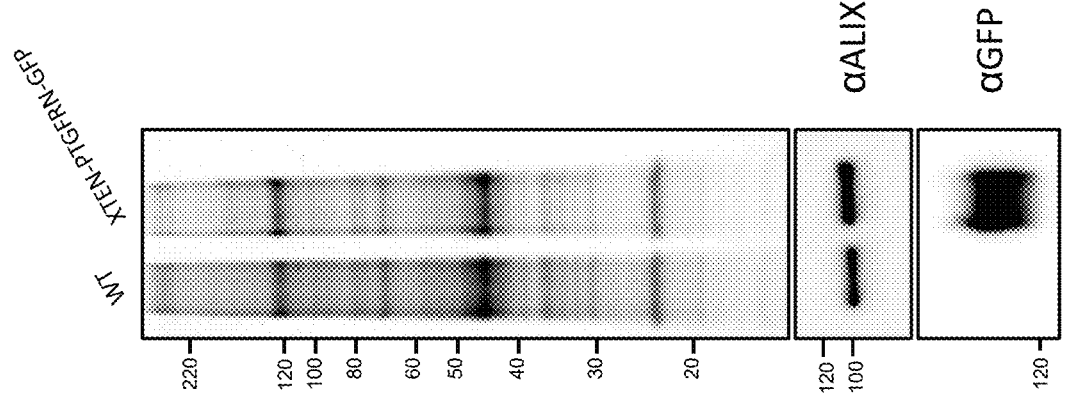

FIG. 37A provides a picture of a polyacrylamide gel running native exosomes or modified exosomes engineered to express XTEN-PTGFRN-GFP. FIG. 37B provides a gel picture from western blotting the samples from FIG. 37A using ALIX antibodies (top) or GFP antibodies (bottom).

Figure 38:
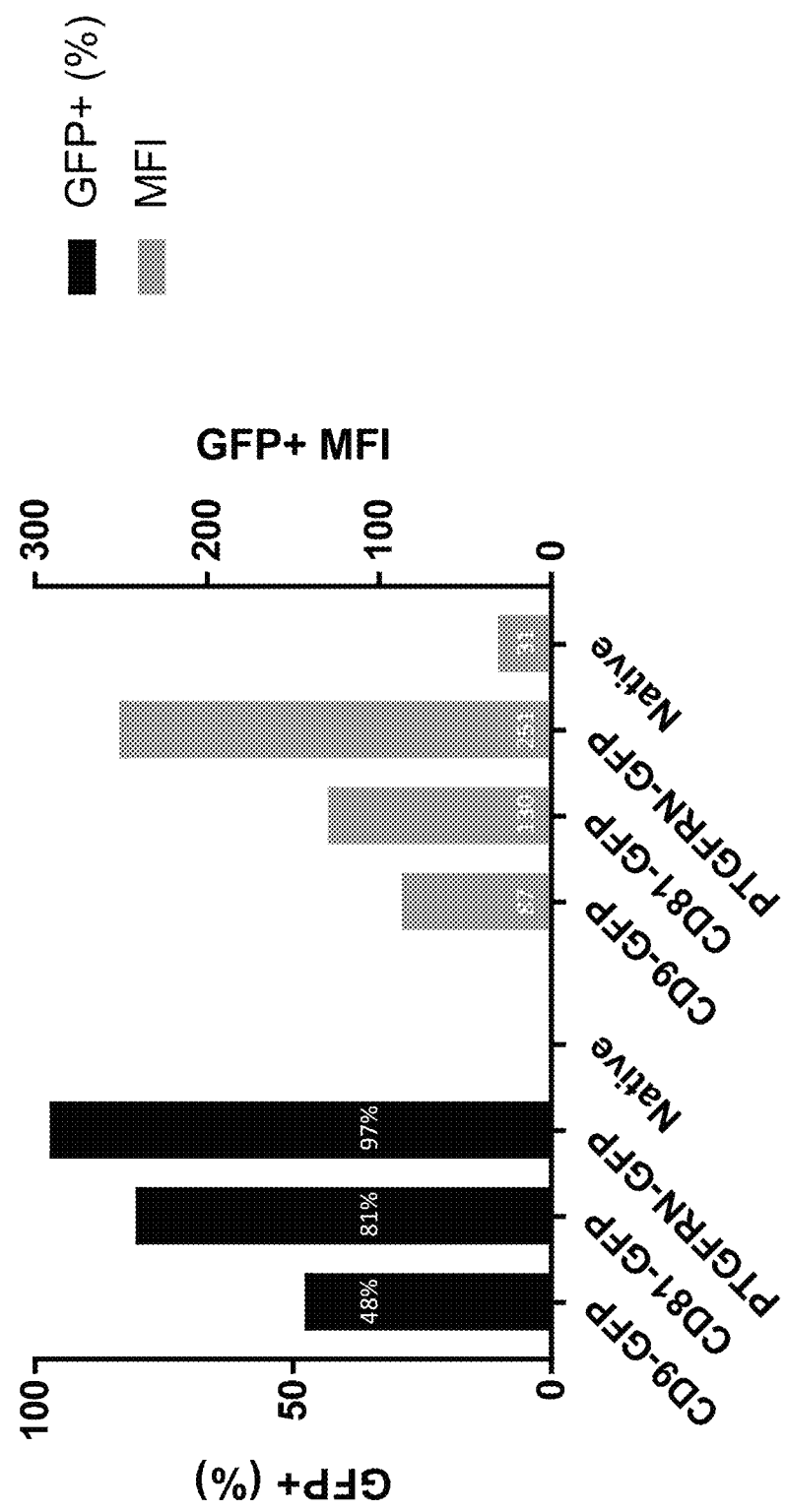

FIG. 38 is a graph providing percentages of GFP-positive particles (black bars, left y-axis) and mean fluorescent intensity (gray bars, right y-axis) in four different groups of exosomes—modified exosomes engineered to express (i) CD9-GFP, (ii) CD81-GFP, or (iii) PTGFRN-GFP, or (iv) unmodified, native exosomes.

Figure 39:
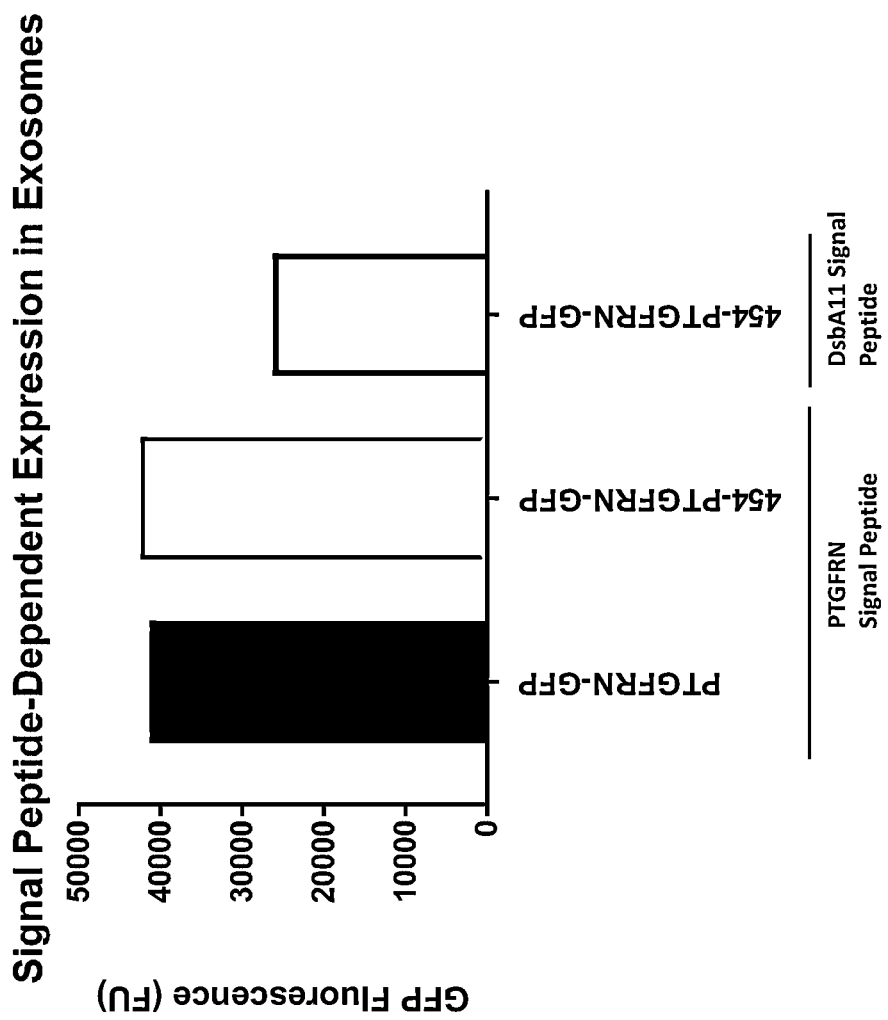

FIG. 39 provides GFP fluorescence intensity (FU) of modified exosomes expressing a GFP fusion protein containing a native PTGFRN (PTGFRN-GFP), a truncated PTGFRN (454-PTGFRN-GFP) with its own signal peptide or a truncated PTGFRN (454-PTGFRN-GFP) with a synthetic signal peptide from DsbA11.

Figure 40B:
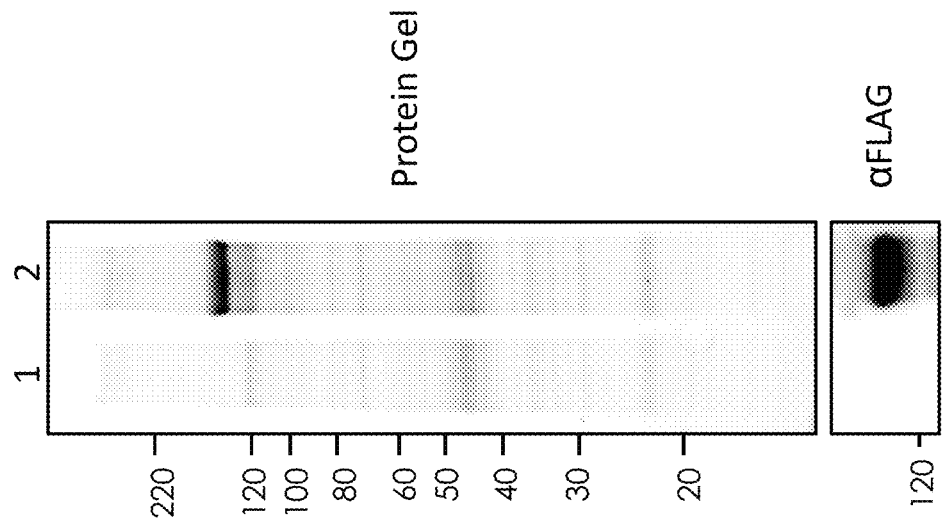
Figure 40A:
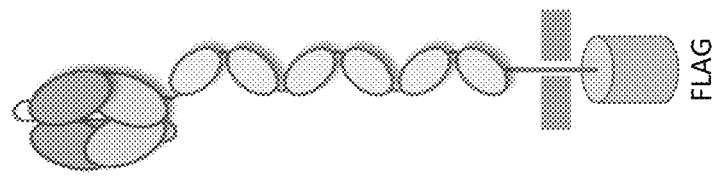

FIG. 40A shows a structure of a fusion protein consisting of a single chain Fab recognizing the lectin CLEC9A, a full-length PTGFRN, GFP, and a FLAG tag.

FIG. 40B provides a gel picture from western blotting Optiprep™ purified exosomes using anti-ALIX antibodies (top) or GFP antibodies (bottom).

Figure 41:
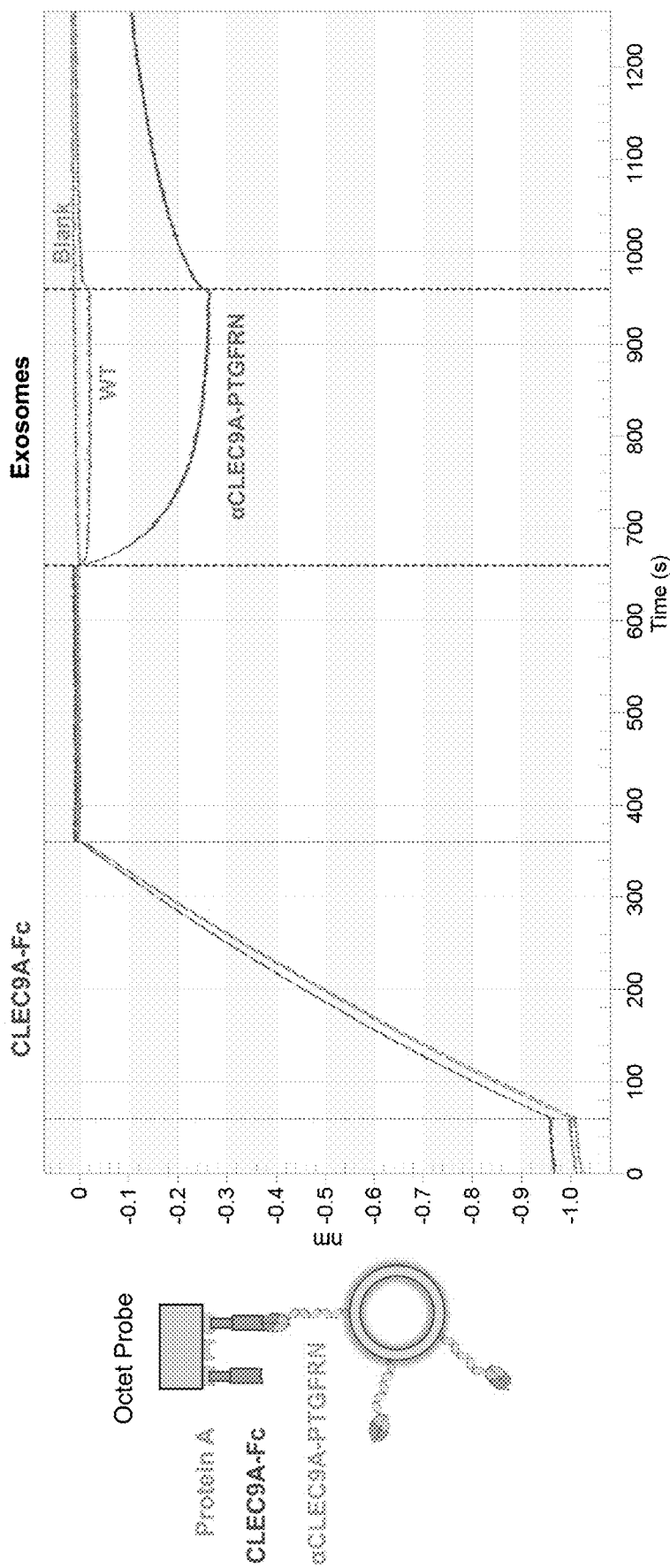

FIG. 41 provides BLI results for studying the interaction between CLEC9A-Fc and exosomes modified to express a fusion protein consisting of a single chain Fab recognizing the lectin CLEC9A, a full-length PTGFRN, GFP, and a FLAG tag ("αCLEC9A-PTGFRN").

Figure 42:
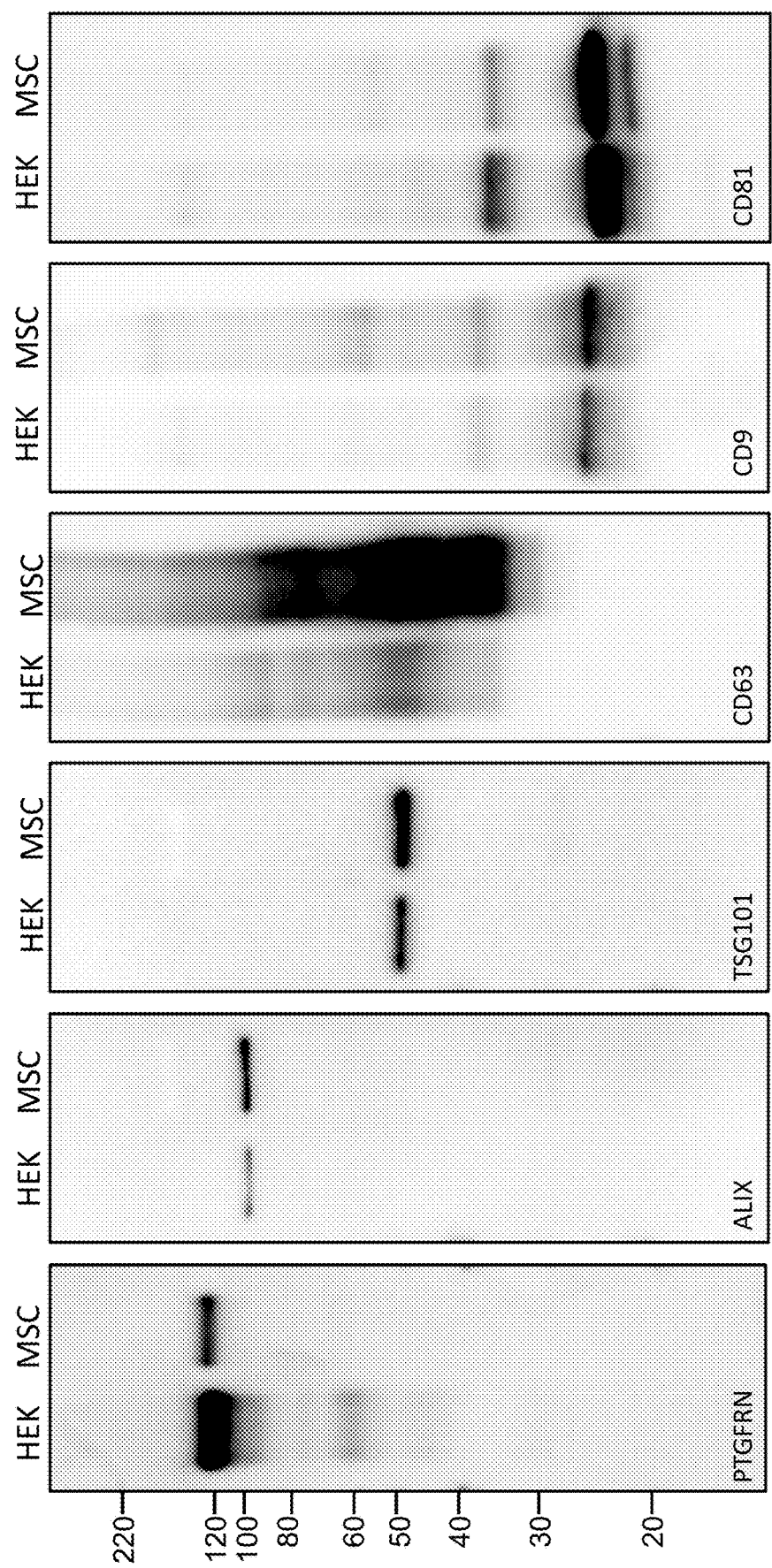

FIG. 42 provides gel pictures from western blotting exosomes purified from HEK293SF cells ("HEK") or MSCs ("MSC") with antibodies against PTGFRN, ALIX, TSG101, CD63, CD9, or CD81.

Figure 43C:
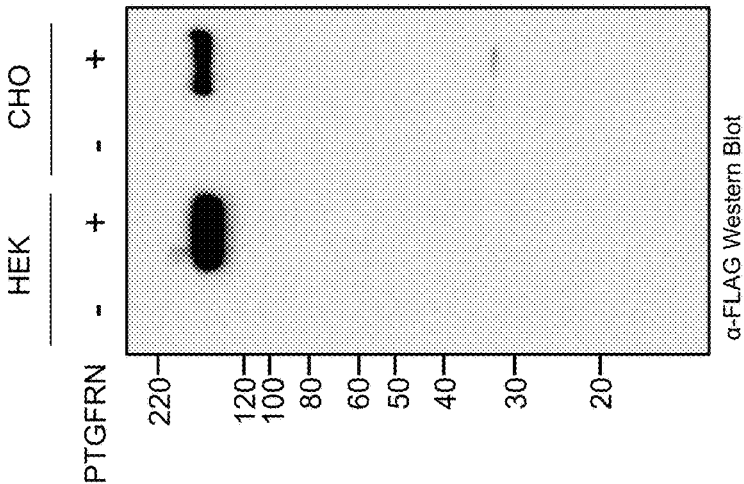
Figure 43B:
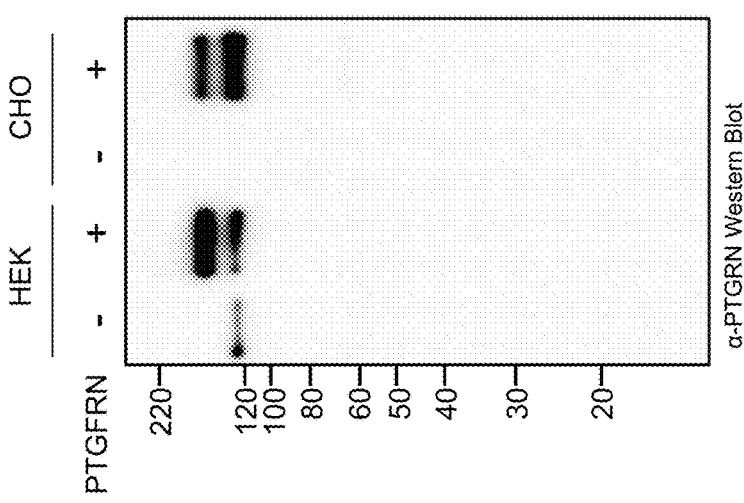
Figure 43A:
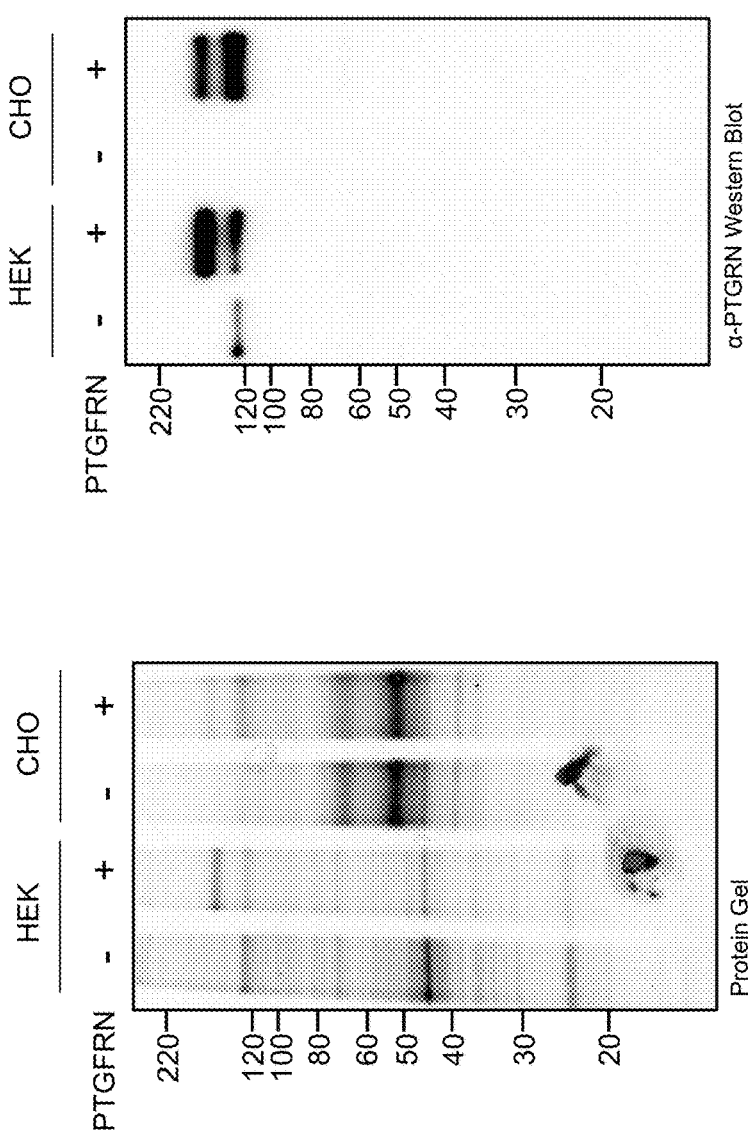

FIG. 43A provides a picture of a polyacrylamide gel running exosomes purified from untransfected HEK cells, HEK cells transfected with a plasmid expressing full-length PTGFRN fused to a FLAG tag ("the PTGFRN-FLAG plasmid"), untransfected CHO cells, or CHO cells transfected with the PTGFRN-FLAG plasmid.

FIG. 43B provides a gel picture from western blotting the samples from FIG. 43A using an antibody against PTGRN.

FIG. 43C provides a gel picture from western blotting the samples from FIG. 43A using an antibody against a FLAG tag.

Figure 44A:
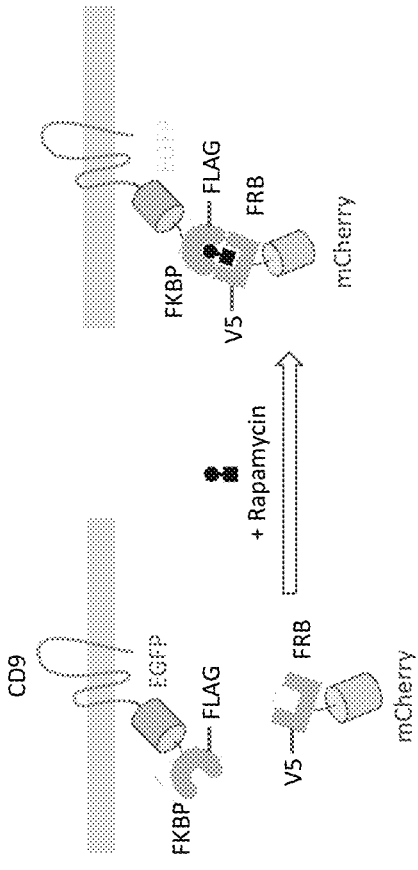
Figure 44B:
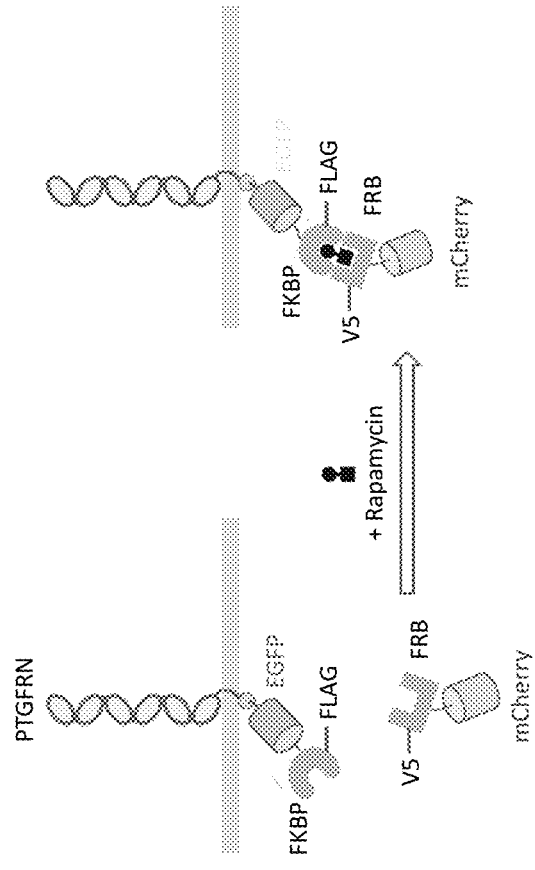

FIGS. 44A-B illustrates an experimental system for testing loading of a cargo protein in the exosome lumen using CD9 (FIG. 44A) or PTGFRN (FIG. 44B). FIG. 44A illustrates a cell expressing CD9 fused to GFP, a FLAG tag and FKBP, which can interact with mCherry fused to a V5 tag and FKBP in the presence of Rapamycin. FIG. 44B illustrates a cell expressing PTGFRN fused to GFP, a FLAG tag and FKBP, which can interact with mCherry fused to a V5 tag and FKBP in the presence of Rapamycin.

Figure 45B:
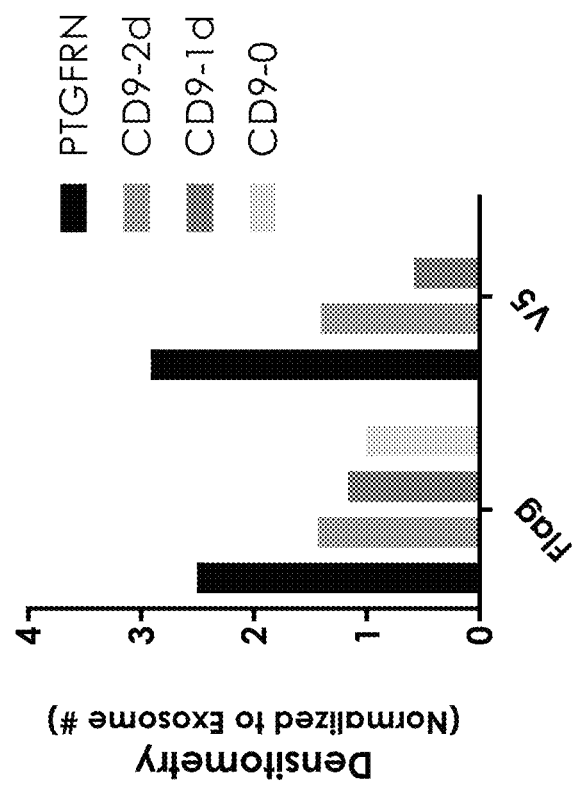
Figure 45A:
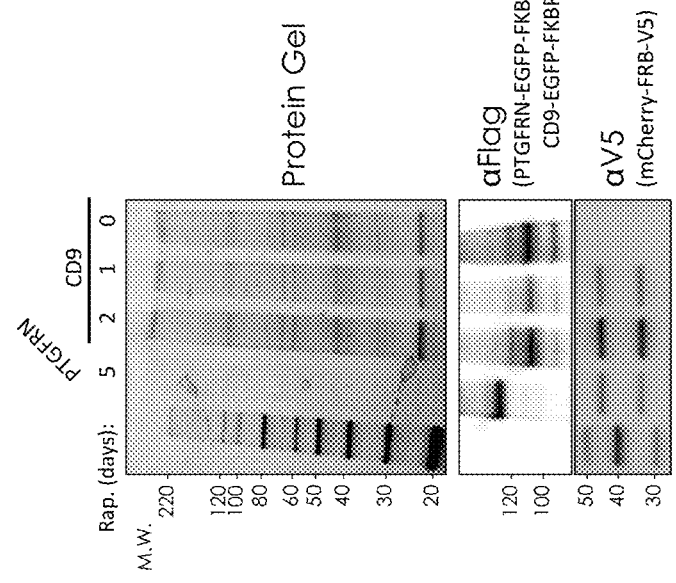

FIG. 45A provides a picture of a polyacrylamide gel running exosomes purified from the cell culture samples illustrated in FIG. 44A (CD9) or FIG. 44B (PTGFRN) (top). The figure also provides the Western blotting results using an antibody against FLAG (αFlag) or V5 (αV5) (bottom). FIG. 45B provides band intensities for FLAG and V5 from the Western blotting in FIG. 45A, measured by densitometry and normalized to the amount of collected exosomes.

6. DETAILED DESCRIPTION

6.1. Definitions

Unless defined otherwise, all technical and scientific terms used herein have the meaning commonly understood by a person skilled in the art to which this invention belongs. As used herein, the following terms have the meanings ascribed to them below.

As used herein, the term "extracellular vesicle" or "EV" refers to a cell-derived vesicle comprising a membrane that encloses an internal space. Extracellular vesicles comprise all membrane-bound vesicles that have a smaller diameter than the cell from which they are derived. Generally extracellular vesicles range in diameter from 20 nm to 1000 nm, and can comprise various macromolecular cargo either within the internal space, displayed on the external surface of the extracellular vesicle, and/or spanning the membrane. Said cargo can comprise nucleic acids, proteins, carbohydrates, lipids, small molecules, and/or combinations thereof. By way of example and without limitation, extracellular vesicles include apoptotic bodies, fragments of cells, vesicles derived from cells by direct or indirect manipulation (e.g., by serial extrusion or treatment with alkaline solutions), vesiculated organelles, and vesicles produced by living cells (e.g., by direct plasma membrane budding or fusion of the late endosome with the plasma membrane). Extracellular vesicles can be derived from a living or dead organism, explanted tissues or organs, and/or cultured cells.

As used herein the term "exosome" refers to a cell-derived small (between 20-300 nm in diameter, more preferably 40-200 nm in diameter) vesicle comprising a membrane that encloses an internal space, and which is generated from said cell by direct plasma membrane budding or by fusion of the late endosome with the plasma membrane. The exosome comprises lipid or fatty acid and polypeptide and optionally comprises a payload (e.g., a therapeutic agent), a receiver (e.g., a targeting moiety), a polynucleotide (e.g., a nucleic acid, RNA, or DNA), a sugar (e.g., a simple sugar, polysaccharide, or glycan) or other molecules. The exosome can be derived from a producer cell, and isolated from the producer cell based on its size, density, biochemical parameters, or a combination thereof. An exosome is a species of extracellular vesicle. Generally, exosome production/biogenesis does not result in the destruction of the producer cell.

As used herein, the term "nanovesicle" refers to a cell-derived small (between 20-250 nm in diameter, more preferably 30-150 nm in diameter) vesicle comprising a membrane that encloses an internal space, and which is generated from said cell by direct or indirect manipulation such that said nanovesicle would not be produced by said producer cell without said manipulation. Appropriate manipulations of said producer cell include but are not limited to serial extrusion, treatment with alkaline solutions, sonication, or combinations thereof. The production of nanovesicles may, in some instances, result in the destruction of said producer cell. Preferably, populations of nanovesicles are substantially free of vesicles that are derived from producer cells by way of direct budding from the plasma membrane or fusion of the late endosome with the plasma membrane. The nanovesicle comprises lipid or fatty acid and polypeptide, and optionally comprises a payload (e.g., a therapeutic agent), a receiver (e.g., a targeting moiety), a polynucleotide (e.g., a nucleic acid, RNA, or DNA), a sugar (e.g., a simple sugar, polysaccharide, or glycan) or other molecules. The nanovesicle, once it is derived from a producer cell according to said manipulation, may be isolated from the producer cell based on its size, density, biochemical parameters, or a combination thereof. A nanovesicle is a species of extracellular vesicle.

As used herein the term "surface-engineered exosome" refers to an exosome with a membrane modified in its composition. For example, the membrane is modified in its composition of a protein, a lipid, a small molecule, a carbohydrate, etc. The composition can be changed by a chemical, a physical, or a biological method or by being produced from a cell previously or concurrently modified by a chemical, a physical, or a biological method. Specifically, the composition can be changed by a genetic engineering or by being produced from a cell previously modified by genetic engineering.

As used herein the term "a modification" of a protein refers to a protein having at least 15% identify to the non-mutant amino acid sequence of the protein. A modification of a protein includes a fragment or a variant of the protein. A modification of a protein can further include chemical, or physical modification to a fragment or a variant of the protein.

As used herein the term "a fragment" of a protein refers to a protein that is N- and/or C-terminally deleted in comparison to the naturally occurring protein. Preferably, a fragment of PTGFRN, BSG, IGSF2, IGSF3, IGSF8, ITGB1, ITGA4, SLC3A2, or ATP transporter retains the ability to be specifically targeted to exosomes. Such a fragment is also referred to as "functional fragment". Whether a fragment is a functional fragment in that sense can be assessed by any art known methods to determine the protein content of exosomes including Western Blots, FACS analysis and fusions of the fragments with autofluorescent proteins like, e.g. GFP. In a particular embodiment the fragment of PTGFRN, BSG, IGSF2, IGSF3, IGSF8, ITGB1, ITGA4, SLC3A2, ATP transporter retains at least 50%, 60%, 70%, 80%, 90% or 100% of the ability of the naturally occurring PTGFRN, BSG, IGSF2, IGSF3, IGSF8, ITGB1, ITGA4, SLC3A2, or ATP transporter to be specifically targeted to exosomes.

As used herein the term "variant" of a protein refers to a protein that shares a certain amino acid sequence identity with another protein upon alignment by a method known in the art. A variant of a protein can include a substitution, insertion, deletion, frameshift or rearrangement in another protein. In a particular embodiment, the variant is a variant having at least 70% identity to PTGFRN, BSG, IGSF2, IGSF3, IGSF8, ITGB1, ITGA4, SLC3A2, ATP transporter or a fragment of PTGFRN, BSG, IGSF2, IGSF3, IGSF8, ITGB1, ITGA4, SLC3A2, or ATP transporter. In some embodiments variants or variants of fragments of PTGFRN share at least 70%, 80%, 85%, 90%, 95% or 99% sequence identity with PTGFRN according to SEQ ID NO: 1 or with a functional fragment thereof. In some embodiments variants or variants of fragments of BSG share at least 70%, 80%, 85%, 90%, 95% or 99% sequence identity with BSG according to SEQ ID NO: 9 or with a functional fragment thereof. In some embodiments variants or variants of fragments of IGSF2 share at least 70%, 80%, 85%, 90%, 95% or 99% sequence identity with IGSF2 according to SEQ ID NO: 34 or with a functional fragment thereof. In some embodiments variants or variants of fragments of IGSF3 share at least 70%, 80%, 85%, 90%, 95% or 99% sequence identity with IGSF3 according to SEQ ID NO: 20 or with a functional fragment thereof. In some embodiments variants or variants of fragments of IGSF8 share at least 70%, 80%, 85%, 90%, 95% or 99% sequence identity with IGSF8 according to SEQ ID NO: 14 or with a functional fragment thereof. In some embodiments variants or variants of fragments of ITGB1 share at least 70%, 80%, 85%, 90%, 95% or 99% sequence identity with ITGB1 according to SEQ ID NO: 21 or with a functional fragment thereof. In some embodiments variants or variants of fragments of ITGA4 share at least 70%, 80%, 85%, 90%, 95% or 99% sequence identity with ITGA4 according to SEQ ID NO: 22 or with a functional fragment thereof. In some embodiments variants or variants of fragments of SLC3A2 share at least 70%, 80%, 85%, 90%, 95% or 99% sequence identity with SLC3A2 according to SEQ ID NO: 23 or with a functional fragment thereof. In some embodiments variants or variants of fragments of ATP1A1 share at least 70%, 80%, 85%, 90%, 95% or 99% sequence identity with ATP1A1 according to SEQ ID NO: 24 or with a functional fragment thereof. In some embodiments variants or variants of fragments of ATP1A2 share at least 70%, 80%, 85%, 90%, 95% or 99% sequence identity with ATP1A2 according to SEQ ID NO: 25 or with a functional fragment thereof. In some embodiments variants or variants of fragments of ATP1A3 share at least 70%, 80%, 85%, 90%, 95% or 99% sequence identity with ATP1A3 according to SEQ ID NO: 26 or with a functional fragment thereof. In some embodiments variants or variants of fragments of ATP1A4 share at least 70%, 80%, 85%, 90%, 95% or 99% sequence identity with ATP1A4 according to SEQ ID NO: 27 or with a functional fragment thereof. In some embodiments variants or variants of fragments of ATP1B3 share at least 70%, 80%, 85%, 90%, 95% or 99% sequence identity with ATP1B3 according to SEQ ID NO: 28 or with a functional fragment thereof. In some embodiments variants or variants of fragments of ATP2B1 share at least 70%, 80%, 85%, 90%, 95% or 99% sequence identity with ATP2B1 according to SEQ ID NO: 29 or with a functional fragment thereof. In some embodiments variants or variants of fragments of ATP2B2 share at least 70%, 80%, 85%, 90%, 95% or 99% sequence identity with ATP2B2 according to SEQ ID NO: 30 or with a functional fragment thereof. In some embodiments variants or variants of fragments of ATP2B3 share at least 70%, 80%, 85%, 90%, 95% or 99% sequence identity with ATP2B3 according to SEQ ID NO: 31 or with a functional fragment thereof. In some embodiments variants or variants of fragments of ATP2B4 share at least 70%, 80%, 85%, 90%, 95% or 99% sequence identity with ATP2B4 according to SEQ ID NO: 32 or with a functional fragment thereof. In each of above cases, it is preferred that the variant or variant of a fragment retains the ability to be specifically targeted to exosomes.

Methods of alignment of sequences for comparison are well-known in the art. Various programs and alignment algorithms are described in: Smith and Waterman, Adv. Appl. Math. 2: 482 (1981); Needleman and Wunsch, J. Mol. Bio. 48: 443 (1970); Pearson and Lipman, Methods in Mol. Biol. 24: 307-31 (1988); Higgins and Sharp, Gene 73: 15 237-44 (1988); Higgins and Sharp, CABIOS 5: 151-3 (1989) Corpet et al., Nuc. Acids Res. 16: 10881-90 (1988); Huang et al., Comp. Appl. BioSci. 8: 155-65 (1992); and Pearson et al., Meth. Mol. Biol. 24: 307-31 (1994). The NCBI Basic Local Alignment Search Tool (BLAST) [Altschul 20 et al., J. Mol. Biol. 215: 403-10 (1990) J is available from several sources, including the National Center for Biological Information (NBCl, Bethesda, Md.) and on the Internet, for use in connection with the sequence analysis programs blastp, blasm, blastx, tblastn and tblastx. BLAST and a description of how to determine sequence identify using the program can be accessed at the official website of NCBI (National Center for Biotechnology Information) under NIH (National Institute of Health).

Recitation of any protein provided herein encompasses a functional variant of the protein. The term "functional variant" of a protein refers to a variant of the protein that retains the ability to be specifically targeted to exosomes.

As used herein the term "producer cell" refers to a cell used for generating an exosome. A producer cell can be a cell cultured in vitro, or a cell in vivo. A producer cell includes, but is not limited to, a cell known to be effective in generating exosomes, e.g., HEK293 cells, Chinese hamster ovary (CHO) cells, and mesenchymal stem cells (MSCs).

As used herein the term "target protein" refers to a protein that can be targeted to the surface of an exosome. The target protein can be a non-mutant protein that is naturally targeted to an exosome membrane, or a fragment or a variant of the non-mutant protein. The target protein can be a fusion protein containing a flag tag, a therapeutic peptide, a targeting moiety, or other peptide attached to the non-mutant protein or a variant or a fragment of the non-mutant protein. The target protein can comprise a transmembrane protein, an integral protein, a peripheral protein, or a soluble protein attached to the membrane by a linker.

As used herein the term "contaminant protein" refers to a protein that is not associated with an exosome. For example, a contaminant protein includes a protein, not enclosed in the exosome and not attached to or incorporated into the membrane of the exosome.

As used herein, the terms "isolate," "isolated," and "isolating" or "purify," "purified," and "purifying" as well as "extracted" and "extracting" are used interchangeably and refer to the state of a preparation (e.g., a plurality of known or unknown amount and/or concentration) of desired EVs, that have undergone one or more processes of purification, e.g., a selection or an enrichment of the desired exosome preparation. In some embodiments, isolating or purifying as used herein is the process of removing, partially removing (e.g., a fraction) of the exosomes from a sample containing producer cells. In some embodiments, an isolated exosome composition has no detectable undesired activity or, alternatively, the level or amount of the undesired activity is at or below an acceptable level or amount. In other embodiments, an isolated exosome composition has an amount and/or concentration of desired exosomes at or above an acceptable amount and/or concentration. In other embodiments, the isolated exosome composition is enriched as compared to the starting material (e.g., producer cell preparations) from which the composition is obtained. This enrichment can be by 10%, 20%, 30%, 40%, 50%, 60%, 70%, 80%, 90%, 95%, 96%, 97%, 98%, 99%, 99.9%, 99.99%, 99.999%, 99.9999%, or greater than 99.9999% as compared to the starting material. In some embodiments, isolated exosome preparations are substantially free of residual biological products. In some embodiments, the isolated exosome preparations are 100% free, 99% free, 98% free, 97% free, 96% free, 95% free, 94% free, 93% free, 92% free, 91% free, or 90% free of any contaminating biological matter. Residual biological products can include abiotic materials (including chemicals) or unwanted nucleic acids, proteins, lipids, or metabolites. Substantially free of residual biological products can also mean that the exosome composition contains no detectable producer cells and that only exosomes are detectable.

The term "excipient" or "carrier" refers to an inert substance added to a pharmaceutical composition to further facilitate administration of a compound. The term "pharmaceutically-acceptable carrier" or "pharmaceutically-acceptable excipient" encompasses any of the agents approved by a regulatory agency of the US Federal government or listed in the US Pharmacopeia for use in animals, including humans, as well as any carrier or diluent that does not cause significant irritation to a subject and does not abrogate the biological activity and properties of the administered compound. Included are excipients and carriers that are useful in preparing a pharmaceutical composition and are generally safe, non-toxic, and desirable.

As used herein, the term "payload" refers to a therapeutic agent that acts on a target (e.g., a target cell) that is contacted with the EV. Payloads that can be introduced into an exosome and/or a producer cell include therapeutic agents such as, nucleotides (e.g., nucleotides comprising a detectable moiety or a toxin or that disrupt transcription), nucleic acids (e.g., DNA or mRNA molecules that encode a polypeptide such as an enzyme, or RNA molecules that have regulatory function such as miRNA, dsDNA, lncRNA, and siRNA), amino acids (e.g., amino acids comprising a detectable moiety or a toxin or that disrupt translation), polypeptides (e.g., enzymes), lipids, carbohydrates, and small molecules (e.g., small molecule drugs and toxins).

As used herein, "a mammalian subject" includes all mammals, including without limitation, humans, domestic animals (e.g., dogs, cats and the like), farm animals (e.g., cows, sheep, pigs, horses and the like) and laboratory animals (e.g., monkey, rats, mice, rabbits, guinea pigs and the like).

The terms "individual," "subject," "host," and "patient," are used interchangeably herein and refer to any mammalian subject for whom diagnosis, treatment, or therapy is desired, particularly humans. The methods described herein are applicable to both human therapy and veterinary applications. In some embodiments, the subject is a mammal, and in other embodiments the subject is a human.

As used herein, the term "substantially free" means that the sample comprising exosomes comprise less than 10% of macromolecules by mass/volume (m/v) percentage concentration. Some fractions may contain less than 0.001%, less than 0.01%, less than 0.05%, less than 0.1%, less than 0.2%, less than 0.3%, less than 0.4%, less than 0.5%, less than 0.6%, less than 0.7%, less than 0.8%, less than 0.9%, less than 1%, less than 2%, less than 3%, less than 4%, less than 5%, less than 6%, less than 7%, less than 8%, less than 9%, or less than 10% (m/v) of macromolecules.

As used herein, the term "macromolecule" means nucleic acids, contaminant proteins, lipids, carbohydrates, metabolites, or a combination thereof.

As used herein, the term "conventional exosome protein" means a protein previously known to be enriched in exosomes, including but is not limited to CD9, CD63, CD81, PDGFR, GPI anchor proteins, lactadherin LAMP2, and LAMP2B, a fragment thereof, or a peptide that binds thereto.

6.2. Other Interpretational Conventions

Ranges recited herein are understood to be shorthand for all of the values within the range, inclusive of the recited endpoints. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

6.3. Exosome Proteins

An aspect of the present invention relates to identification, use and modification of exosome proteins, which are highly enriched on exosome membranes. Such exosome proteins can be identified by analyzing highly purified exosomes with mass spectrometry or other methods known in the art.

The exosome proteins include various membrane proteins, such as transmembrane proteins, integral proteins and peripheral proteins, enriched on the exosome membranes. They include various CD proteins, transporters, integrins, lectins and cadherins. Specifically, the proteins include, but are not limited to, (1) prostaglandin F2 receptor negative regulator (PTGFRN), (2) basigin (BSG), (3) immunoglobulin superfamily member 3 (IGSF3), (4) immunoglobulin superfamily member 8 (IGSF8), (5) integrin beta-1 (ITGB1), (6) integrin alpha-4 (ITGA4), (7) 4F2 cell-surface antigen heavy chain (SLC3A2), (8) a class of ATP transporter proteins (ATP1A1, ATP1A2, ATP1A3, ATP1A4, ATP1B3, ATP2B1, ATP2B2, ATP2B3, ATP2B4), and (9), immunoglobulin superfamily member 2 (IGSF2).

One or more exosome proteins identified herein can be selectively used depending on a producer cell, production condition, purification methods, or intended application of the exosomes. For example, exome proteins enriched on a specific population of exosomes can be used to purify the specific population of exosomes. Exosome proteins enriched on the surface of certain exosomes with a specific size range, a targeting moiety, a charge density, a payload, etc. can be identified and used in some embodiments of the present invention. In some embodiments, more than one exosome proteins can be used concurrently or subsequently for generation, purification, and isolation of therapeutic exosomes.

6.4. Surface-Engineered Exosomes

Another aspect of the present invention relates to generation and use of surface-engineered exosomes. Surface-engineered exosomes have a membrane modified in its compositions. For example, their membrane compositions can be modified by changing the protein, lipid or glycan content of the membrane.

In some embodiments, the surface-engineered exosomes are generated by chemical and/or physical methods, such as PEG-induced fusion and/or ultrasonic fusion.

In other embodiments, the surface-engineered exosomes are generated by genetic engineering. Exosomes produced from a genetically-modified producer cell or a progeny of the genetically-modified cell can contain modified membrane compositions. In some embodiments, surface-engineered exosomes have the exosome protein at a higher or lower density or include a variant or a fragment of the exosome protein.

For example, surface-engineered exosomes can be produced from a cell transformed with an exogenous sequence encoding the exosome protein or a variant or a fragment of the exosome protein. Exosomes including proteins expressed from the exogenous sequence can include modified membrane protein compositions.

Various modifications or fragments of the exosome protein can be used for the embodiments of the present invention. For example, proteins modified to have enhanced affinity to a binding agent can be used for generating surface-engineered exosomes that can be purified using the binding agent. Proteins modified to be more effectively targeted to exosomes and/or membranes can be used. Proteins modified to comprise a minimal fragment required for specific and effective targeting to exosome membranes can be also used.

Fusion proteins can be also used, for example, exosome proteins or their fragments fused to an affinity tag (e.g., His tag, GST tag, glutathione-S-transferase, S-peptide, HA, Myc, FLAG™ (Sigma-Aldrich Co.), MBP, SUMO, and Protein A) can be used for purification or removal of the surface-engineered exosomes with a binding agent specific to the affinity tag.

Fusion proteins having a therapeutic activity can be also used for generating surface-engineered exosomes. For example, the fusion protein can comprise PTGFRN, BSG, IGSF2, IGSF3, IGSF8, ITGB1, ITGA4, SLC3A2, ATP transporter, or a fragment or a variant thereof, and a therapeutic peptide. The therapeutic peptide is selected from the group consisting of a natural peptide, a recombinant peptide, a synthetic peptide, or a linker to a therapeutic compound. The therapeutic compound can be nucleotides, amino acids, lipids, carbohydrates, or small molecules. The therapeutic peptide can be an antibody, an enzyme, a ligand, a receptor, an antimicrobial peptide or a fragment or a variant thereof. In some embodiments, the therapeutic peptide is a nucleic acid binding protein. The nucleic acid binding protein can be Dicer, an Argonaute protein, TRBP, or MS2 bacteriophage coat protein. In some embodiments, the nucleic acid binding protein additionally comprises one or more RNA or DNA molecules. The one or more RNA can be a miRNA, siRNA, guide RNA, lincRNA, mRNA, antisense RNA, dsRNA, or combinations thereof.

In some embodiments, the therapeutic peptide is a part of a protein-protein interaction system. In some embodiments, the protein-protein interaction system comprises an FRB-FKBP interaction system, e.g., the FRB-FKBP interaction system as described in Banaszynski et al., J Am Chem Soc. 2005 Apr. 6; 127(13):4715-21.

The fusion proteins can be targeted to the surface of exosomes and provide a therapeutic activity to the exosome. In some embodiments, the fusion protein does not comprise IGSF8 or a fragment or modification thereof.

In some embodiments, fusion proteins having a targeting moiety are used. For example, fusion proteins can comprise PTGFRN, BSG, IGSF2, IGSF3, IGSF8, ITGB1, ITGA4, SLC3A2, ATP transporter, or a fragment or a variant thereof, and a targeting moiety. The targeting moiety can be used for targeting the exosome to a specific organ, tissue, or cell for a treatment using the exosome. In some embodiments, the targeting moiety is an antibody or antigen-binding fragment thereof. Antibodies and antigen-binding fragments thereof include whole antibodies, polyclonal, monoclonal and recombinant antibodies, fragments thereof, and further includes single-chain antibodies, humanized antibodies, murine antibodies, chimeric, mouse-human, mouse-primate, primate-human monoclonal antibodies, anti-idiotype antibodies, antibody fragments, such as, e.g., scFv, (scFv)$_2$, Fab, Fab', and F(ab')$_2$, F(ab1)$_2$, Fv, dAb, and Fd fragments, diabodies, and antibody-related polypeptides. Antibodies and antigen-binding fragments thereof also includes bispecific antibodies and multispecific antibodies so long as they exhibit the desired biological activity or function.

In some embodiments, the fusion protein does not comprise IGSF8 or a fragment or modification thereof.

In some embodiments, the surface-engineered exosomes described herein demonstrate superior characteristics compared to surface-engineered exosomes known in the art. For example, surface-engineered exosomes produced by using the newly-identified exosome proteins provided herein contain modified proteins more highly enriched on their surface than exosomes in prior art, e.g., those produced using conventional exosome proteins. Moreover, the surface-engineered exosomes of the present invention can have greater, more specific, or more controlled biological activity compared to surface-engineered exosomes known in the art. For example, a surface engineered exosome comprising a therapeutic or biologically relevant exogenous sequence fused to an exosome surface protein or a fragment thereof described herein (e.g., PTGFRN or a fragment thereof) can have more of the desired engineered characteristics than fusion to scaffolds known in the art. Scaffold proteins known in the art include tetraspanin molecules (e.g., CD63, CD81, CD9 and others), lysosome-associated membrane protein 2 (LAMP2 and LAMP2B), platelet-derived growth factor receptor (PDGFR), GPI anchor proteins, lactadherin and fragments thereof, and peptides that have affinity to any of these proteins or fragments thereof. Previously, overexpression of exogenous proteins relied on stochastic or random disposition of the exogenous proteins onto the exosome for producing surface-engineered exosomes. This resulted in low-level, unpredictable density of the exogenous proteins on exosomes. Thus, the exosome surface proteins and fragments thereof described herein provide important advancements in novel exosome compositions and methods of making the same.

In some embodiments, the surface-engineered exosome comprising a fusion protein containing an exogenous sequence and an exosome surface protein newly-identified herein has a higher density of the fusion protein than similarly engineered exosomes comprising an exogenous sequence conjugated to a conventional exosome protein known in the art (e.g., CD9, CD63, CD81, PDGFR, GPI anchor proteins, lactadherin LAMP2, and LAMP2B, a fragment thereof, or a peptide that binds thereto). In some embodiments, said fusion protein containing an exosome protein newly-identified herein is present at 2-, 4-, 8-, 16-, 32-, 64-, 100-, 200-, 400-, 800-, 1,000-fold or a higher density on the exosome surface than fusion proteins on other exosome surfaces similarly modified using a conventional exosome protein. In some embodiments, said fusion protein containing an exosome protein newly-identified herein is present at 2 to 4-fold, 4 to 8-fold, 8 to 16-fold, 16 to 32-fold, 32 to 64-fold, 64 to 100-fold, 100 to 200-fold, 200 to 400-fold, 400 to 800-fold, 800 to 1,000-fold or to a higher density on the exosome surface than fusion proteins on other exosome surfaces similarly modified using a conventional exosome protein.

In some embodiments, a fusion protein of PTGFRN, a variant, a fragment, a variant of a fragment or a modification thereof is present at 2-, 4-, 8-, 16-, 32-, 64-, 100-, 200-, 400-, 800-, 1,000-fold or a higher density on the exosome surface than fusion proteins on other exosome surfaces similarly modified using CD9. In some embodiments, a fusion protein of PTGFRN, a variant, a fragment, a variant of a fragment or a modification thereof is present at 2-, 4-, 8-, 16-, 32-, 64-, 100-, 200-, 400-, 800-, 1,000-fold or a higher density on the exosome surface than fusion proteins on other exosome surfaces similarly modified using CD63. In some embodiments, a fusion protein of PTGFRN, a variant, a fragment, a variant of a fragment or a modification thereof is present at 2-, 4-, 8-, 16-, 32-, 64-, 100-, 200-, 400-, 800-, 1,000-fold or a higher density on the exosome surface than fusion proteins on other exosome surfaces similarly modified using CD81. In some embodiments, a fusion protein of PTGFRN, a variant, a fragment, a variant of a fragment or a modification thereof is present at 2-, 4-, 8-, 16-, 32-, 64-, 100-, 200-, 400-, 800-, 1,000-fold or a higher density on the exosome surface than fusion proteins on other exosome surfaces similarly modified using PDGFR. In some embodiments, a fusion protein of PTGFRN, a variant, a fragment, a variant of a fragment or a modification thereof is present at 2-, 4-, 8-, 16-, 32-, 64-, 100-, 200-, 400-, 800-, 1,000-fold or a higher density on the exosome surface than fusion proteins on other exosome surfaces similarly modified using GPI anchor proteins. In some embodiments, a fusion protein of PTGFRN, a variant, a fragment, a variant of a fragment or a modification thereof is present at 2-, 4-, 8-, 16-, 32-, 64-, 100-, 200-, 400-, 800-, 1,000-fold or a higher density on the exosome surface than fusion proteins on other exosome surfaces similarly modified using lactadherin. In some embodiments, a fusion protein of PTGFRN, a variant, a fragment, a variant of a fragment or a modification thereof is present at 2-, 4-, 8-, 16-, 32-, 64-, 100-, 200-, 400-, 800-, 1,000-fold or a higher density on the exosome surface than fusion proteins on other exosome surfaces similarly modified using LAMP2. In some embodiments, a fusion protein of PTGFRN, a variant, a fragment, a variant of a fragment or a modification thereof is present at 2-, 4-, 8-, 16-, 32-, 64-, 100-, 200-, 400-, 800-, 1,000-fold or a higher density on the exosome surface than fusion proteins on other exosome surfaces similarly modified using LAMP2B. In some embodiments, a fusion protein of PTGFRN, a variant, a fragment, a variant of a fragment or a modification thereof is present at 2-, 4-, 8-, 16-, 32-, 64-, 100-, 200-, 400-, 800-, 1,000-fold or a higher density on the exosome surface than fusion proteins on other exosome surfaces similarly modified using a fragment of a conventional exosome protein. In some embodiments, a fusion protein of PTGFRN, a variant, a fragment, a variant of a fragment or a modification thereof is present at 2-, 4-, 8-, 16-, 32-, 64-, 100-, 200-, 400-, 800-, 1,000-fold or a higher density on the exosome surface than fusion proteins on other exosome surfaces similarly modified using a variant of a conventional exosome protein.

In particular embodiments a fusion protein of PTGFRN, a variant, a fragment, a variant of a fragment or a modification thereof is present at 2-, 4-, 8-, 16-, 32-, 64-, 100-, 200-, 400-, 800-, 1,000-fold or a higher density on the exosome surface than fusion proteins on other exosome surfaces similarly modified using a conventional exosome protein (e.g., a tetraspanin molecule, like CD63). In particular embodiments a fusion protein of BSG, a variant, a fragment, a variant of a fragment or a modification thereof is present at 2-, 4-, 8-, 16-, 32-, 64-, 100-, 200-, 400-, 800-, 1,000-fold or a higher density on the exosome surface than fusion proteins on other exosome surfaces similarly modified using a conventional exosome protein (e.g., a tetraspanin molecule, like CD63). In particular embodiments a fusion protein of IGSF2, a variant, a fragment, a variant of a fragment or a modification thereof is present at 2-, 4-, 8-, 16-, 32-, 64-, 100-, 200-, 400-, 800-, 1,000-fold or a higher density on the exosome surface than fusion proteins on other exosome surfaces similarly modified using a conventional exosome protein (e.g., a tetraspanin molecule, like CD63). In particular embodiments a fusion protein of IGSF3, a variant, a fragment, a variant of a fragment or a modification thereof is present at 2-, 4-, 8-, 16-, 32-, 64-, 100-, 200-, 400-, 800-, 1,000-fold or a higher density on the exosome surface than fusion proteins on other exosome surfaces similarly modified using a conventional exosome protein (e.g., a tetraspanin molecule, like CD63). In particular embodiments a fusion protein of IGSF8, a variant, a fragment, a variant of a fragment or a modification thereof is present at 2-, 4-, 8-, 16-, 32-, 64-, 100-, 200-, 400-, 800-, 1,000-fold or a higher density on the exosome surface than fusion proteins on other exosome surfaces similarly modified using a conventional exosome protein (e.g., a tetraspanin molecule, like CD63). In particular embodiments a fusion protein of ITGB1, a variant, a fragment, a variant of a fragment or a modification thereof is present at 2-, 4-, 8-, 16-, 32-, 64-, 100-, 200-, 400-, 800-, 1,000-fold or a higher density on the exosome surface than fusion proteins on other exosome surfaces similarly modified using a conventional exosome protein (e.g., a tetraspanin molecule, like CD63). In particular embodiments a fusion protein of ITGA4, a variant, a fragment, a variant of a fragment or a modification thereof is present at 2-, 4-, 8-, 16-, 32-, 64-, 100-, 200-, 400-, 800-, 1,000-fold or a higher density on the exosome surface than fusion proteins on other exosome surfaces similarly modified using a conventional exosome protein (e.g., a tetraspanin molecule, like CD63). In particular embodiments a fusion protein of SLC3A2, a variant, a fragment, a variant of a fragment or a modification thereof is present at 2-, 4-, 8-, 16-, 32-, 64-, 100-, 200-, 400-, 800-, 1,000-fold or a higher density on the exosome surface than fusion proteins on other exosome surfaces similarly modified using a conventional exosome protein (e.g., a tetraspanin molecule, like CD63). In particular embodiments a fusion protein of ATP transporter, a variant, a fragment, a variant of a fragment or a modification thereof is present at 2-, 4-, 8-, 16-, 32-, 64-, 100-, 200-, 400-, 800-, 1,000-fold or a higher density on the exosome surface than fusion proteins on other exosome surfaces similarly modified using a conventional exosome protein (e.g., a tetraspanin molecule, like CD63). In some embodiments, said fusion protein containing an exosome protein newly-identified herein is present at 2 to 4-fold, 4 to 8-fold, 8 to 16-fold, 16 to 32-fold, 32 to 64-fold, 64 to 100-fold, 100 to 200-fold, 200 to 400-fold, 400 to 800-fold, 800 to 1,000-fold or to a higher density on the exosome surface than fusion proteins on other exosome surfaces similarly modified using a conventional exosome protein.

Fusion proteins provided herein can comprise PTGFRN, BSG, IGSF2, IGSF3, IGSF8, ITGB1, ITGA4, SLC3A2, ATP transporter, or a fragment or a variant thereof, and an additional peptide. The additional peptide can be attached to either the N terminus or the C terminus of the exosome protein or a fragment or a variant thereof. The additional peptide can be located inside (in the luminal side) or outside of the exosome attached to the exosome protein.

In some embodiments, fusion proteins provided herein comprise PTGFRN, BSG, IGSF2, IGSF3, IGSF8, ITGB1, ITGA4, SLC3A2, ATP transporter, or a fragment or a variant thereof, and two additional peptides. Both of the two additional peptides can be attached to either the N terminus or the C terminus of the exosome protein or a fragment or a variant thereof. In some embodiments, one of the two additional peptides is attached to the N terminus and the other of the two additional peptides is attached to the C terminus of the exosome protein or a fragment or a variant thereof. The additional peptides can be located inside (in the luminal side) or outside of the exosome attached to the exosome protein, or both.

6.5. Producer Cell for Production of Surface-Engineered Exosomes

Exosomes of the present invention can be produced from a cell grown in vitro or a body fluid of a subject. When exosomes are produced from in vitro cell culture, various producer cells, e.g., HEK293 cells, Chinese hamster ovary (CHO) cells, or mesenchymal stem cells (MSCs), can be used for the present invention.

The producer cell can be genetically modified to comprise one or more exogenous sequences to produce surface-engineered exosomes. The genetically-modified producer cell can contain the exogenous sequence introduced by transient or stable transformation. The exogenous sequence can be introduced to the producer cell as a plasmid. The exogenous sequences can be stably integrated into a genomic sequence of the producer cell, at a targeted site or in a random site. In some embodiments, a stable cell line is generated for production of surface-engineered exosomes.

The exogenous sequences can be inserted into a genomic sequence of the producer cell, located within, upstream (5'-end) or downstream (3'-end) of an endogenous sequence encoding the exosome protein. Various methods known in the art can be used for the introduction of the exogenous sequences into the producer cell. For example, cells modified using various gene editing methods (e.g., methods using a homologous recombination, transposon-mediated system, loxP-Cre system, CRISPR/Cas9 or TALEN) are within the scope of the present invention.

The exogenous sequences can comprise a sequence encoding the exosome protein or a variant or a fragment of the exosome protein. An extra copy of the sequence encoding the exosome protein can be introduced to produce a surface-engineered exosome having the exosome protein at a higher density. An exogenous sequence encoding a variant or a fragment of the exosome protein can be introduced to produce a surface-engineered exosome containing the modification or the fragment of the exosome protein. An exogenous sequence encoding an affinity tag can be introduced to produce a surface-engineered exosome containing a fusion protein comprising the affinity tag attached to the exosome protein.

In some embodiments, a surface-engineered exosome has a higher density of the exosome protein than native exosomes isolated from the same or similar producer cell types. In some embodiments, said exosome protein is present at 2-, 4-, 8-, 16-, 32-, 64-, 100-, 200-, 400-, 800-, 1,000-fold or to a higher density on said surface-engineered exosome than said native exosome. In some embodiments, said exosome protein is present at 2 to 4-fold, 4 to 8-fold, 8 to 16-fold, 16 to 32-fold, 32 to 64-fold, 64 to 100-fold, 100 to 200-fold, 200 to 400-fold, 400 to 800-fold, 800 to 1,000-fold or to a higher density on said surface-engineered exosome than said native exosome. In some embodiments, a fusion protein comprising the exosome protein is present at 2 to 4-fold, 4 to 8-fold, 8 to 16-fold, 16 to 32-fold, 32 to 64-fold, 64 to 100-fold, 100 to 200-fold, 200 to 400-fold, 400 to 800-fold, 800 to 1,000-fold or to a higher density on said surface-engineered exosome than the unmodified exosome protein on said native exosome. In some embodiments, a fragment or a variant of the exosome protein is present at 2 to 4-fold, 4 to 8-fold, 8 to 16-fold, 16 to 32-fold, 32 to 64-fold, 64 to 100-fold, 100 to 200-fold, 200 to 400-fold, 400 to 800-fold, 800 to 1,000-fold or to a higher density on said surface-engineered exosome than the unmodified exosome protein on said native exosome.

In particular embodiments, PTGFRN, a fragment or a variant of PTGFRN, or a modification thereof is present at 2 to 4-fold, 4 to 8-fold, 8 to 16-fold, 16 to 32-fold, 32 to 64-fold, 64 to 100-fold, 100 to 200-fold, 200 to 400-fold, 400 to 800-fold, 800 to 1,000-fold or to a higher density on said surface-engineered exosome than the unmodified PTGFRN on said native exosome. In particular embodiments, BSG, a fragment or a variant of BSG, or a modification thereof is present at 2 to 4-fold, 4 to 8-fold, 8 to 16-fold, 16 to 32-fold, 32 to 64-fold, 64 to 100-fold, 100 to 200-fold, 200 to 400-fold, 400 to 800-fold, 800 to 1,000-fold or to a higher density on said surface-engineered exosome than the unmodified BSG on said native exosome. In particular embodiments, IGSF2, a fragment or a variant of IGSF2, or a modification thereof is present at 2 to 4-fold, 4 to 8-fold, 8 to 16-fold, 16 to 32-fold, 32 to 64-fold, 64 to 100-fold, 100 to 200-fold, 200 to 400-fold, 400 to 800-fold, 800 to 1,000-fold or to a higher density on said surface-engineered exosome than the unmodified IGSF2 on said native exosome. In particular embodiments, IGSF3, a fragment or a variant of IGSF3, or a modification thereof is present at 2 to 4-fold, 4 to 8-fold, 8 to 16-fold, 16 to 32-fold, 32 to 64-fold, 64 to 100-fold, 100 to 200-fold, 200 to 400-fold, 400 to 800-fold, 800 to 1,000-fold or to a higher density on said surface-engineered exosome than the unmodified IGSF3 on said native exosome. In particular embodiments, ITGB1, a fragment or a variant of ITGB1, or a modification thereof is present at 2 to 4-fold, 4 to 8-fold, 8 to 16-fold, 16 to 32-fold, 32 to 64-fold, 64 to 100-fold, 100 to 200-fold, 200 to 400-fold, 400 to 800-fold, 800 to 1,000-fold or to a higher density on said surface-engineered exosome than the unmodified ITGB1 on said native exosome. In particular embodiments, ITGA4, a fragment or a variant of ITGA4, or a modification thereof is present at 2 to 4-fold, 4 to 8-fold, 8 to 16-fold, 16 to 32-fold, 32 to 64-fold, 64 to 100-fold, 100 to 200-fold, 200 to 400-fold, 400 to 800-fold, 800 to 1,000-fold or to a higher density on said surface-engineered exosome than the unmodified ITGA4 on said native exosome. In particular embodiments, SLC3A2, a fragment or a variant of SLC3A2, or a modification thereof is present at 2 to 4-fold, 4 to 8-fold, 8 to 16-fold, 16 to 32-fold, 32 to 64-fold, 64 to 100-fold, 100 to 200-fold, 200 to 400-fold, 400 to 800-fold, 800 to 1,000-fold or to a higher density on said surface-engineered exosome than the unmodified SLC3A2 on said native exosome. In particular embodiments, ATP transporter, a fragment or a variant of ATP transporter, or a modification thereof is present at 2 to 4-fold, 4 to 8-fold, 8 to 16-fold, 16 to 32-fold, 32 to 64-fold, 64 to 100-fold, 100 to 200-fold, 200 to 400-fold, 400 to 800-fold, 800 to 1,000-fold or to a higher density on said surface-engineered exosome than the unmodified ATP transporter on said native exosome.

In some embodiments, the producer cell is further modified to comprise an additional exogenous sequence. For example, an additional exogenous sequence can be introduced to modulate endogenous gene expression, or produce an exosome including a certain polypeptide as a payload. In some embodiments, the producer cell is modified to comprise two exogenous sequences, one encoding the exosome protein or a variant or a fragment of the exosome protein, and the other encoding a payload. In some embodiments, the producer cell can be further modified to comprise an additional exogenous sequence conferring additional functionalities to exosomes, for example, specific targeting capabilities, delivery functions, enzymatic functions, increased or decreased half-life in vivo, etc. In some embodiments, the producer cell is modified to comprise two exogenous sequences, one encoding the exosome protein or a variant or a fragment of the exosome protein, and the other encoding a protein conferring the additional functionalities to exosomes.

In some embodiments, the producer cell is modified to comprise two exogenous sequences, each of the two exogenous sequences encoding a fusion protein on the exosome surface. In some embodiments, a surface-engineered exosome from the producer cell has a higher density of an exosome protein compared to native exosomes isolated from an unmodified cell of the same or similar cell type. In some embodiments, surface-engineered exosome contain an exosome protein at a density 2-, 4-, 8-, 16-, 32-, 64-, 100-, 200-, 400-, 800-, 1,000-fold or higher than a native exosome isolated from an unmodified cell of the same or similar cell type. In some embodiments, the producer cell is further modified to comprise one, two, three, four, five, six, seven, eight, nine, or ten or more additional exogenous sequences.

More specifically, surface-engineered exosomes can be produced from a cell transformed with a sequence encoding one or more exosome surface proteins or a variant thereof including, but not limited to, (1) prostaglandin F2 receptor negative regulator (PTGFRN), (2) basigin (BSG), (3) immunoglobulin superfamily member 3 (IGSF3), (4) immunoglobulin superfamily member 8 (IGSF8), (5) integrin beta-1 (ITGB1), (6) integrin alpha-4 (ITGA4), (7) 4F2 cell-surface antigen heavy chain (SLC3A2), (8) a class of ATP transporter proteins (ATP1A1, ATP1A2, ATP1A3, ATP1A4, ATP1B3, ATP2B1, ATP2B2, ATP2B3, ATP2B4), and (9) immunoglobulin superfamily member 2 (IGSF2). Any of the one or more exosome surface proteins described herein can be expressed in the producer cell from a plasmid, an exogenous sequence inserted into the genome or other exogenous nucleic acid such as a synthetic messenger RNA (mRNA).

In some embodiments, the one or more exosome surface protein is expressed in a cell transformed with an exogenous sequence encoding its full length, endogenous form. In some embodiments, such an exogenous sequence encodes PTGFRN protein of SEQ ID NO: 1. In some embodiments, such an exogenous sequence encodes BSG protein of SEQ ID NO: 9. In some embodiments, such an exogenous sequence encodes IGSF8 protein of SEQ ID NO: 14. In some embodiments, such an exogenous sequence encodes IGSF3 protein of SEQ ID NO: 20. In some embodiments, such an exogenous sequence encodes ITGB1 protein of SEQ ID NO: 21. In some embodiments, such an exogenous sequence encodes ITGA4 protein of SEQ ID NO: 22. In some embodiments, such an exogenous sequence encodes SLC3A2 protein of SEQ ID NO: 23. In some embodiments, such an exogenous sequence encodes ATP1A1 protein of SEQ ID NO: 24. In some embodiments, such an exogenous sequence encodes ATP1A2 protein of SEQ ID NO: 25. In some embodiments, such an exogenous sequence encodes ATP1A3 protein of SEQ ID NO: 26. In some embodiments, such an exogenous sequence encodes ATP1A4 protein of SEQ ID NO: 27. In some embodiments, such an exogenous sequence encodes ATP1B3 protein of SEQ ID NO: 28. In some embodiments, such an exogenous sequence encodes ATP2B1 protein of SEQ ID NO: 29. In some embodiments, such an exogenous sequence encodes ATP2B2 protein of SEQ ID NO: 30. In some embodiments, such an exogenous sequence encodes ATP2B3 protein of SEQ ID NO: 31. In some embodiments, such an exogenous sequence encodes ATP2B4 protein of SEQ ID NO: 32. In some embodiments, such an exogenous sequence encodes IGSF2 protein of SEQ ID NO: 34

Surface-engineered exosomes can be produced from a cell transformed with a sequence encoding a fragment of one or more exosome surface proteins including, but not limited to, (1) prostaglandin F2 receptor negative regulator (PTGFRN), (2) basigin (BSG), (3) immunoglobulin superfamily member 3 (IGSF3), (4) immunoglobulin superfamily member 8 (IGSF8), (5) integrin beta-1 (ITGB1), (6) integrin alpha-4 (ITGA4), (7) 4F2 cell-surface antigen heavy chain (SLC3A2), (8) a class of ATP transporter proteins (ATP1A1, ATP1A2, ATP1A3, ATP1A4, ATP1B3, ATP2B1, ATP2B2, ATP2B3, ATP2B4), and (9) immunoglobulin superfamily member 2 (IGSF2). In some embodiments, the sequence encodes a fragment of the exosome surface protein lacking at least 5, 10, 50, 100, 200, 300, 400, 500, 600, 700, or 800 amino acids from the N-terminus of the native protein. In some embodiments, the sequence encodes a fragment of the exosome surface protein lacking at least 5, 10, 50, 100, 200, 300, 400, 500, 600, 700, or 800 amino acids from the C-terminus of the native protein. In some embodiments, the sequence encodes a fragment of the exosome surface protein lacking at least 5, 10, 50, 100, 200, 300, 400, 500, 600, 700, or 800 amino acids from both the N-terminus and C-terminus of the native protein. In some embodiments, the sequence encodes a fragment of the exosome surface protein lacking one or more functional or structural domains of the native protein.

In some embodiments, the fragment of the exosome surface protein is fused to one or more heterologous proteins. In some embodiments, the one or more heterologous proteins are fused to the N-terminus of the fragment. In some embodiments, the one or more heterologous proteins are fused to the C-terminus of the fragment. In some embodiments, the one or more heterologous proteins are fused to the N-terminus and the C-terminus of the fragment. In some embodiments, the one or more heterologous proteins are mammalian proteins. In some embodiments, the one or more heterologous proteins are human proteins.

Surface engineered exosomes can be produced from a cell transformed with a sequence encoding fragments of PTGFRN. In some embodiments, the fragments of PTGFRN lack one or more functional or structural domains, such as IgV. For example, the fragment of PTGFRN can comprise a polypeptide of SEQ ID NO: 2-7, or 33. In some embodiments, the fragments of PTGFRN are fused to one or more heterologous proteins. The one or more heterologous proteins can be fused to the N-terminus of said PTGFRN fragments. The one or more heterologous proteins can be fused to the C-terminus of said PTGFRN fragments. In some embodiments, the one or more heterologous proteins are fused to both the N-terminus and the C-terminus of said PTGFRN fragments. In some embodiments, the heterologous protein is a mammalian protein. In some embodiments, the heterologous protein is a human protein. In some embodiments, said heterologous protein fused to said PTGFRN fragment additionally contains a signal sequence peptide. The signal sequence peptide can be a polypeptide of SEQ ID NO: 8.

Surface engineered exosomes can be produced from a cell transformed with a sequence encoding fragments of Basigin. In some embodiments, the fragments of Basigin lack one or more functional or structural domains, such as IgV. For example, the fragments of Basigin can comprise a polypeptide of SEQ ID NO: 10-12. In some embodiments, the fragments of Basigin are fused to one or more heterologous proteins. In some embodiments, the one or more heterologous proteins are fused to the N-terminus of said Basigin fragments. In some embodiments, the one or more heterologous proteins are fused to the C-terminus of said Basigin fragments. In some embodiments, the one or more heterologous proteins are fused to both the N-terminus and the C-terminus of said Basigin fragments. In some embodiments, the heterologous protein is a mammalian protein. In some embodiments, the heterologous protein is a human protein. In some embodiments, said heterologous protein fused to said Basigin fragment additionally contains a signal sequence peptide. The signal sequence peptide can be a polypeptide of SEQ ID NO: 13.

Surface engineered exosomes can be produced from a cell transformed with a sequence encoding fragments of IGSF8. In some embodiments, the fragments of IGSF8 lack one or more functional or structural domains, such as IgV. For example, the fragments of IGSF8 can comprise a polypeptide of SEQ ID NO: 15-18. In some embodiments, the fragments of IGSF8 are fused to one or more heterologous proteins. In some embodiments, the one or more heterologous proteins are fused to the N-terminus of said IGSF8 fragments. In some embodiments, the one or more heterologous proteins are fused to the C-terminus of said IGSF8 fragments. In some embodiments, the one or more heterologous proteins are fused to both the N-terminus and the C-terminus of said IGSF8 fragments. In some embodiments, the heterologous protein is a mammalian protein. In some embodiments, the heterologous protein is a human protein. In some embodiments, said heterologous protein fused to said IGSF8 fragment additionally contains a signal sequence peptide. The signal sequence peptide can be a polypeptide of SEQ ID NO: 19.

Surface engineered exosomes can be produced from a cell transformed with a sequence encoding fragments of IGSF2. In some embodiments, the fragments of IGSF2 lack one or more functional or structural domains, such as IgV. In some embodiments, the fragments of IGSF2 are fused to one or more heterologous proteins. In some embodiments, the one or more heterologous proteins are fused to the N-terminus of said IGSF2 fragments. In some embodiments, the one or more heterologous proteins are fused to the C-terminus of said IGSF2 fragments. In some embodiments, the one or more heterologous proteins are fused to both the N-terminus and the C-terminus of said IGSF2 fragments. In some embodiments, the heterologous protein is a mammalian protein. In some embodiments, the heterologous protein is a human protein. In some embodiments, said heterologous protein fused to said IGSF2 fragment additionally contains a signal sequence peptide. The signal sequence peptide can be a polypeptide of SEQ ID NO: 35.

In some embodiments surface-engineered exosomes comprise a polypeptide of a sequence identical or similar to a full-length or a fragment of a native exosome surface protein including, but not limited to, (1) prostaglandin F2 receptor negative regulator (PTGFRN), (2) basigin (BSG), (3) immunoglobulin superfamily member 3 (IGSF3), (4) immunoglobulin superfamily member 8 (IGSF8), (5) integrin beta-1 (ITGB1), (6) integrin alpha-4 (ITGA4), (7) 4F2 cell-surface antigen heavy chain (SLC3A2), (8) a class of ATP transporter proteins (ATP1A1, ATP1A2, ATP1A3, ATP1A4, ATP1B3, ATP2B1, ATP2B2, ATP2B3, ATP2B4), and (9) immunoglobulin superfamily member 2 (IGSF2). In some embodiments, said peptide is 50% identical to a full-length or a fragment of a native exosome surface protein, e.g., 50% identical to SEQ ID NO: 1-34. In some embodiments, said polypeptide is 60% identical to a full-length or a fragment of a native exosome surface protein, e.g., 60% identical to SEQ ID NO: 1-34. In some embodiments, said polypeptide is 70% identical to a full-length or a fragment of a native exosome surface protein, e.g., 70% identical to SEQ ID NO: 1-34. In some embodiments, said polypeptide is 80% identical to a full-length or a fragment of a native exosome surface protein, e.g., 80% identical to SEQ ID NO: 1-34. In some embodiments, said polypeptide is 90% identical to a full-length or a fragment of a native exosome surface protein, e.g., 90% identical to SEQ ID NO: 1-34. In some embodiments, said polypeptide is 95% identical to a full-length or a fragment of a native exosome surface protein, e.g., 95% identical to SEQ ID NO: 1-34. In some embodiments, said polypeptide is 99% identical to a full-length or a fragment of a native exosome surface protein, e.g., 99% identical to SEQ ID NO: 1-34. In some embodiments, said polypeptide is 99.9% identical to a full-length or a fragment of a native exosome surface protein, e.g., 99.9% identical to SEQ ID NO: 1-34.

6.6. Affinity Purification

Some embodiments of the present invention relate to isolation, purification and sub-fractionation of exosomes using a specific binding interaction between a protein enriched on the exosome membrane and an immobilized binding agent. These methods generally comprise the steps of (1) applying or loading a sample comprising exosomes, (2) optionally washing away unbound sample components using appropriate buffers that maintain the binding interaction between the target proteins of exosomes and binding agents, and (3) eluting (dissociating and recovering) the exosomes from the immobilized binding agents by altering the buffer conditions so that the binding interaction no longer occurs.

Some embodiments relate to a method of removing exosomes from a sample using a specific binding interaction between a protein enriched on the exosome membrane and an immobilized binding agent. In the cases, exosomes bound to the binding agent are not eluted from the binding agent and a fraction which does not bind to the binding agent can be collected. The method can be used to purify a sample comprising exosomes and a non-exosomal material such as viruses (e.g., lentivirus, retrovirus, adeno-associated virus, or any other enveloped or non-enveloped virus) or a recombinant protein (e.g., antibodies, enzymes or other polypeptides), wherein the exosomes are contaminating particles. The bound exosomes can be retained bound to the binding agent and the non-exosomal material is collected, substantially free of exosomes.

The target protein, used for this isolation, purification, sub-fractionation or removal process, can be an endogenous protein produced from the genome of a producer cell, a protein introduced to the producer cell by a genetic modification, or a protein modified by chemical, physical or other biological methods. In some cases, the protein is a non-mutant protein or a mutant protein, e.g., a variant or a fragment of an endogenous protein. In some cases, the protein is a fusion protein.

Various binding agents having affinity to the target protein can be used for the embodiments of the present invention. For example, proteins, peptides, and small molecules with specific affinities to the target protein can be used as a binding agent. In some embodiments, binding agents are obtained from organic or inorganic sources. Examples of binding agents from organic sources include serum proteins, lectins or antibodies. Examples of binding agents from inorganic sources include boronic acids, metal chelates, and triazine dyes.

The binding agents can be chemically immobilized or coupled to a solid support so that exosomes having specific affinity to the binding agent become bound. Various forms of solid support can be used, e.g., a porous agarose bead, a microtiter plate, a magnetic bead, or a membrane. In some embodiments, the solid support forms a chromatography column and can be used for affinity chromatography of exosomes.

In some cases, isolation, purification, sub-fractionation and removal of exosomes are done by column chromatography using a column where the binding agents and the solid support are packed. In some embodiments, a sample containing exosomes run through the column to allow setting, a wash buffer run through the column, and the elution buffer subsequently applied to the column and collected. These steps can be done at ambient pressure or with application of additional pressure.

In some cases, isolation, purification, sub-fractionation and removal of exosomes are done using a batch treatment. For example, a sample is added to the binding agent attached to a solid support in a vessel, mixing, separating the solid support, removing the liquid phase, washing, centrifuging, adding the elution buffer, re-centrifuging and removing the elute.

In some cases, a hybrid method can be employed. For example, a sample is added to the binding agent attached to a solid support in a vessel, the solid support bound to the exosomes is subsequently packed onto a column, and washing and elution are done on the column.

In some cases, isolation, purification, sub-fractionation and removal of exosomes are done using a binding agent attached to microtiter plates, magnetic beads, or membranes. In the cases, a sample is added to the binding agent attached to a solid support, followed by the steps of mixing, separating the solid support, removing the liquid phase, washing, removing the washing buffer, adding the elution buffer, and removing the elute.

The binding between the binding agent and a target protein on the exosome is done in various physiological conditions optimal for specific interactions between the binding agent and the target protein on the exosome. Elution of the bound exosomes can be achieved by changing salt concentrations, pH, pI, charge and ionic strength directly or through a gradient.

In some embodiments, a sample isolated, purified or sub-fractionated with one binding agent is subsequently processed with a different binding agent.

In some embodiments, more than one columns are used in series, where each of the multiple columns contains a different binding agent specific to a different target protein.

In some embodiments, a single column contains multiple binding agents, each specific to a different target protein.

In some cases, the binding agent and solid support are reused by introduction of a periodic sanitization step. For example, they can be sanitized with a combination of propylene glycol, isopropanol, high ionic strength, and/or sodium hydroxide.

6.6.1. Sample Preparation

The methods described herein can be used to purify, isolate, sub-fractionate or remove exosomes from various samples comprising exosomes. In some embodiments, the sample is a clarified harvest material containing exosomes. In some cases, the sample comprises exosomes partially purified by a purification method well known in the art. For example, ultrafiltration/diafiltration, hydroxyl apatite chromatography, hydrophobic interaction chromatography, deep filtration, or ion exchange bind/elute chromatography can be used to partially purify exosomes before applying to a binding agent for affinity purification.

In some cases, the partially purified material is further processed to have certain physiological conditions (e.g., pH, temperature, salt concentration, salt type, polarity) for desired interaction with the binding agent. A sample can be prepared by dilution or concentration to obtain certain exosome concentrations, or by adding excipients to change structure of exosomes. In some cases, the partially purified material is applied to the binding agent without any manipulation.

6.6.2. Binding

The methods described herein requires specific interaction between a target protein of an exosome and a binding agent. High-throughput screening can be performed to identify buffer conditions ideal for the specific binding—through altering salt concentration, pH, and/or reducing polarity with an organic modifier, ethylene glycol, propylene glycol, or urea. The interaction between a target protein and a binding agent can also change depending on sample conditions (e.g., sample amount loaded per volume of chromatographic resin, concentration of exosomes, concentration of impurities), loading buffers (e.g., pH, salt concentrations, salt types, polarity), and other physical conditions (e.g., temperature). Furthermore, adding excipients that alter the structure of the exosomes can also change their interactions. In addition, residence time can be adjusted based on differential adsorption rates between impurities and exosomes. Thus, various purification conditions described herein can be tested to identify ideal conditions for the step.

Similar approaches can be used to improve purity and yield, and aid in enriching, depleting, or isolating sub-populations of exosomes. These properties, along with maximizing load challenge and applying more stringent elution conditions, could be employed to further enhance the concentration of exosomes.

6.6.2.1. Elution

Elution of exosomes can be achieved through altering salt concentration, pH, and/or polarity with an organic modifier, ethylene glycol, propylene glycol, or urea.

Selective elution of exosomes can be achieved by increasing the concentration of a monovalent cationic halide salt (e.g., sodium chloride, potassium chloride, sodium bromide, lithium chloride, sodium iodide, potassium bromide, lithium bromide, sodium fluoride, potassium fluoride, lithium fluoride, lithium iodide, sodium acetate, potassium acetate, lithium acetate, and potassium iodide), a divalent or trivalent salt (e.g., calcium chloride, magnesium chloride, calcium sulfate, sodium sulfate, magnesium sulfate, chromium trichloride, chromium sulfate, sodium citrate, iron (III) chloride, yttrium (III) chloride, potassium phosphate, potassium sulfate, sodium phosphate, ferrous chloride, calcium citrate, magnesium phosphate, and ferric chloride), or a combination thereof, in the elution buffer, through the use of an increasing gradient (step or linear) of a monovalent cationic halide salt (e.g., sodium chloride, potassium chloride, sodium bromide, lithium chloride, sodium iodide, potassium bromide, lithium bromide, sodium fluoride, potassium fluoride, lithium fluoride, lithium iodide, sodium acetate, potassium acetate, lithium acetate, and potassium iodide), a divalent or trivalent salt (e.g., calcium chloride, magnesium chloride, calcium sulfate, sodium sulfate, magnesium sulfate, chromium trichloride, chromium sulfate, sodium citrate, iron (III) chloride, yttrium (III) chloride, potassium phosphate, potassium sulfate, sodium phosphate, ferrous chloride, calcium citrate, magnesium phosphate, and ferric chloride), or a combination thereof, at a fixed pH.

Substantial exosome purity can be achieved by flowing through impurities during the column loading phase, eluting impurities during selective excipient washes and selectively eluting product during elution while leaving additional impurities bound to the column. Absorbance measured from column eluates can indicate purify of exosomes obtained by the methods.

Elution can be also achieved by modulating the pH range, salts, organic solvents, small molecules, detergents, zwitterions, amino acids, polymers, temperature, and any combination of the above. Similar elution agents can be used to improve purity, improve yield, and isolate sub-populations of exosomes.

Elution can be also done with multiple elution buffers having different properties, such as pH, salts, organic solvents, small molecules, detergents, zwitterions, amino acids, polymers, temperature, and any combination of the above. A plurality of eluted fractions can be collected, wherein exosomes collected in each fraction has different properties. For example, exosomes collected in one fraction has a higher purity, a smaller or larger average size, a preferred composition, etc. than exosomes in other fractions.

Elution buffers with different properties can be applied as a continuous flow, while a plurality of eluted fractions are collected. Eluted fractions can be collected during isocratic elution or gradient elution. Once at least one eluted fraction is collected, a composition of the eluted fraction can be analyzed. For example, the concentration of exosomes, a host cell protein, a contaminant protein, DNA, carbohydrates, or lipids can be measured in each eluted fraction. Other properties of exosomes in each eluted fraction can be also measured. The properties include an average size, an average charge density, and other physiological properties related to bio-distribution, cellular uptake, half-life, pharmacodynamics, potency, dosing, immune response, loading efficiency, stability, or reactivity to other compounds.

6.6.2.2. Washing

Optionally, purity of exosomes can be further improved by washing samples prior to elution. In some embodiments, excipient can be a washing buffer. The excipient can be a solution having specific pH ranges, salts, organic solvents, small molecules, detergents, zwitterions, amino acids, polymers, and any combination of the above.

More specifically, the excipient can comprise arginine, lysine, glycine, histidine, calcium, sodium, lithium, potassium, iodide, magnesium, iron, zinc, manganese, urea, propylene glycol, aluminum, ammonium, guanidinium polyethylene glycol, EDTA, EGTA, a detergent, chloride, sulfate, carboxylic acids, sialic acids, phosphate, acetate, glycine, borate, formate, perchlorate, bromine, nitrate, dithiothreitol, beta mercaptoethanol, or tri-n-butyl phosphate.

The excipient can also comprise a detergent, selected from the group consisting of cetyl trimethylammonium chloride, octoxynol-9, TRITON™ X-100 (i.e., polyethylene glycol p-(1,1,3,3-tetramethylbutyl)-phenyl ether) and TRITON™ CG-110 available from Sigma-Aldrich; sodium dodecyl sulfate; sodium lauryl sulfate; deoxycholic acid; Polysorbate 80 (i.e., Polyoxyethylene (20) sorbitan monooleate); Polysorbate 20 (i.e., Polyoxyethylene (20) sorbitan monolaurate); alcohol ethoxylate; alkyl polyethylene glycol ether; decyl glucoside; octoglucosides; SafeCare;

ECOSURF™ EH9, ECOSURF™ EH6, ECOSURF™ EH3, ECOSURF™ SA7, and ECOSURF™ SA9 available from DOW Chemical; LUTENSOL™ M5, LUTENSOL™ XL, LUTENSOL™ XP and APG™ 325N available from BASF; TOMADOL™ 900 available from AIR PRODUCTS; NAT-SURF™ 265 available from CRODA; SAFECARE™ 1000 available from Bestchem, TERGITOL™ L64 available from DOW; caprylic acid; CHEMBETAINE™ LEC available from Lubrizol; and Mackol DG.

6.6.3. Other Methods for Improving Outcome

The amount of exosomes that can be loaded per volume of chromatographic resin can be improved by modulating the feed material, for example, by increasing the concentration of exosomes, decreasing the concentration of impurities, altering the pH, decreasing the salt concentrations, decreasing the ionic strength, or altering the specific subpopulations of exosomes. Owing to mass transfer constraints and slow adsorption and desorption of exosomes on the resin, the amount of exosomes that can be loaded per volume of chromatographic resin can be increased by slowing the flow rate during column loading, employing longer columns to increase the residence time.

6.7. Applications

6.7.1. Purification of Exosomes

The use of exosomes for medical purposes requires that the exosomes be free or mostly free of impurities including but not limited to macromolecules, such as nucleic acids, contaminant proteins, lipids, carbohydrates, metabolites, small molecules, metals, or a combination thereof. The present invention provides a method of purifying exosomes from contaminating macromolecules. In some embodiments, purified exosomes are substantially free of contaminating macromolecules.

6.7.2. Sub-Fractionation of Exosomes

Embodiments of the present invention further provide methods for sub-fractionating populations of exosomes based on their membrane protein, size, charge density, ligand type (e.g., tetraspanins) and heparin or other sulfated carbohydrate binding sites. The choice of affinity tag, loading and elution buffer compositions and protocols can result in elution of different sub-populations of exosomes.

For example, embodiments of the present invention provide methods of purifying a population of exosomes with a smaller or larger size. The size of exosomes can be determined by methods available in the field. For example, the size can be measured by nanoparticle tracking analysis, multi-angle light scattering, single angle light scattering, size exclusion chromatography, analytical ultracentrifugation, field flow fractionation, laser diffraction, tunable resistive pulse sensing, or dynamic light scattering.

Embodiments of the present invention further relate to methods of sub-fractionating exosomes based on their charge density. The charge density of exosomes can be determined by potentiometric titration, anion exchange, cation exchange, isoelectric focusing, zeta potential, capillary electrophoresis, capillary zone electrophoresis, gel electrophoresis.

Embodiments of the present invention also relate to sub-fractionating exosomes based on other physiological properties, such as bio-distribution, cellular uptake, half-life, pharmacodynamics, potency, dosing, immune response, loading efficiency, stability, or reactivity to other compounds. The method enables isolation of a population of exosomes that are appropriate for a specific application.

6.8. Characterization of Exosomes

In some embodiments, the methods described herein further comprise the step of characterizing exosomes contained in each collected fraction. In some embodiments, contents of the exosomes can be extracted for study and characterization. In some embodiments, exosomes are isolated and characterized by metrics including, but not limited to, size, shape, morphology, or molecular compositions such as nucleic acids, proteins, metabolites, and lipids.

6.8.1. Measurement of the Contents of Exosomes

Exosomes can include proteins, peptides, RNA, DNA, and lipids. Total RNA can be extracted using acid-phenol: chloroform extraction. RNA can then be purified using a glass-fiber filter under conditions that recover small-RNA containing total RNA, or that separate small RNA species less than 200 nucleotides in length from longer RNA species such as mRNA. Because the RNA is eluted in a small volume, no alcohol precipitation step may be required for isolation of the RNA.

Exome compositions may be assessed by methods known in the art including, but not limited to, transcriptomics, sequencing, proteomics, mass spectrometry, or HP-LC.

The composition of nucleotides associated with isolated exosomes (including RNAs and DNAs) can be measured using a variety of techniques that are well known to those of skill in the art (e.g., quantitative or semi-quantitative RT-PCR, Northern blot analysis, solution hybridization detection). In a particular embodiment, the level of at least one RNA is measured by reverse transcribing RNA from the exosome composition to provide a set of target oligodeoxynucleotides, hybridizing the target oligodeoxynucleotides to one or more RNA-specific probe oligonucleotides (e.g., a microarray that comprises RNA-specific probe oligonucleotides) to provide a hybridization profile for the exosome composition, and comparing the exosome composition hybridization profile to a hybridization profile generated from a control sample. An alteration in the signal of at least one RNA in the test sample relative to the control sample is indicative of the RNA composition.

Also, a microarray can be prepared from gene-specific oligonucleotide probes generated from known RNA sequences. The array can contain two different oligonucleotide probes for each RNA, one containing the active, mature sequence and the other being specific for the precursor of the RNA (for example miRNA and pre-miRNAs). The array can also contain controls, such as one or more mouse sequences differing from human orthologs by only a few bases, which can serve as controls for hybridization stringency conditions. tRNAs and other RNAs (e.g., rRNAs, mRNAs) from both species can also be printed on the microchip, providing an internal, relatively stable, positive control for specific hybridization. One or more appropriate controls for non-specific hybridization can also be included on the microchip. For this purpose, sequences are selected based upon the absence of any homology with any known RNAs.

The microarray can be fabricated using techniques known in the art. For example, probe oligonucleotides of an appropriate length, e.g., 40 nucleotides, are 5'-amine modified at position C6 and printed on activated slides using commercially available microarray systems, e.g., the GeneMachine OmniGrid™ 100 Microarrayer and Amersham CodeLink™ Labeled cDNA oligomer corresponding to the target RNAs is prepared by reverse transcribing the target RNA with labeled primer. Following first strand synthesis, the RNA/DNA hybrids are denatured to degrade the RNA templates. The labeled target cDNAs thus prepared are then hybridized to the microarray chip under hybridizing conditions, e.g., 6.times. SSPE/30% formamide at 25° C. for 18 hours, followed by washing in 0.75.times. TNT at 37° C. for 40 minutes. At positions on the array where the immobilized probe DNA recognizes a complementary target cDNA in the sample, hybridization occurs. The labeled target cDNA marks the exact position on the array where binding occurs, allowing automatic detection and quantification. The output consists of a list of hybridization events, indicating the relative abundance of specific cDNA sequences, and therefore the relative abundance of the corresponding complementary RNAs, in the exosome preparation. According to one embodiment, the labeled cDNA oligomer is a biotin-labeled cDNA, prepared from a biotin-labeled primer. The microarray is then processed by direct detection of the biotin containing transcripts using, e.g., Streptavidin-Alexa647 conjugate, and scanned utilizing conventional scanning methods. Image intensities of each spot on the array are proportional to the abundance of the corresponding RNA in the exosome.

Data mining work is completed by bioinformatics, including scanning chips, signal acquisition, image processing, normalization, statistic treatment and data comparison as well as pathway analysis. As such, microarray can profile hundreds and thousands of polynucleotides simultaneously with high throughput performance. Microarray profiling analysis of mRNA expression has successfully provided valuable data for gene expression studies in basic research. And the technique has been further put into practice in the pharmaceutical industry and in clinical diagnosis. With increasing amounts of miRNA data becoming available, and with accumulating evidence of the importance of miRNA in gene regulation, microarray becomes a useful technique for high through-put miRNA studies. The analysis of miRNA levels utilizing polynucleotide probes can be carried out in a variety of physical formats as well. For example, the use of microtiter plates or automation can be used to facilitate the processing of large numbers of test samples.

6.8.2. Measurement of the Size of Exosomes

In some embodiments, the methods described herein comprise measuring the size of exosomes and/or populations of exosomes included in the purified fractions. In some embodiments, exosome size is measured as the longest measurable dimension. Generally, the longest general dimension of an exosome is also referred to as its diameter.

Exosome size can be measured using various methods known in the art, for example, nanoparticle tracking analysis, multi-angle light scattering, single angle light scattering, size exclusion chromatography, analytical ultracentrifugation, field flow fractionation, laser diffraction, tunable resistive pulse sensing, or dynamic light scattering.

Exosome size can be measured using dynamic light scattering (DLS) and/or multiangle light scattering (MALS). Methods of using DLS and/or MALS to measure the size of exosomes are known to those of skill in the art, and include the nanoparticle tracking assay (NTA, e.g., using a Malvern Nanosight NS300 nanoparticle tracking device). In a specific embodiment, the exosome size is determined using a Malvern NanoSight NS300. In some embodiments, the exosomes described herein have a longest dimension of about 20-1000 nm as measured by NTA (e.g., using a Malvern NanosightNS300). In other embodiments, the exosomes described herein have a longest dimension of about 40-1000 nm as measured by NTA (e.g., using a Malvern NanosightNS300). In other embodiments, the exosome populations described herein comprise a population, wherein 90% of said exosomes have a longest dimension of about 20-1000 nm as measured by NTA (e.g., using a Malvern Nanosight NS300). In other embodiments, the exosome populations described herein comprise a population, wherein 95% of said exosomes have a longest dimension of about 20-1000 nm as measured by NTA (e.g., using a Malvern Nanosight NS300). In other embodiments, the exosome populations described herein comprise a population, wherein 99% of said exosomes have a longest dimension of about 20-1000 nm as measured by NTA (e.g., using a Malvern Nanosight NS300). In other embodiments, the exosome populations described herein comprise a population, wherein 90% of said exosomes have a longest dimension of about 40-1000 nm as measured by NTA (e.g., using a Malvern Nanosight NS300). In other embodiments, the exosome populations described herein comprise a population, wherein 95% of said exosomes have a longest dimension of about 40-1000 nm as measured by NTA (e.g., using a Malvern Nanosight NS300). In other embodiments, the exosome populations described herein comprise a population, wherein 99% of said exosomes have a longest dimension of about 40-1000 nm as measured by NTA (e.g., using a Malvern Nanosight NS300).

Exosome size can be measured using tunable resistive pulse sensing (TRPS). In a specific embodiment, exosome size as measured by TRPS is determined using an iZON qNANO Gold. In some embodiments, the exosomes described herein have a longest dimension of about 20-1000 nm as measured by TRPS (e.g., using an iZON qNano Gold). In other embodiments, the exosomes described herein have a longest dimension of about 40-1000 nm as measured by TRPS (e.g., an iZON qNano Gold). In other embodiments, the exosome populations described herein comprise a population, wherein 90% of said exosomes have a longest dimension of about 20-1000 nm as measured by TRPS (e.g., using an iZON qNano Gold). In other embodiments, the exosome populations described herein comprise a population, wherein 95% of said exosomes have a longest dimension of about 20-1000 nm as measured by TRPS (e.g., using an iZON qNano Gold). In other embodiments, the exosome populations described herein comprise a population, wherein 99% of said exosomes have a longest dimension of about 20-1000 nm as measured by TRPS (e.g., using an iZON qNano Gold). In other embodiments, the exosome populations described herein comprise a population, wherein 90% of said exosomes have a longest dimension of about 40-1000 nm as measured by TRPS (e.g., using an iZON qNano Gold). In other embodiments, the exosome populations described herein comprise a population, wherein 95% of said exosomes have a longest dimension of about 40-1000 nm as measured by TRPS (e.g., using an iZON qNano Gold). In other embodiments, the exosome populations described herein comprise a population, wherein 99% of said exosomes have a longest dimension of about 40-1000 nm as measured by TRPS (e.g., using an iZON qNano Gold).

Exosome size can be measured using electron microscopy. In some embodiments, the method of electron microscopy used to measure exosome size is transmission electron microscopy. In a specific embodiment, the transmission electron microscope used to measure exosome size is a Tecnai™ G2 Spirit BioTWIN. Methods of measuring exosome size using an electron microscope are well-known to those of skill in the art, and any such method can be appropriate for measuring exosome size. In some embodiments, the exosomes described herein have a longest dimension of about nm as measured by a scanning electron microscope (e.g., a Tecnai™ G2 Spirit BioTWIN scanning electron microscope). In other embodiments, the exosomes described herein have a longest dimension of about 40-1000 nm as measured by a scanning electron microscope (e.g., a Tecnai™ G2 Spirit BioTWIN scanning electron microscope). In other embodiments, the exosome populations described herein comprise a population, wherein 90% of said exosomes have a longest dimension of about 20-1000 nm as measured by a scanning electron microscope (e.g., a Tecnai™ G2 Spirit BioTWIN scanning electron microscope). In other embodiments, the exosome populations described herein comprise a population, wherein 95% of said exosomes have a longest dimension of about 20-1000 nm as measured by a scanning electron microscope (e.g., a Tecnai™ G2 Spirit BioTWIN scanning electron microscope). In other embodiments, the exosome populations described herein comprise a population, wherein 99% of said exosomes have a longest dimension of about 20-1000 nm as measured by a scanning electron microscope (e.g., a Tecnai™ G2 Spirit BioTWIN scanning electron microscope). In other embodiments, the exosome populations described herein comprise a population wherein 90% of said exosomes have a longest dimension of about 40-1000 nm as measured by a scanning electron microscope (e.g., a Tecnai™ G2 Spirit BioTWIN scanning electron microscope). In other embodiments, the exosome populations described herein comprise a population wherein 95% of said exosomes have a longest dimension of about 40-1000 nm as measured by a scanning electron microscope (e.g., a Tecnai™ G2 Spirit BioTWIN scanning electron microscope). In other embodiments, the exosome populations described herein comprise a population wherein 99% of said exosomes have a longest dimension of about 40-1000 nm as measured by a scanning electron microscope (e.g., a Tecnai™ G2 Spirit BioTWIN scanning electron microscope).

6.8.3. Measurement of the Charge Density of Exosomes

In some embodiments, the methods described herein comprise measuring the charge density of exosomes and/or populations of exosomes included in the purified fractions. In some embodiments, the charge density is measured by potentiometric titration, anion exchange, cation exchange, isoelectric focusing, zeta potential, capillary electrophoresis, capillary zone electrophoresis, or gel electrophoresis.

6.8.4. Measurement of Density of Exosome Proteins

In some embodiments, the methods described herein comprise measuring the density of exosome proteins on the exosome surface. The surface density can be calculated or presented as the mass per unit area, the number of proteins per area, number of molecules or intensity of molecule signal per exosome, molar amount of the protein, etc. The surface density can be experimentally measured by methods known in the art, for example, by using bio-layer interferometry (BLI), FACS, Western blotting, fluorescence (e.g., GFP-fusion protein) detection, nano-flow cytometry, ELISA, alphaLISA, and/or densitometry by measuring bands on a protein gel.

6.9. Examples

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations can be used, e.g., bp, base pair(s); kb, kilobase(s); pl, picoliter(s); s or sec, second(s); min, minute(s); h or hr, hour(s); aa, amino acid(s); nt, nucleotide(s); and the like.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, Proteins: Structures and Molecular Properties (W.H. Freeman and Company, 1993); A L. Lehninger, Biochemistry (Worth Publishers, Inc., current addition); Sambrook, et al., Molecular Cloning: A Laboratory Manual (2nd Edition, 1989); Methods In Enzymology (S. Colowick and N. Kaplan eds., Academic Press, Inc.); Remington's Pharmaceutical Sciences, 21th Edition (Easton, Pennsylvania: Mack Publishing Company, 2005); Carey and Sundberg Advanced Organic Chemistry 3rd Ed. (Plenum Press) Vols A and B (1992).

6.9.1. Example 1: Identification of Exosome Proteins 6.9.1.1. Collection of Exosomes Exosomes were collected from the supernatant of high density suspension cultures of HEK293 SF cells after 9 days. The supernatant was filtered and fractionated by anion exchange chromatography and eluted in a step gradient of sodium chloride. The peak fraction with the highest protein concentration contained exosomes and contaminating cellular components. The peak fraction was isolated and further fractionated on an Optiprep™ (60% iodixanol w/v) density gradient by ultracentrifugation.

The exosome fraction was concentrated by ultracentrifugation in a 38.5 mL Ultra-Clear (344058) tube for a SW 32 Ti rotor at 133,900×g for 3 hours at 4° C. The pelleted material was resuspended in 1 mL PBS and 3 mL of Optiprep™, bringing the final iodixanol concentration to 45%. For the Optiprep™ gradient, a 4-tier sterile gradient was prepared with 4 mL of 45% iodixanol containing the resuspended material, 3 mL 30% iodixanol, 2 mL 22.5% iodixanol, 2 mL 17.5% iodixanol, and 1 mL PBS in a 12 mL Ultra-Clear (344059) tube for a SW 41 Ti rotor. The Optiprep™ gradient was ultracentrifuged at 150,000×g for 16 hours at 4° C. to separate the exosome fraction. Ultracentrifugation resulted in a Top Fraction known to contain exosomes, a Middle Fraction containing cell debris of moderate density, and a Bottom Fraction containing high density aggregates and cellular debris (FIG. 1). The exosome layer was then gently collected from the top ~3 mL of the tube.

The exosome fraction was diluted in ~32 mL PBS in a 38.5 mL Ultra-Clear (344058) tube and ultracentrifuged at 133,900×g for 3 hours at 4° C. to pellet the purified exosomes. The pelleted exosomes were then resuspended in a minimal volume of PBS (~200 μL) and stored at 4° C.

6.9.1.2. Sample Preparation for LC-MS/MS Analysis

To determine proteins specific to exosomes, the Top Fraction and Bottom Fraction of the Optiprep™ gradient were analyzed by liquid chromatography-tandem mass spectrometry. All samples were received in either phosphate-buffered saline (PBS) buffer or PBS and 5% sucrose. Prior to analysis, the total protein concentration of each sample was determined by bicinchoninic acid (BCA) assay, after which each sample was appropriately diluted to 125 µg/mL in PBS buffer. Next, 50.0 µL of each sample was added to a separate 1.5 mL microcentrifuge tube containing an equal volume of exosome lysis buffer (60 mM Tris, 400 mM GdmCl, 100 mM EDTA, 20 mM TCEP, 1.0% Triton X-100) followed by the transfer of 2.0 µL 1.0% Triton X-100 solution. All samples were then incubated at 55° C. for 60 minutes.

Protein precipitation was performed by adding 1250 µL of ethanol at −20° C. To improve efficiency, samples were vigorously vortexed for approximately 10 minutes and then incubated at −20° C. for 60 minutes. After incubation, samples were sonicated in a water bath for 5 minutes. Precipitated material was pelleted by centrifuging for 5 minutes at 15,000 g at 4° C. The supernatant was decanted, and the pelleted material was thoroughly dried using nitrogen gas. Pellets were resuspended in 30.0 µL digestion buffer (30 mM Tris, 1.0 M GdmCl, 100 mM EDTA, 50 mM TCEP, pH 8.5) which also reduced disulfide bonds. Free cysteine residues were alkylated by adding 5.0 µL alkylation solution (375 mM iodoacetamide, 50 mM Tris, pH 8.5) and incubating the resulting solution at room temperature in the dark for at least 30 minutes.

After incubation, each sample was diluted using 30.0 µL 50 mM Tris pH 8.5, and proteolytic digestion was initiated by adding 2.0 µg trypsin. All samples were mixed and then incubated overnight at 37° C. After the incubation, trypsin activity was ceased by adding 5.0 µL 10% formic acid. Prior to analysis by LC-MS/MS, each sample was desalted using Pierce C18 spin columns. At the end of this process, each sample was dried down and reconstituted in 50.0 µL of water with 0.1% formic acid and transferred to an HPLC vial for analysis.

6.9.1.3. LC-MS/MS Analysis

Samples were injected into an UltiMate 3000 RSCLnano (Thermo Fisher Scientific) low flow chromatography system, and tryptic peptides were loaded onto an Acclaim PepMap 100 C18 trapping column (75 µm×2 cm, 3 µm particle size, 100 Å pore size, Thermo Fisher Scientific) using loading mobile phase (MPL: water, 0.1% formic acid) at a flowrate of 1.000 µL/min. Peptides were eluted and separated with a gradient of mobile phase A (MPA: water, 0.1% formic acid) and mobile phase B (MPB: acetonitrile, 0.1% formic acid) at a flowrate of 300 nL/min across an EASY-Spray C18 analytical column (75 µm×25 cm, 2 µm particle size, 100 Å pore size, Thermo Fisher Scientific). The stepwise gradient used for elution began at 2% MPB, where it was held for 8 minutes during loading. The percentage MPB then increased from 2-17% over 35 minutes, again from 17-25% over 45 minutes, and finally from 25-40% over 10 minutes. The most hydrophobic species were removed by increasing to 98% MPB over 5 minutes, then holding there for 10 minutes. The total runtime for the method was 135 minutes and allowed sufficient time for column re-equilibration. Wash cycles were performed in between non-identical analytical injections to minimize carry-over.

Mass analyses were performed with a Q Exactive Basic (Thermo Fisher Scientific) mass spectrometer. Precursor ion mass spectra were measured across an m/z range of 400-1600 Da at a resolution of 70,000. The 10 most intense precursor ions were selected and fragmented in the HCD cell using a collision energy of 27, and MS/MS spectra were measured across an m/z range of 200-2000 Da at a resolution of Ions with charge states from 2-4 were selected for fragmentation and the dynamic exclusion time was set to 30 seconds. An exclusion list containing 14 common polysiloxanes was utilized to minimize misidentification of known contaminants.

6.9.1.4. Data Processing

Proteins were first identified and quantified (label-free) using Proteome Discoverer software (version 2.1.1.21, Thermo Fisher Scientific) and the Sequest HT algorithm combined with the Target Decoy PSM Validator. Searches were performed against the full Swiss-Prot *Homo sapiens* (taxonomy 9606 version 2017 May 10: 42,153 entries) reference database, as well as a custom Uniprot database containing Ela proteins (7 entries). The following search parameters were used: enzyme, trypsin; maximum of 2 missed cleavages; minimum peptide length of 6 residues; 10 ppm precursor mass tolerance; and 0.02 Da fragment mass tolerance. The search also included specific dynamic modifications (oxidation of M; deamidation of N or Q; phosphorylation of S, T, or Y; pyro-glutamation of peptide-terminal E; and acetylation of protein N terminus) and static modifications (carbamidomethylation of C).

In the Target Decoy PSM Validator, the maximum delta Cn and both strict and relaxed target false discovery rates (FDRs) were set to 1 because the data were searched again using Scaffold software (version 4.8.2, Proteome Software Inc.). In Scaffold, the data were also searched using the X! Tandem open source algorithm to identify proteins using a protein threshold of 99.0%, a minimum of 2 peptides, and a peptide threshold of 95%.

To determine the identity of novel exosome-specific proteins, total peptide spectral matches (PSMs) were compared for proteins found in the top exosome fraction of the Optiprep™ gradient versus those in the lower fraction. As shown in FIG. 2, there was weak correlation between the top-fraction proteins (Y-axis) and the bottom-fraction proteins (X-axis). Proteins plotted above the dotted line represent exosome-enriched proteins, while those below the dotted line represent contaminant-enriched proteins. Importantly, there were a number of membrane-associated proteins identified that were highly enriched in the exosomes fraction, including (1) prostaglandin F2 receptor negative regulator (PTGFRN), (2) basigin (BSG), (3) immunoglobulin superfamily member 3 (IGSF3), (4) immunoglobulin superfamily member 8 (IGSF8), (5) integrin beta-1 (ITGB1), (6) integrin alpha-4 (ITGA4), (7) 4F2 cell-surface antigen heavy chain (SLC3A2), and (8) a class of ATP transporter proteins (ATP1A1, ATP1A2, ATP1A3, ATP1A4, ATP1B3, ATP2B1, ATP2B2, ATP2B3, ATP2B4). As shown in the tryptic peptide coverage maps in FIGS. 3-5, the mass spectrometry study resulted in broad coverage of PTGFRN (FIG. 3), IGSF8 (FIG. 4), and Basigin (FIG. 5). Together, these results demonstrate that there are numerous transmembrane proteins enriched in purified exosome populations that may be useful for purifying exosomes from heterogeneous populations or for use as scaffolds in generating engineered exosomes.

6.9.2. Example 2: Verification of Surface Protein Expression

To confirm that the exosome-specific proteins identified in the mass spectrometry studies were highly enriched on the surface of exosomes, protein blotting was carried out on total cell lysate and purified exosome populations from HEK293 cells. As shown in FIG. 6A, the total protein pattern differed substantially between total cell lysate (left)

and exosome lysate (right). Specifically, there was a strong band at ~110 kDa in the exosome lysate that was absent in the total cell lysate. Western blotting for PTGFRN revealed a band at the expected size of ~110 kDa in the exosome lysate but not in the cell lysate (FIG. 6B), indicating that PTGFRN is highly enriched in exosomes, and may be visually detectable in total exosome lysate.

The mass spectrometry studies indicated the presence of several novel exosome-associated membrane proteins. To further confirm this association, exosome fractions were purified on self-forming Optiprep™ gradients and analyzed by Western blotting. As shown in FIG. 7A, total protein is detected in all fractions of the gradient and the exosome marker proteins Alix and Syntenin are enriched in fractions 2-6. Importantly, each of the novel surface marker proteins analyzed were enriched in these same fractions, indicating a strong and specific association with exosomes (FIG. 7B). The demonstration that these transmembrane proteins are highly expressed and enriched on exosomes provides an opportunity for purifying exosomes by using a binding agent directed against any of these proteins, as well as generating high expression surface-modified exosomes containing heterologous proteins fused to any of these novel proteins (FIG. 8).

6.9.3. Example 3: Domain Characterization of PTGFRN

PTGFRN, BSG, IGSF3, and IGSF8 are all type I single-pass transmembrane proteins with an N-terminus facing the extracellular/extravesicular environment and a C-terminus located in the cytoplasm/exosome lumen and contain at least two immunoglobulin V (IgV) repeats, as illustrated in FIG. 8. PTGFRN was the most highly enriched surface protein detected in the mass spectrometry analysis shown in FIG. 2. Expression constructs encoding fusion proteins between GFP and full length PTGFRN or various IgV truncation mutants of PTGFRN described in FIGS. 9A and B were stably expressed in HEK293 cells. Exosomes were isolated from the HEK293 cell culture using the method described in Example 1 and analyzed by Western blotting using an anti-GFP antibody. As shown in FIG. 9B, expression of the fusion proteins between GFP and full-length or truncated PTGFRN were detected in the purified exosomes. Interestingly, deletion of the first IgV domain resulted in a lower molecular weight band (marked as "cleaved product") that was not detectable with overexpression of the full-length protein. This smaller product was consistently detected in all truncation mutants, suggesting that it was generated as a result of protease cleavage. The exosomes containing various GFP-PTGFRN fusion proteins were analyzed on an SDS-PAGE mini-PROTEAN® TGX Stain-Free Gel (Bio-Rad, Inc.) to measure total exosome protein. The result is provided in FIG. 10. Expression of the fusion protein of GFP and full-length PTGFRN was easily detectable and very abundant, at a level as high as ~50% of the total proteins in the purified exosomes (lane 2). The lower molecular weight cleavage product (marked as "cleaved product") was not clearly visible and thus was absent in the native exosomes or exosomes over-expressing full length PTGFRN (lanes 1 and 2), suggesting that the first IgV domain (IgV 1) at the N-terminus of the protein may prevent the cleavage of PTGFRN.

Full-length PTGFRN and various truncated PTGFRN mutants were then stably expressed with an N-terminal FLAG tag in HEK293 cells (FIG. 11A). Exosomes from the cell culture were collected and analyzed by Western blotting with an anti-FLAG antibody. The result is provided in FIG. 11B. In contrast to the fusion proteins containing GFP in their C-terminus (FIGS. 9 and 10), fusion proteins containing a FLAG tag in the N-terminus did not yield a low molecular weight band (marked as "no cleavage product" in FIG. 11B), and the shorter truncations were detected at a low level. This result suggests that the cleavage event is likely removing the N-terminus of the protein linked to the FLAG epitope used for Western blotting (FIG. 11B).

PTGFRN is poorly detected in cell lysate and a mixture of intact and cleaved PTGFRN is detected in purified exosomes as suggested by the Western blot result provided in FIGS. 6A and B. This suggests that PTGFRN is being cleaved while being localized and integrated in the exosome membrane or during formation of exosomes. ADAM10 (A Disintegrin And Metalloproteinase Domain 10) is a conventional exosome protein and a membrane-associated metalloprotease. HEK293 cells were transfected with Cas9 and four guide RNAs targeting the ADAM10 locus (CRISPR32174_SG, CRISPR726928_SG, CRISPR726931_SG, and CRISPR726933_SG, Thermo Fisher Scientific) to generate ADAM10 knockout cells. ADAM10 knockout cells (ADAM 10-) or wild type cells (ADAM10+) were then stably transfected with either a construct encoding a fusion protein containing full-length PTGFRN fused to GFP or a different fusion protein containing truncated PTGFRN lacking the first three IgV domains fused to GFP (PTGFRN_IgV3-GFP). Exosomes were isolated from these cells and expression of the fusion proteins was measured by total protein PAGE and Western blotting using an anti-GFP antibody. FIG. 12A shows that comparable amounts of total proteins were loaded on each lane. Western blotting using an anti-ADAM10 antibody (ab124695; Abcam) showed efficient deletion of ADAM 10 in the knockout cells (FIG. 12B). Western blotting using an anti-GFP antibody showed high level expression of fusion proteins containing full length PTGFRN and GFP in both wild type (ADAM10+) and ADAM10 knockout cells (ADAM10-) as provided in FIG. 12C (lanes 1 and 2). This result is consistent with the result in FIG. 9B where no cleavage of fusion proteins containing the full length PTGFRN was detected. Interestingly, the cleavage product previously detected for PTGFRN_IgV3-GFP was detected in the wild type cells but was absent in the ADAM10 knockout cells (FIG. 12C, lanes 3 and 4). This suggests that ADAM10 mediates the cleavage of exosomal PTGFRN fragments. This result also suggests that a fusion protein containing truncated PTGFRN fragments would be more successfully expressed on exosomes from cells that lack ADAM10 (ADAM10-).

PTGFRN can be used as an attractive fusion partner for high-density exosome decoration/loading, but because of its size (~100 kDa) a smaller truncated version would be preferred to allow co-expression of large, biologically active molecules. The ADAM10-dependent cleavage detected in each of the IgV truncation mutants presents an issue for high-density loading because a certain percentage of any fusion protein would be cleaved from the exosome surface, reducing the degree of loading/display. To identify a minimal PTGFRN fragment that facilitates high density exosome surface display without suffering from protease cleavage, PTGFRN lacking five of the six IgV domains (PTGFRN_IgV6) was expressed as a fusion to a FLAG tag and a fusion partner protein (FIG. 13). Expression of fusion proteins containing PTGFRN_IgV6 yielded the predicted cleavage product identified previously (FIG. 14B, #451). Serial truncation mutants of PTGFRN_IgV6 lacking four additional amino acids at a time were also tested, and removal of 12 amino acids yielded exosomes that did not undergo cleavage of PTGFRN (FIG. 14A, FIG. 14B, #454). The PTGFRN #454 is a polypeptide of SEQ ID NO: 33. Additionally, because the FLAG tag is N-terminal to the cleavage site, shorter truncations of PTGFRN_IgV6 resulted in higher expression of the fusion protein, suggesting that cleavage is not occurring with these truncations (FIG. 14C).

The results provided in FIG. 15 further suggest that full-length PTGFRN (FL) and PTGFRN_454 (sIgV) would be ideal fusion partners for high-density expression of luminal (C-terminal fusions) or surface (N-terminal) proteins on and/or in exosomes. To test this hypothesis, several scaffold proteins were tested for their ability to produce high-density display exosomes. Fusion proteins comprising a scaffold protein and GFP were expressed in the cell culture, specifically fusion proteins containing GFP fused to the luminal side of the frequently used pDisplay scaffold (PDGF receptor), PalmPalm (palmitoylation sequence), CD81, or either full length PTGFRN (FL) or PTGFRN_454 (sIgV). A dose titration of exosomes purified from the cells stably expressing each fusion protein demonstrated that the PTGFRN fusion proteins resulted in much greater GFP fluorescence than any other scaffold, including the well-known exosome protein CD81. Compared to the pDisplay scaffold, full-length PTGFRN and sIgV resulted in >25-fold enhancement in loading efficiency (FIG. 15). These results suggest that use of the full-length PTGFRN or the truncated PTGFRN (sIgV) which is short enough to remove the cleavage site, as a fusion partner allows for high-density display or exosome loading.

6.9.4. Example 4: IGSF8 Overexpression does not Lead to High Density Exosome Display The expression level of PTGFRN suggests that it would be an ideal fusion partner for producing engineered exosomes. To determine if other members of the immunoglobulin-containing protein family would be suitable for exosome engineering, HEK293 cells were stably transfected with an IGFS8-GFP fusion protein and the resulting exosomes were purified (FIG. 16A). Native exosomes and IGSF8-GFP exosomes were analyzed on an SDS-PAGE mini-PROTEAN® TGX Stain-Free Gel (Bio-Rad, Inc.), which uses a tryptophan-binding dye to detect proteins, as provided in FIG. 16B. IGSF8 contains 10 tryptophan residues, allowing for its easy detection. Western blotting using an anti-GFP antibody confirmed expression of IGSF8-GFP on the over-expressing exosomes (FIG. 16B, bottom). Interestingly, when the IGSF8-GFP exosomes were tested for GFP fluorescence compared to GFP fusions to the pDisplay scaffold (PDGF receptor), CD81, or either full length PTGFRN (FL) or PTGFRN_454 (sIgV), IGSF8 (FL IGSF8) failed to show GFP enrichment over low-level stochastic display observed with pDisplay (FIG. 17). This result suggests that not every IgV family member can be used as a fusion protein for engineering high-density exosome surface display/luminal loading, and that PTGFRN and other family members are superior to IGSF8 in this respect. IGSF8 expression, however, was detected at high levels on the surface of unmodified exosomes, which would permit IGSF8 to be used as a target for exosome affinity purification.

6.9.5. Example 5: Expression and Characterization of the Extracellular Domain of PTGFRN in Mammalian Cells The extracellular domain (ECD) of PTGFRN is 98 kDa and contains six tandem IgV repeats. The ECD of PTGFRN may be a desirable target for exosome affinity purification reagents due to its size and high expression levels. To characterize this segment of PTGFRN, the PTGFRN ECD was expressed as a fusion protein with the endogenous signal peptide at the N-terminus (SP), and a PAR1 cleavage site and Fc domain at the C-terminus (FIG. 18). PAR1 is a substrate for thrombin and can be used to elute Fc fusion proteins using Protein A resin. PTGFRN has nine predicted N-linked glycosylation sites and 6 predicted disulfide bonds, which preclude the use of bacterial expression systems for the production of endogenous glycoproteins. The PTGFRN ECD was overexpressed using the Expi293 Expression System (Thermo Fisher Scientific), which is used to produce high yield mammalian recombinant proteins. Conditioned cell culture media from transfected Expi293 cells was 0.2 µm filtered and purified on Protein A followed by low pH glycine elution and immediate neutralization. The Fc tag was removed with thrombin treatment and the cleaved protein pool was re-run over Protein A. The flow-through was collected, concentrated, and polished on preparative SEC. The purified PTGFRN ECD was analyzed by gel filtration chromatography in PBS pH 7.4 using a Superdex 200 column (GE Healthcare) and detected at 280 nm UV fluorescence. FIG. 19A shows a single elution peak at ~55 mL and FIG. 19B shows a single protein product at the predicted size of PTGFRN ECD when the eluate peak was analyzed on a denaturing SDS-PAGE mini-PROTEAN® TGX Stain-Free Gel (Bio-Rad, Inc.), indicating PTGFRN ECD can be purified from mammalian cells.

To confirm proper expression of the PTGFRN ECD, the purified protein was analyzed by size exclusion chromatography/multiangle light scattering (SEC-MALS), using BSA and an anti-VLA4 antibody as standards for comparison. Recombinant PTGFRN ECD was eluted at ~2× its predicted molecular weight (198 kDa as opposed to the predicted molecular weight, 98 kDa; FIG. 20A). To determine whether PTGFRN ECD forms a homodimer in solution, recombinant PTGFRN ECD was run over an analytical SEC column (Tosoh, 7.8×30 cm, G3000SW xl) in PBS in the absence of guanidium chloride (GuHCl) or in the presence of 1M or 2M guanidinium chloride (GuHCl). FIG. 20B shows the elution profile of the PTGFRN ECD under increasing GuHCl (no GuHCl (a curve labeled "PTGFRN"), 1M GuHCl (a curve labeled "PTGFRN+1M GuHCl"), or 2M GuHCl (a curve labeled "PTGFRN+2M GuHCl")) and the conversion of the predicted dimeric peak to a monomeric peak. These results suggest that PTGFRN ECD forms a homodimer, and that PTGFRN dimerization may naturally occur on the exosome surface.

6.9.6. Example 6: PTGFRN Protein Array

PTGFRN is poorly characterized in the literature, and its role as an exosomal protein is largely unexplored. PTGFRN is also known as CD9 Partner 1 (CD9P-1) due to its interaction with CD9, which is also found on the surface of exosomes. To further understand which proteins PTGFRN binds to, recombinant mono-biotinylated human PTGFRN ECD was generated and probed on a protein microarray containing over 20,000 proteins encompassing 81% of the human proteome (CDI Laboratories). Binding analysis was performed at pH 5.6 and 7.4 to represent the pH of the acidifying endosome and the cytosol, respectively. Nine positive hits were identified at pH 7.4, and 16 were identified at pH 5.6. Three proteins (LGALS1, galectin-1; FCN1, ficolin-1; MGAT4B, alpha-1,3-mannosyl-glycoprotein 4-beta-N-acetylglucosaminyltransferase B) were identified at both pH 5.6 and pH 7.4 (FIG. 21). LGALS1 is known to bind to monomeric carbohydrates and complex glycans but has not been implicated as a PTGFRN binding partner. To confirm the interaction between PTGFRN and LGALS1, biotinylated recombinant PTGFRN ECD was bound to a Streptavidin optical probe and analyzed by bio-layer interferometry (BLI) using an Octet® RED96 (Pall). Dose-dependent binding of galectin-1 to PTGFRN was confirmed by BLI (FIG. 22). The interaction between LGALS1 and PTGFRN was reversible and competed by lactose in a dose-dependent manner (FIG. 23), demonstrating the specificity of this interaction. These results also suggest that exosomes may be purified by using PTGFRN binding partners as affinity reagents.

6.9.7. Example 7: Binding of Anti-PTGFRN Antibody to PTGFRN or Exosomes

Biotinylated PTGFRN was bound to a Streptavidin probe of an Octet® RED96 (Pall) and incubated in PBS+0.1% Tween 20 with increasing concentrations of a monoclonal rat antibody against CD315, an alias for PTGFRN (MABT883, Millipore Sigma). Dose-dependent binding was detected suggesting specific recognition of PTGFRN by the antibody (FIG. 24). To determine whether the anti-CD315 antibody could bind to exosomes, the anti-CD315 antibody was bound to a Protein L probe and incubated with increasing amounts of Optiprep™ purified HEK293 exosomes (FIG. 25). As shown in FIG. 25, the dose-dependent deflection after incubation with purified exosomes shows that the anti-CD315 antibody can recognize endogenous PTGFRN on the exosome surface. A similar experiment was performed with HEK293 cells stably transfected with full length PTGFRN to generate PTGFRN overexpressing exosomes (PTGFRN++ exosomes). The overexpressing exosomes were incubated with the immobilized anti-CD315 antibody and resulted in a dose-dependent deflection indicating specific binding between the antibody and exosomes (FIG. 26). To compare the extent of antibody binding to native or PTGFRN overexpressing exosomes, 1.1E11 exosomes of each variety were incubated in the presence of the anti-CD315 antibody and measured by BLI. As shown in FIG. 27, the PTGFRN overexpressing exosomes led to a much greater deflection than the native exosomes, indicating that increased levels of PTGFRN leads to greater binding, and that PTGFRN binding can therefore be used for exosome purification.

6.9.8. Example 8: Domain Recognition by Anti-PTGFRN Antibodies

The results in Examples 6 and 7 suggest that exosomes may be purified based on affinity interactions with PTGFRN. Full length PTGFRN and a series of truncation mutants were expressed as mono-biotinylated recombinant proteins using the Expi293 system described above (FIG. 28, left). Each of the truncations was incubated with the anti-CD315 antibody and binding was measured by BLI. Only full length PTGFRN bound the anti-CD315 antibody, indicating that the epitope is at the N-terminus of the protein in the first IgV domain.

Polyclonal antibody pools were generated by injecting rabbits with recombinant full-length ecto-domain of PTGFRN similar to construct 1 in FIG. 28 but lacking a biotinylation sequence. Polyclonal antibody pools were purified from terminal bleeds by Protein A and tested for reactivity against PTGFRN truncation fragments. Each of the fragments was analyzed on a denaturing SDS-PAGE mini-PROTEAN® TGX Stain-Free Gel (Bio-Rad, Inc.) confirming expression of correct length proteins (FIG. 29A). Western blotting was then carried out on the samples using the pooled polyclonal rabbit antibodies, and correct sized bands were detected in each lane as well as for control native exosomes, confirming specific reactivity with polyclonal PTGFRN antibodies (FIG. 29B). To confirm this result, each of the biotinylated PTGFRN fragments was analyzed by BLI and the results are provided in FIG. 30. Incubation with the polyclonal antibody pools showed binding in all conditions, demonstrating broad reactivity with the antibodies for each of the IgV domain of PTGFRN.

6.9.9. Example 9: Exosomes from Diverse Cell Lines Express IgV Family Members and Other Novel Surface Proteins Cell lines of different tissues of origin (HEK293SF, kidney; HT1080, connective tissue; K562, bone marrow; MDA-MB-231, breast; Raji, lymphoblast) were grown to logarithmic phase and transferred to media supplemented with exosome-depleted serum for ~6 days. Bone marrow-derived mesenchymal stem cells (MSC) were grown on 3D microcarriers for five days and supplemented in serum-free media for three day. Supernatant was isolated, and exosomes were purified using the Optiprep™ density-gradient ultracentrifugation method described above. Each of the purified exosomes was analyzed by LC-MS/MS as described above, the number of peptide spectrum matches (PSMs) for several exosome surface proteins was quantified (PTGFRN, IGSF8, IGSF3, BSG, SLC3A2, ITGB1, CD81, and CD9), and the results are provided in FIG. 31. The tetraspanins CD81 and CD9 were detectable in most purified exosome populations, but were, in some cases, equal to or lower than the other surface markers (e.g., compare CD9 to PTGFRN, BSG, and SLC3A2 in all cell lines). This finding indicates that the newly-identified surface markers, including the IgV protein family members are suitable targets for developing exosome affinity purification methods for several unrelated cell lines derived from different tissues.

6.9.10. Example 10: Generation of PTGFRN Knockout Cells and Exosomes

To generate PTGFRN knockout cells, HEK293SF cells were transfected with recombinant Cas9 and guide RNAs targeting exon 2 and the transmembrane region of PTGFRN. The guide RNAs targeting exon2 generated by ThermoFisher included: (1) CGTTGGCAGTCCGCCTTAAC, CRISPR926045_CR (SEQ ID NO: 36); (2) CATAGT-CACTGACGTTGCAG, CRISPR926054_CR (SEQ ID NO: 37); (3) TTGTGGAGCTTGCAAGCACC, CRISPR926055_CR (SEQ ID NO: 38); and (4) GTTCTT-TATGTGGAGCTCCA, CRISPR926071_CR (SEQ ID NO: 39). The guide RNAs targeting the transmembrane region generated by ThermoFisher included (1) TATCCCTTGCT-GATCGGCGT, TMgRNA5.1.97 (SEQ ID NO: 40); (2) GCTGCAGTACCCGATGAGAC, TMgRNA3.7.87 (SEQ ID NO:41).

Targeted gene editing and deletion of the exon 2 and the transmembrane region of PTGFRN was confirmed by PCR and sequencing. Exosomes from five clonal PTGFRN knockout (PTGFRN KO) cell lines were purified as described above and analyzed by PAGE and Western blotting using the polyclonal rabbit antibody pools described in Example 8. As shown in FIG. 32B, bands corresponding to PTGFRN were not detected in any of the five knockout clones, demonstrating targeted deletion of PTGFRN in producer cells and purified exosomes. Importantly, exosome production yield and overall protein banding patterns (FIG. 32A) were not affected by PTGFRN deletion, indicating that PTGFRN KO exosomes can be used for experimental purposes.

To determine whether PTGFRN deletion altered the proteomic profile of purified exosomes, native exosomes and PTGFRN KO exosomes were analyzed by comparative mass spectrometry. As shown in FIG. 33, the protein content of the native and PTGFRN KO exosomes were very similar with the sole exception of PTGFRN, which was undetectable in the PTGFRN KO exosomes. The exosome markers Alix, CD81, TSG101, and CD9 were not significantly different between the groups. These data demonstrate that PTGFRN can be removed from exosomes without altering the proteomic profile of the exosomes.

To verify that PTGFRN deletion resulted in complete functional removal of PTGFRN and to demonstrate that the anti-PTGFRN (anti-CD315) antibody described in Example 7 is specific to PTGFRN, exosome binding experiments using BLI were carried out with native exosomes, PTGFRN overexpressing exosomes (PTGFRN++) and PTGFRN KO exosomes. Similar to the experimental results described in FIG. 27 and Example 7, PTGFRN++ exosomes bound to the immobilized anti-CD315 antibody with a greater affinity than native exosomes (FIG. 34). In contrast, an equal number of PTGFRN KO exosomes failed to bind to the immobilized antibody (FIG. 34), demonstrating that PTGFRN deletion ablates interaction of the PTGFRN KO exosomes with anti-PTGFRN affinity reagents.

6.9.11. Example 11: Exosomes can be Purified with Affinity Reagents Recognizing PTGFRN Custom monoclonal antibodies against PTGFRN were generated from the immunized rabbits as described in Example 8. To determine whether exosomes could be isolated by pulling PTGFRN, $5 \times 10^{10}$ native or PTGFRN KO exosomes were added to either magnetic Protein A beads (catalog #10001D; Invitrogen) or Protein A beads functionalized with 10 μg of a custom anti-PTGFRN monoclonal antibody. Each exosome-bead mixture was incubated for 30 minutes at room temperature and washed three times with PBS+0.1% v/v TWEEN® 20. Washed beads were eluted by incubating in elution buffer (20 mM glycine pH 3.6, 2× Laemmli sample buffer (catalog #1610737, Bio-Rad, Inc.), 10% β-mercaptoethanol) at 95° C. for 10 minutes and the boiled supernatant was analyzed by PAGE and anti-PTGFRN Western blotting using a different custom anti-PTGFRN monoclonal antibody. Total protein analyzed by PAGE showed a band corresponding to the molecular weight of PTGFRN only in the native exosome condition in the presence of the anti-PTGFRN antibody (FIG. 35A). This band was verified as PTGFRN by western blotting (FIG. 35B). HC and LC correspond to the heavy chain and light chain, respectively, of the anti-PTGFRN antibody used for purification. These data demonstrate that PTGFRN-containing exosomes can be purified from a solution by pulling PTGFRN on the exosome surface.

6.9.12. Example 12: Diverse Heterologous Proteins can be Fused to PTGFRN to Facilitate Overexpression on Exosomes Experimental data provided in FIGS. 11, 13, 14 and 15 demonstrates that several proteins can be dramatically overexpressed by using PTGFRN as an overexpression scaffold. The overexpression using PTGFRN was significantly better than expression using other exosome overexpression scaffolds. To determine the breadth of proteins that can be successfully overexpressed by being fused to PTGFRN, several engineered exosomes were generated. Factor VIII (FVIII) is a large enzyme involved in the coagulation cascade. A fragment of FVIII lacking the B Domain (BDDFVIII) was fused to the N-terminus (externally facing side) of PTGFRN and expressed in HEK293SF cells. Purified exosomes were analyzed by PAGE (FIG. 36A) and Western blot (FIG. 36B). A light chain of FVIII generated by processing of a full length FVIII in cell culture was readily detected in the engineered exosomes but not in the native exosomes using antibodies against FVIII (FIG. 36B; catalog #GMA-8025, Green Mountain Antibodies). A full-length FVIII has a molecular weight of 165 kDa, which is significantly larger than the molecular weight of PTGFRN (~120 kDa), demonstrating that very large proteins, including enzymes, can successfully be expressed as PTGFRN fusions on the surface of exosomes.

The PTGFRN fusion partners described above are all proteins with an ordered three-dimensional structure. XTEN® peptides (Amunix; Mountain View, CA) have long, disordered, repeated sequences with a dramatically increased apparent molecular mass compared to their primary sequence. A fusion construct encoding XTEN (a protein comprising randomized 288-amino acids which include 8% Ala, 12% Glu, 18% Gly, 17% Pro, 28% Ser and 17% Thr), a fragment of PTGFRN (SEQ ID NO: 33) and GFP was stably expressed in HEK293SF cells. Purified exosomes were isolated and analyzed by PAGE (FIG. 37A) and Western blotting (FIG. 37B). As shown in FIG. 37B, the C-terminal GFP of the fusion protein was detected by Western blotting, demonstrating in-frame translation of the fusion protein on the purified exosomes. These results demonstrate that unstructured proteins can also be stably expressed as fusions to PTGFRN. Furthermore, these results show that heterologous proteins can be simultaneously fused to the N- and C-termini of PTGFRN and result in intact proteins displayed on the exosome surface and lumen, respectively. Thus, PTGFRN is a robust scaffold that is amenable to protein fusions ranging in size from several amino acids (e.g., a FLAG tag) to over 150 kDa (BDDFVIII) of various structures and classes on either one or both of the N- or the C-termini.

6.9.13. Example 13: PTGFRN Sequences are Better at Expressing Heterologous Proteins on Exosomes than Other Exosomal Overexpression Systems The data in Example 3 and FIG. 15 demonstrate that PTGFRN is superior to other exosome scaffolds at expressing heterologous proteins in a bulk population of exosomes. These results cannot, however, differentiate between increased expression in a subset of exosomes versus a uniformly increased expression across all exosomes in a purified population. For the purposes of developing a uniform exosome therapeutic, it is preferred to have a homogenous exosomes population with uniformly increased expression rather than a heterogeneous exosome population including highly overexpressing exosomes and unmodified exosomes. To address this issue, we characterized individual exosomes in exosome populations on a particle-by-particle basis by nano-flow cytometry using the Flow NanoAnalyzer (NanoFCM, Inc.; Xiamen, China). The Flow NanoAnalyzer can measure light scattering and fluorescence emission of individual nanoparticles as small as 10 nm in diameter. Native exosomes and modified exosomes encoding luminal GFP fusions to CD9, CD81, or PTGFRN were isolated from stably transfected HEK293SF cells and purified by Optiprep® density gradient ultracentrifugation as described above. Analysis by Flow NanoAnalyzer set to excitation 488/emission 509 demonstrated that CD9-GFP exosomes were ~48% positive, CD81-GFP exosomes were ~80% positive, and PTGFRN-GFP exosomes were ~97% positive for GFP expression in the particle-by-particle analysis (FIG. 38, left). Furthermore, the mean fluorescence intensity (MFI) followed a similar trend, with PTGFRN-GFP exosomes being ~2-fold brighter than CD81-GFP exosomes overall (FIG. 38, right). These data demonstrate that exosomes modified to express PTGFRN-GFP fusion protein are a homogenous exosome population highly expressing the fusion protein, and the overall expression level was much higher than native or other modified exosomes expressing GFP fused to other exosome scaffolds.

The N-terminus of PTGFRN consists of a predicted signal peptide sequence (amino acids 1-21; SEQ ID NO: 8). To determine whether this sequence can enhance the expression of a transgene on purified exosomes, the PTGFRN signal peptide was compared to a signal peptide of a heterologous protein, DsbA11. HEK293 SF cells were stably transfected with expression constructs encoding (i) full length wild-type PTGFRN fused to GFP; (ii) a short fragment of PTGFRN (454-PTGFRN; SEQ ID NO: 33) containing the endogenous PTGFRN signal peptide fused to GFP; or (iii) a short fragment of PTGFRN (454-PTGFRN; SEQ ID NO: 33) having the endogenous PTGFRN signal peptide replaced with a signal peptide from the bacterial gene DsbA11 (Koerber et al., Journal of molecular biology, 427.2 (2015): 576-586), fused to GFP. As shown in FIG. 39, cells expressing GFP fusion protein containing full-length or truncated PTGFRN-GFP containing the endogenous PTGFRN signal peptide produced exosomes including GFP at similarly high levels. Cells expressing GFP fusion protein containing truncated PTGFRN with the DsbA11 signal peptide, however, produced exosomes expressing GFP at much lower levels. These results demonstrate that the PTGFRN signal peptide promotes high density decoration of engineered exosomes.

6.9.14. Example 14: Antibody Fragments Can Be Functionally Expressed on the Exosome Surface Using PTGFRN as a Scaffold Experimental data described above demonstrate that PTGFRN is a robust scaffold amenable to overexpression of many classes of proteins. Antibodies and antigen-binding fragments of antibodies are an important class of therapeutic peptides with diverse applications in many treating many diseases. To determine whether a functional antigen-binding fragment could be expressed on exosomes using PTGFRN as a scaffold, HEK29SF cells were stably transfected to overexpress a fusion protein consisting of a single chain Fab recognizing the lectin CLEC9A (clone 10B4, Millipore Sigma, catalog #04-148; and as described in Caminschi et al., Blood, 112: 8 (2008)), full-length PTGFRN, GFP, and a FLAG tag (FIG. 40A). Optiprep™ purified exosomes were run on a stain-free protein gel and blotted with an antibody against the FLAG tag showing significant overexpression of the full-length fusion protein (FIG. 40B).

The purified anti-CLEC9A exosomes were tested by BLI for binding to immobilized CLEC9A-Fc (R&D Systems, catalog #6049-CL-050; and as described in Uto et al., Nature Communications 7: 11273 (2016)). CLEC9A-Fc was bound to Protein A probes at a final concentration of 0.5 µg/ml in PBS+0.1% (v/v) Tween20, and incubated with $1\times10^{11}$ unmodified exosomes or exosomes modified to express the fusion protein consisting of a single chain Fab recognizing the lectin CLEC9A, a full-length PTGFRN, GFP, and a FLAG tag ("αCLEC9A-PTGFRN") shown in FIG. 40A. As shown in FIG. 41, only the anti-CLEC9A-PTGFRN exosomes bound to the CLEC9A-Fc probe, demonstrating functional recognition between a cell surface marker and exosomes engineered to overexpress an antigen-binding fragment.

6.9.15. Example 15: Mesenchymal Stem Cells Express PTGFRN

Therapeutic exosomes from several cell types have been used for research and clinical purposes. Stem cells of several varieties, including neural precursor stem cells and mesenchymal stem cells have been shown to have therapeutic benefit, but most studies using these cells rely on natural, unmodified exosomes. It would be desirable, therefore, to engineer these cell lines to overexpress specific ligands or other target proteins. Bone marrow-derived mesenchymal stem cells were grown in a 1.1 L microcarrier-based 3D bioreactor system. After five days of cell expansion, the growth media was discarded, and the cells were cultured for another three days in serum-free media. The serum-free media was filtered through a 100 µm filter to remove microcarriers and centrifuged at low speed to remove cell debris and contaminants. The clarified media was then purified by Optiprep™ density-gradient ultracentrifugation as described in Example 1. Purified exosomes from HEK293SF cells and MSCs were analyzed by Western blotting for PTGFRN, and the established exosome proteins ALIX, TSG101, CD63, CD9, and CD81. As shown in FIG. 42, all of these proteins were expressed in both HEK293SF cells and MSCs, suggesting that the exosome proteins, e.g., PTGFRN, can be used as a scaffold for generating surface-engineered MSC exosomes.

6.9.16. Example 16: PTGFRN can be Overexpressed on Exosomes from Non-Human Cells The results in Examples 9 and 15 demonstrate that numerous human-derived cell naturally express PTGFRN and the other novel exosome proteins identified in Example 1. To determine whether PTGFRN can be used as a universal exosome scaffold protein, Chinese hamster ovary (CHO) cells were stably transfected with a plasmid expressing full-length PTGFRN fused to a FLAG tag ("the PTGFRN-FLAG plasmid"). Exosomes were purified from wild-type HEK293SF cells, HEK293SF cells transfected with the PTGFRN-FLAG plasmid, CHO cells, and CHO cells transfected with the PTGFRN-FLAG plasmid using the method described in Example 1. As shown in FIGS. 43A-C, PTGFRN-FLAG was successfully overexpressed in both HEK293 SF cells and CHO cells as detected by stain-free PAGE (FIG. 43A) and Western blotting with antibodies against PTGFRN (FIG. 43B) and FLAG (FIG. 43C). This result demonstrates that non-human cells (e.g., CHO cells) as well as human cells (e.g., HEK cells) can produce exosomes that overexpress human PTGFRN. This result indicates that PTGFRN is a universal scaffold protein for generating engineered exosomes from many different cell types and species.

6.9.17. Example 17: PTGFRN Provides Improved Loading of Luminal Cargo Compared to Conventional Exosome Proteins Previous examples demonstrated that PTGFRN overexpression results in exosomes with greater protein number and/or activity compared to conventional exosome proteins (e.g., Example 13; FIG. 15). Since PTGFRN is a transmembrane protein and has its N-terminus on the extravesicular face and its C-terminus in the exosome lumen, PTGFRN may be a suitable scaffold protein to load the lumen of exosomes with cargo proteins. To investigate this possibility, HEK293SF cells were engineered to stably express a bipartite reporter system that uses the small molecule rapamycin to facilitate protein-protein interactions. Either CD9 (FIG. 44A) or PTGFRN (FIG. 44B) were fused to GFP, a FLAG tag, and FKBP. The cells were also engineered to stably express mCherry fused to a V5 tag and FRB. In the presence of the small molecule Rapamycin, the proteins FRB and FKBP dimerize to form a stable complex. Culturing cells in the presence of Rapamycin therefore may allow for association between the mCherry cargo protein and either CD9 or PTGFRN during exosome biogenesis. Exosomes purified from these cells will be washed to remove Rapamycin, allowing for release of the mCherry as soluble cargo in the exosome lumen. (FIGS. 44A-B).

The CD9 loading reporter cells were grown in the presence of Rapamycin for 0, 1, or 2 days. The PTGFRN loading reporter cells were grown in the presence of Rapamycin for 5 days. Exosomes were purified from the cell cultures in the absence of Rapamycin allowing for cargo release in the exosome lumen. Purified exosome samples were run on a denaturing polyacrylamide gel and analyzed for the presence of total protein and Western blotting against the scaffold protein (anti-FLAG) or the mCherry cargo (anti-V5). The PTGFRN samples were loaded on the polyacrylamide gel with much less material compared to the CD9 samples, but PTGFRN was readily detectable by FLAG Western blotting. The cargo mCherry was also detected at a comparable level between the PTGFRN and CD9 scaffold samples (FIG. 45A). When the scaffold and cargo protein bands were measured by densitometry and normalized to the amount of collected exosomes, the PTGFRN scaffold was expressed at a higher level and was able to load much more mCherry cargo contained in the CD9 scaffold proteins (FIG. 45B). These data indicate that PTGFRN can be expressed as a fusion protein to a luminal loading peptide to a greater extent than the conventional exosome protein CD9, and that the use of PTGFRN results in greater directed cargo loading compared to the conventional exosome protein. These data indicate that complex, multi-part engineering systems can be used in the context of a PTGFRN scaffold and result in robust cargo loading in the exosome lumen.

6.9.18. Example 18: Generation of Modified Exosome Proteins

A polynucleotide encoding a modified exosome protein is generated using a polynucleotide encoding a whole exosome protein or a truncated exosome protein. A specific truncated exosome protein is selected by screening various truncated exosome proteins and selecting a truncated protein having optimal capabilities to incorporate into exosome membranes and interact with a binding agent. Targeting of the truncated proteins to exosome membranes is tested by nano-flow cytometry.

A polynucleotide encoding a modified exosome protein is generated by adding a polynucleotide encoding an affinity tag (glutathione-S-transferase, S-peptide, FLAG tag, GFP, etc.) to the polynucleotide encoding a whole or truncated exosome protein (e.g., PTGFRN, BSG, IGSF8, ITGB1, ITGA4, SLC3A2, and ATP transporter). The modified polynucleotide expresses a fusion protein. The polynucleotide is further modified to improve their targeting into exosome membranes and/or their affinity to a binding agent.

A different type of polynucleotide encoding a modified exosome protein is generated by adding a polynucleotide encoding a therapeutic peptide (e.g., an antibody, an enzyme, a ligand, a receptor, an antimicrobial peptide, a variant or a fragment thereof) to the polynucleotide encoding a whole or truncated exosome protein (e.g., PTGFRN, BSG, IGSF8, ITGB1, ITGA4, SLC3A2, and ATP transporter). The modified polynucleotide expresses a fusion protein presented on the surface of an exosome. The fusion protein maintains therapeutic activity of the therapeutic peptide.

A different type of polynucleotide encoding a modified exosome protein is generated by adding a polynucleotide encoding a targeting moiety (e.g., a targeting moiety specific to a specific organ, tissue or cell) to the polynucleotide encoding a whole or truncated exosome protein (e.g., PTGFRN, BSG, IGSF8, ITGB1, ITGA4, SLC3A2, and ATP transporter). The modified polynucleotide expresses a fusion protein presented on the surface of an exosome. The fusion protein allows the exosome to be targeted to a specific organ, tissue or cell.

Localization of modified exosome proteins on the exosome surface is also tested by nano flow cytometry.

6.9.19. Example 19: Generation of Surface-Engineered Exosomes

A producer cell generating surface-engineered exosomes is made by introducing an exogenous sequence encoding an exosome protein or a variant or a fragment of the exosome protein. A plasmid encoding an exosome protein is transiently transfected to induce high-level expression of the exosome protein on the exosome surface. A plasmid encoding a modified exosome protein is transiently transfected to produce exosomes having the modified exosome protein on the surface.

A polynucleotide encoding an exosome protein, a variant or a fragment of an exosome protein, or an exogenous sequence encoding an affinity tag, a therapeutic peptide or a targeting moiety is stably transformed into a producer cell to produce surface-engineered exosomes. The exogenous sequence encoding an affinity tag, a therapeutic peptide or a targeting moiety is inserted into a genomic site encoding an exosome protein to generate a fusion protein comprising the affinity tag attached to the exosome protein. A polynucleotide encoding a modified exosome protein is knocked in to a genomic site encoding an exosome protein.

A producer cell line is generated by stably transfecting at least two polynucleotides, each encoding an exosome protein, a variant or a fragment of an exosome protein, or an exogenous peptide (e.g., affinity tag, targeting moiety, therapeutic peptide). A different producer cell line is also generated by inserting two or more exogenous sequences (e.g., exogenous sequences encoding an affinity tag, a marker, a targeting peptide, a therapeutic peptide, etc.) into multiple genomic sites, within or in a close proximity to the genomic sequence encoding an exosome protein, to generate a surface-engineered exosome comprising multiple modified exosome proteins. Each of the plurality of modified exosome proteins is targeted to the surface of exosomes. The exosomes have affinities to two different binding agents and are purified by either or both of the binding agents.

6.9.20. Example 20: Isolation, Purification and Sub-Fractionation of Exosomes by Affinity Purification Binding agents for affinity purification of exosomes are developed by biopanning/directed evolution that elute under mild conditions.

The binding agent is attached to a solid support (e.g., a porous agarose bead) and formed into a conventional chromatography system (e.g., GE AKTA). A sample containing exosomes is applied to the column for affinity purification

7. INCORPORATION BY REFERENCE

All publications, patents, patent applications and other documents cited in this application are hereby incorporated by reference in their entireties for all purposes to the same extent as if each individual publication, patent, patent application or other document were individually indicated to be incorporated by reference for all purposes.

8. EQUIVALENTS

The present disclosure provides, inter alia, compositions of cannabinoid and entourage compositions. The present disclosure also provides method of treating neurodegenerative diseases by administering the cannabinoid and entourage compositions. While various specific embodiments have been illustrated and described, the above specification is not restrictive. It will be appreciated that various changes can be made without departing from the spirit and scope of the invention(s). Many variations will become apparent to those skilled in the art upon review of this specification.

What is claimed is:

1. A pharmaceutical composition comprising:
   a. an exosome comprising a target protein, wherein at least a part of the target protein is expressed from an exogenous sequence, and the target protein comprises Prostaglandin F2 Receptor Negative Regulator (PTGFRN) or a fragment thereof and:
   b. an excipient.

2. The pharmaceutical composition of claim 1, wherein the target protein comprises a polypeptide of SEQ ID NO: 1.

3. The pharmaceutical composition of claim 1, wherein the target protein comprises a polypeptide of SEQ ID NO: 33.

4. The pharmaceutical composition of claim 1, produced from a cell genetically modified to comprise the exogenous sequence.

5. The pharmaceutical composition of claim 4, wherein the cell is an HEK293 cell.

6. The pharmaceutical composition of claim 4, wherein the cell comprises a plasmid comprising the exogenous sequence.

7. The pharmaceutical composition of claim 4, wherein the cell comprises the exogenous sequence inserted into a genome of the cell.

8. The pharmaceutical composition of claim 7, wherein the exogenous sequence is inserted into a genomic site located 3' or 5' end of a genomic sequence encoding PTGFRN or a fragment thereof.

9. The pharmaceutical composition of claim 7, wherein the exogenous sequence is inserted into a genomic sequence encoding PTGFRN.

10. The pharmaceutical composition of claim 4, wherein the cell is modified to have a reduced expression of ADAM10.

11. The pharmaceutical composition of claim 1, wherein the target protein is a fusion protein comprising PTGFRN or a fragment thereof, and a therapeutic peptide.

12. The pharmaceutical composition of claim 11, wherein the therapeutic peptide is selected from the group consisting of a natural peptide, a recombinant peptide, a synthetic peptide, or a linker to a therapeutic compound.

13. The pharmaceutical composition of claim 11, wherein the therapeutic compound is selected from the group consisting of nucleotides, amino acids, lipids, carbohydrates, and small molecules.

14. The pharmaceutical composition of claim 11, wherein the therapeutic peptide is an antibody or a fragment thereof.

15. The pharmaceutical composition of claim 11, wherein the therapeutic peptide is an enzyme, a ligand, a receptor, or a fragment thereof.

16. The pharmaceutical composition of claim 1, wherein the target protein is a fusion protein comprising PTGFRN or a fragment thereof, and a targeting moiety.

17. The pharmaceutical composition of claim 16, wherein the targeting moiety is specific to an organ, a tissue, or a cell.

18. The pharmaceutical composition of claim 1, substantially free of macromolecules, wherein the macromolecules are selected from nucleic acids, contaminant proteins, lipids, carbohydrates, metabolites, and a combination thereof.

19. The pharmaceutical composition of claim 1, wherein the exosome further comprises a second target protein, wherein the second target protein comprises PTGFRN, BSG, IGSF3, IGSF2, ITGB1, ITGA4, SLC3A2, ATP transporter, or a fragment thereof.

* * * * *